(12) United States Patent
Thieberger et al.

(10) Patent No.: US 9,015,084 B2
(45) Date of Patent: Apr. 21, 2015

(54) ESTIMATING AFFECTIVE RESPONSE TO A TOKEN INSTANCE OF INTEREST

(71) Applicants: Gil Thieberger, Kiryat Tivon (IL); Ari M Frank, Haifa (IL)

(72) Inventors: Gil Thieberger, Kiryat Tivon (IL); Ari M Frank, Haifa (IL)

(*) Notice: Subject to any disclaimer, the term of this patent is extended or adjusted under 35 U.S.C. 154(b) by 246 days.

(21) Appl. No.: 13/656,704

(22) Filed: Oct. 20, 2012

(65) Prior Publication Data

US 2013/0103624 A1 Apr. 25, 2013

Related U.S. Application Data

(60) Provisional application No. 61/549,218, filed on Oct. 20, 2011.

(51) Int. Cl.
| | | |
|---|---|---|
| G06F 15/18 | (2006.01) | |
| G06N 99/00 | (2010.01) | |
| G06Q 10/06 | (2012.01) | |

(52) U.S. Cl.
CPC ............ *G06N 99/005* (2013.01); *G06Q 10/063* (2013.01)

(58) Field of Classification Search
None
See application file for complete search history.

(56) References Cited

U.S. PATENT DOCUMENTS

| | | | |
|---|---|---|---|
| 4,632,126 A * | 12/1986 | Aguilar | 600/545 |
| 5,676,138 A | 10/1997 | Zawilinski | |
| 6,190,314 B1 | 2/2001 | Ark et al. | |
| 6,309,342 B1 | 10/2001 | Blazey et al. | |
| 6,798,898 B1 * | 9/2004 | Patton et al. | 382/128 |
| 7,930,199 B1 | 4/2011 | Hill | |
| 8,224,106 B2 | 7/2012 | Bing et al. | |
| 8,234,262 B2 | 7/2012 | Jung et al. | |
| 8,296,172 B2 | 10/2012 | Marci et al. | |
| 8,308,562 B2 | 11/2012 | Patton | |
| 8,335,715 B2 | 12/2012 | Pradeep et al. | |
| 8,386,312 B2 | 2/2013 | Pradeep et al. | |
| 8,392,253 B2 | 3/2013 | Pradeep et al. | |
| 8,392,255 B2 | 3/2013 | Pradeep et al. | |
| 8,484,081 B2 | 7/2013 | Pradeep et al. | |
| 8,777,630 B2 * | 7/2014 | Duffy | 434/236 |
| 2007/0073585 A1 * | 3/2007 | Apple et al. | 705/14 |
| 2007/0162505 A1 | 7/2007 | Cecchi et al. | |
| 2008/0065468 A1 | 3/2008 | Berg et al. | |
| 2008/0096533 A1 | 4/2008 | Manfredi et al. | |
| 2008/0221401 A1 | 9/2008 | Derchak et al. | |
| 2009/0024449 A1 | 1/2009 | Pradeep et al. | |
| 2010/0010317 A1 | 1/2010 | De Lemos | |

(Continued)

OTHER PUBLICATIONS

"Affective Characterization of Movie Scenes Based on Multimedia Content Analysis and User's Physiological Emotional Responses"; Mohammad Soleymani, Guillaume Chanel, Joep J.M. Kierkels, Thierry Pun; Computer Vision and Multimedia Laboratory, Computer Science Department 2008 IEEE Tenth IEEE International Symposium on Multimedia.*

(Continued)

*Primary Examiner* — Kakali Chaki
*Assistant Examiner* — Luis Sitiriche

(57) ABSTRACT

A user may be exposed to multiple token instances representing stimuli that may influence the affective state of the user. Described herein are embodiments of systems, method, and computer programs for estimating affective response to a token instance of interest, selected from among the token instances. In one example embodiment, the token instance of interest is a token instance for which attention level of the user is higher than at least one other token instance.

20 Claims, 21 Drawing Sheets

(56) References Cited

U.S. PATENT DOCUMENTS

2010/0211439 A1    8/2010    Marci et al.
2011/0106750 A1    5/2011    Pradeep et al.

OTHER PUBLICATIONS

Calvo, R. A., & D'Mello, S., "Affect Detection: An Interdisciplinary Review of Models, Methods, and Their Applications", IEEE Transactions on affective computing, 2010, 1(1), 18-37.

Gunes, H., & Pantic, M.,"Automatic, Dimensional and Continuous Emotion Recognition", International Journal of Synthetic Emotions, 2010, 1 (1), 68-99.

Hanjalic, A., & Xu, L.-Q. , "Affective video content representation and modeling", IEEE Transactions on Multimedia, 2005, 7(1), 143-154.

Nicolaou, M. A., Gunes, H., & Pantic, M., "Continuous Prediction of Spontaneous Affect from Multiple Cues and Modalities in Valence-Arousal Space", IEEE Transactions on Affective Computing, 2011, 2 (2), 92-105.

Spain, M. & Perona, P., "Measuring and Predicting Object Importance", International Journal of Computer Vision, 2011, 91 (1). pp. 59-76.

Zeng, Z., Pantic, M., Roisman, G., & Huang, T., "A survey of affect recognition methods: audio, visual, and spontaneous expressions", IEEE Transactions on Pattern Analysis and Machine Intelligence, 2009, 31 (1), 39-58.

van Broek, E. L., Janssen, J. H., Zwaag, M. D., D. M. Westerink, J. H., & Healey, J. A., "Prerequisites for Affective Signal Processing (ASP)", In Proceedings of the International Joint Conference on Biomedical Engineering Systems and Technologies, INSTICC Press, 2009, parts I.

van Broek, E. L., Janssen, J. H., Zwaag, M. D., D. M. Westerink, J. H., & Healey, J. A., "Prerequisites for Affective Signal Processing (ASP)—Part II", In Proceedings of the International Joint Conference on Biomedical Engineering Systems and Technologies, INSTICC Press, 2009, parts II.

van Broek, E. L., Janssen, J. H., Zwaag, M. D., D. M. Westerink, J. H., & Healey, J. A., "Prerequisites for Affective Signal Processing (ASP)—Part III", In Proceedings of the International Joint Conference on Biomedical Engineering Systems and Technologies, INSTICC Press, 2009, parts III.

van Broek, E. L., Janssen, J. H., Zwaag, M. D., D. M. Westerink, J. H., & Healey, J. A., "Prerequisites for Affective Signal Processing (ASP)—Part IV", In Proceedings of the International Joint Conference on Biomedical Engineering Systems and Technologies, INSTICC Press, 2009, parts IV.

\* cited by examiner

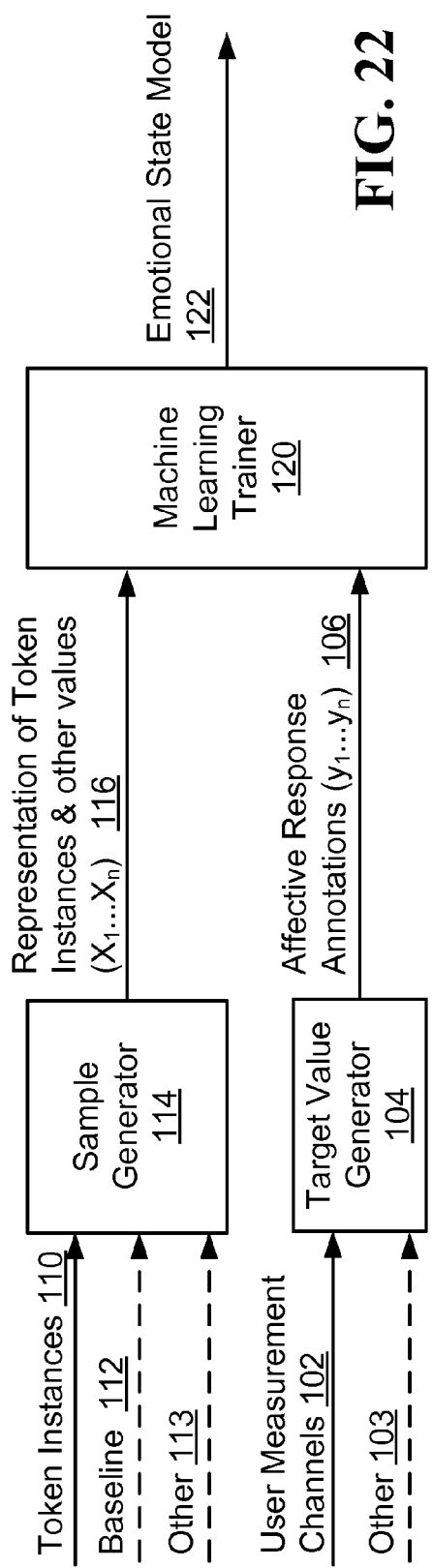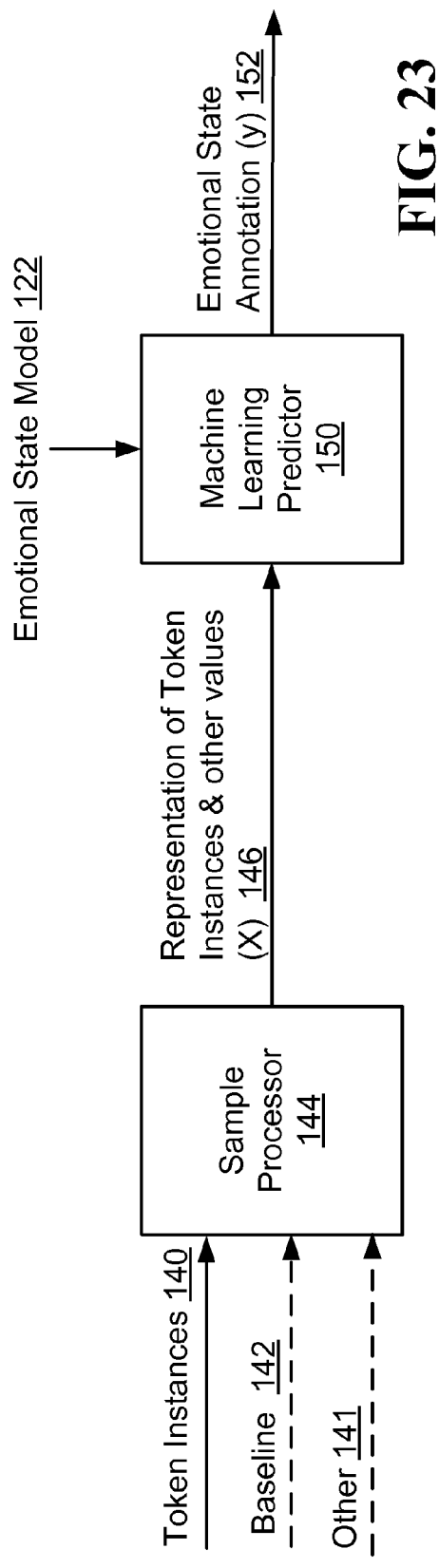

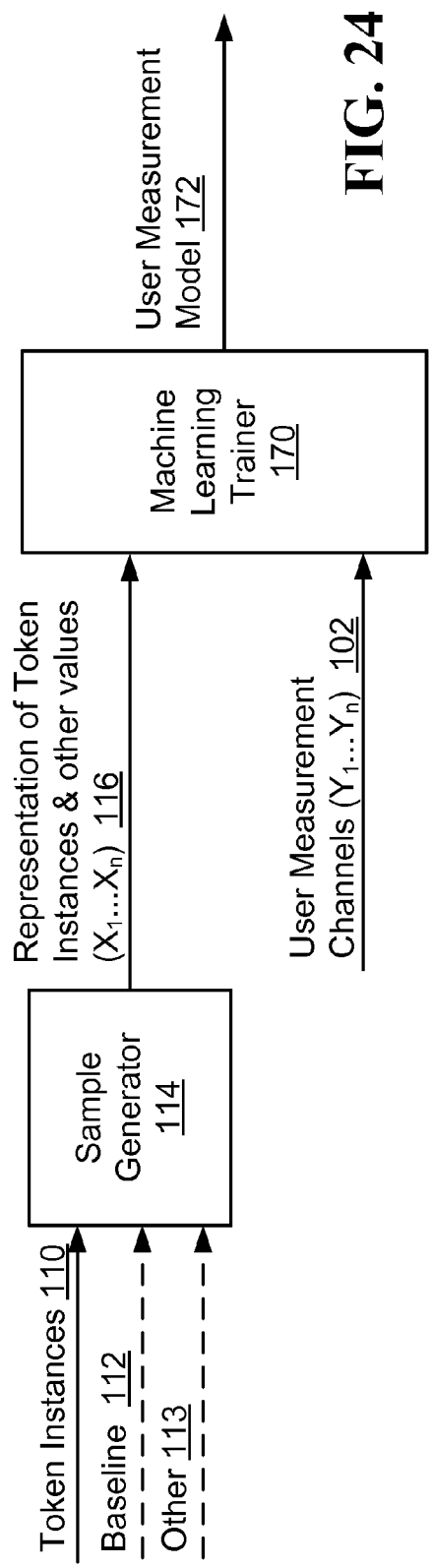
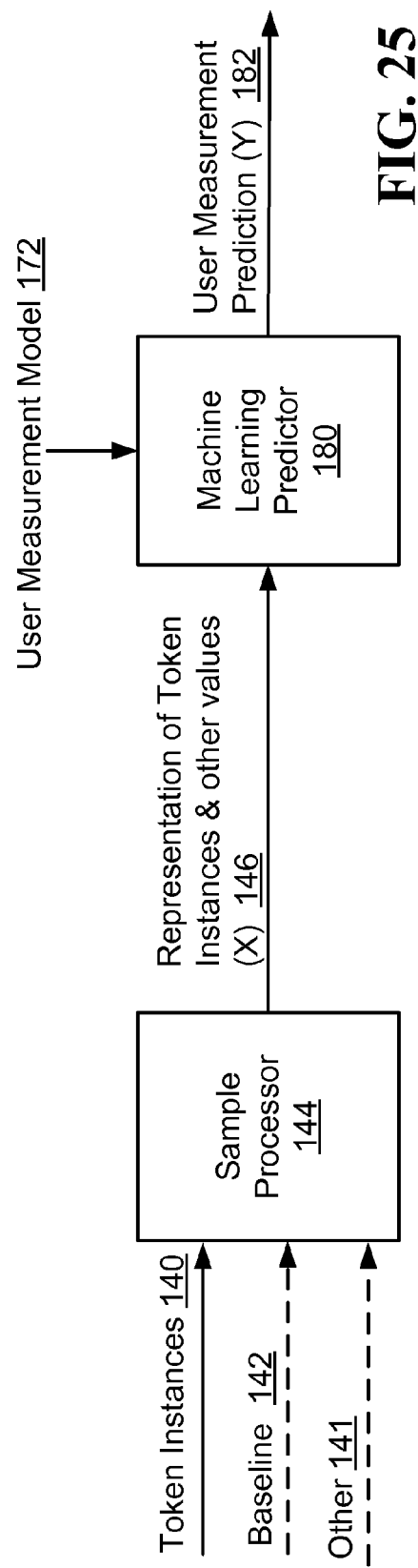

US 9,015,084 B2

ESTIMATING AFFECTIVE RESPONSE TO A TOKEN INSTANCE OF INTEREST

CROSS-REFERENCE TO RELATED APPLICATIONS

This application claims the benefit of U.S. Provisional Patent Application No. 61/549,218, filed Oct. 20, 2011.

BACKGROUND

People these days have a seemingly endless number of options when it comes to interacting with the digital world. There is a virtually infinite number of digital media objects and activities at their fingertips such as videos, music, games, websites, and virtual worlds. In addition, the advances in computing make it possible to personalize digital content for users, not only by bringing users specific content of their liking (such as streaming music, videos, loading games, or virtual worlds), but also generating content especially tailored to their taste (e.g., by rendering specific images in videos or games). Such personalization makes it possible for each user to get the most suitable, enjoyable and effective content on demand. However, in order to optimize and tune an experience to an individual user's liking, it is important to be able to discern the user's specific reaction to various objects and/or changes in specific details.

One of the main problems limiting widespread adoption of advanced personalization of digital experiences is the inadequacy of current user preference modeling. While models of a user's implicit preferences can be created by analysis of the user's digital footprint (e.g., visit to websites, online purchases, or semantic analysis of user correspondences), they can typically only answer broad questions regarding the user's preferences toward the entire content or experience. For example, such models are able to provide answers to broad questions like: Does the user like action videos or romantic comedies? Does the user like cars? Similarly, analysis of the user's explicit preference indications (e.g., Facebook's "Like" or Google's "+1" buttons) only provides information on the user's feeling towards content items in their entirety (e.g., a website, a video clip, or a book purchased on Amazon).

One area in computer science, which has been showing tremendous progress in recent years, is affective computing. Advances in the area of affective computing are making it possible to continuously monitor a user's emotional state (also called affective response), using a wide array of sensors that measure physiological signals and/or behavioral queues. As the technology advances and the systems used to measure affective response are becoming cheaper, much smaller and more comfortable to wear, affective computing is moving from laboratories to day-to-day applications. However, even measuring a user's affective response, usually only provides indications of the user's attitude to the content in its entirety, such as revealing the user's response to a whole viewed scene, or the last minute of game play.

The aforementioned methods fall short when it comes to understanding the user's attitude towards specific details, which may be valuable for effective personalization. These methods also fall short of answering simple questions such as, how does the user feel towards a specific character in a game? Which villain elicits a stronger reaction in a battle scene? Would a user prefer that a presenter in an insurance advertisement be a man or a woman? Should that presenter be dressed in casual or formal attire? Should the sofa in the background be blue or beige? Knowing such details can help make personalized content that suits a user's specific taste, which makes the content more engaging and likeable.

Thus, there is a need to be able to discern specific details regarding a user's preferences in order to make more accurate user models and improve content personalization for users.

BRIEF SUMMARY

The emergence ubiquitous computing, with sensors and computers being embedded in clothing and accessories (e.g., bracelets), and even implanted in the human body, bring many opportunities for utilizing affective computing systems to gain much better understanding of the user's feelings and attitudes. Some of the disclosed embodiments describe methods for learning the user's preferences towards specific details and/or objects such as characters, images, and/or sounds viewed by a user in video clips, games, and/or interaction with real and/or virtual worlds (these details and objects are referred to as "token instances").

Some aspects of this disclosure rely on measuring user modalities (also referred to as "user measurement channels"), in conjunction with algorithms for identifying interesting objects to which the user pays attention (these are referred to as "token instances of interest"). The change in the user's affective response may be attributed, at least in part, to the user's reaction to the token instances of interest. By monitoring the user over time, when exposed to different token instances, it is possible to deduce how the user will react to future exposures to different objects and in particular to compare the user's reaction to different token instances (e.g., monster A vs. monster B in a video game, cats vs. dogs in a commercial). Optionally, this information may be compiled into a library; thus making it possible to model a user's likes and dislikes and use that information to personalize new content and/or experiences tailored for the user.

Some aspects of this disclosure include a memory coupled with a processor. The memory stores information relating to token instances to which a user is exposed (e.g., stimuli such as images and/or sounds), a response of the user to the token instances, and information regarding attention of the user at that time. Optionally, the response may be an emotional response (e.g., predicted from models) and/or an affective response (e.g., measured values from one or more user measurement channels). Optionally, the information regarding the attention of the user may be predicted (e.g., a prediction made based on the token instances) and/or measured (e.g., measurements obtained from eye-tracking). The processor may process at least some of the stored information in order to determine which one or more of the stored tokens may be considered a token instance of interest. In addition, the processor may compute the response of the user to a determined token instance of interest. In some embodiments, the response of the user to a token instance of interest may be expressed as an affective response in terms of a value and/or change of value to a user measurement channel (e.g., a heart rate, spiking of an EEG signal). Additionally or alternatively, the response of the user to a token instance of interest may be expressed as an affective response in terms an emotional state and/or change to emotional state (e.g., happiness, becoming excited).

Some aspects of this disclosure involve determining the user's response to token instances of interest by comparing a measured response of the user when exposed to a certain content or experience, with the predicted response of the user when exposed to essentially the same scene or experience without the token instances of interest; thus, the prediction is performed on what may be considered background token instances. The difference between the two values can be attributed (at least in part) to the user's response to the token instances of interest. By monitoring the user over time, when exposed to different token instances, it is possible to deduce how the user will react to future exposures to different objects and in particular to compare the user's reaction to different token instances (e.g., monster A vs. monster B in a video game, cats vs. dogs in a commercial). Note that in some embodiments, it is not necessary to know which of the token instances are token instances of interest, only knowledge of the background token instances is required. Thus, the method is suitable for the task of detecting the presence of novel or unexpected token instances to which the user pays attention and affect his/her response. Thus, after the detection of the presence of such tokens, further effort (e.g., algorithmic or manual annotation) might be applied in order to identify which of the novel images, sounds or effects should be labeled as token instances (and also determine their unexpected effect on the user).

Some aspects of this disclosure may be especially suitable for characterizing the user's response to token instances in domains like video games and virtual worlds, since in such domains measurements of the user may be taken multiple times while experiencing in essentially the same, very similar, repetitive scenes or missions. This makes it possible to train accurate situation-specific predictors of the user's response for those cases. Therefore, any significant variation detected between the predicted user's response to background tokens, and the measured response to the full set of token instances (both background and token instances of interest) may be indicative of the effect of the user's exposure to the token instances of interest.

Some aspects of this disclosure involve systems that include a processor and a decomposer. The processor is configured to predict a user's response to background token instances to which the user is exposed. The decomposer receives a measured response to the background token instances and an additional token instance of interest. The decomposer also estimates the response to the token instance of interest according to the difference between the measured response (that includes the token instance of interest) and the predicted response (that does not include the token instance of interest).

Some aspects of this disclosure involve receiving information on the attention level of the user in token instances to which the user is exposed. The information on the attention level may enable the selection of a token instance of interest. A predictor may be used to predict the user's response to the token instances without the token instance of interest. Comparing the user's predicted response to an actual response of the user that was measured when the user was exposed to all of the token instances can enable the estimation of the user's response to the token instance of interest.

Some aspects of this disclosure involve measuring the user's affective response during numerous iterations the user has experiencing essentially the same scene (e.g., a visit to a website, and/or game play of a level). This enables accurate modeling of the user's typical affective response to the scene (and essentially similar variations of it). Thus, if the user visits the same scene but with an additional element introduced that is not part of the typical scene (e.g., a new sound effect, a new character, and/or additional graphics), any change in the user's affective response can be attributed (at least in part) to the user's reaction to the new introduced element Some aspects of this disclosure involve a memory coupled to a processor. The memory stores response of a user to multiple variants of a repetitive scene and an additional response of the user to an additional variant of the scene that includes a specific token instance that is not included in the other variants. The processor utilizes the information stored in the memory to estimate the response of the user to the specific token instance.

Some aspects of this disclosure involve a memory coupled to a processor. The memory stores response of a user to multiple variants of a repetitive scene and an additional response of the user to an additional variant of the scene that lacks a certain token instance. The processor utilizes the information stored in the memory to estimate the response of the user to the certain token instance.

BRIEF DESCRIPTION OF THE DRAWINGS

The embodiments are herein described, by way of example only, with reference to the accompanying drawings. In the drawings:

FIG. 22 illustrates training an emotional state model;

FIG. 23 illustrates an emotional state predictor;

FIG. 24 illustrates training a user measurement model;

FIG. 25 illustrates a predictor for user measurements;

DETAILED DESCRIPTION

Figure 1:
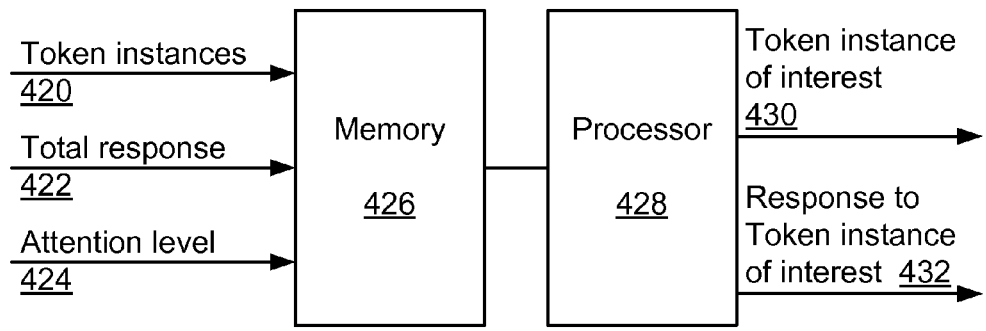
FIG. 1 illustrates a system that identifies as token instance of interest and estimates the response to it.

In some embodiment, the system processes user measurement channels and/or tokens. The user measurement channels are data obtained from monitoring a user. The tokens may include one or more of the following types of data pertaining to: (i) the sensual stimuli to which the user is exposed, (ii) the user's cognitive condition, (iii) the user's situation, and/or (iv) the user's physiological condition. More detailed and comprehensive explanations about different types of data collected and processed by some of the disclosed embodiments are provided below.

The term "affective response", which may also be referred to as "affect", describes an entity's emotional state (for example a human beings emotional state). Affective response may also describe the physiological and/or behavioral manifestation of an entity's emotional state, for example as observed or measured via user measurement channels. The terms "affective response/state" and "emotional response/state" may be used herein interchangeably, but usually the affective response is derived from measurements or observations, while the emotional state is predicted from models.

The term "user measurement channels", or the alternative form "measurement channels of the user", refer to physiological measurements and/or measurements of unsolicited behavioral cues of the user, which may be either raw measurements and/or processed measurements (e.g., resulting from filtration, calibration, and/or feature extraction). Examples of physiological measurements include various types of signals taken of the user's physiological state using sensors for physiological properties, such as heart rate (HR), Blood-Volume Pulse (BVP), Galvanic Skin Response (GSR), Skin Temperature (ST), respiration, electroencephalography (EEG), electrocardiography (ECG), electromyography (EMG), Electrodermal Activity (EDA), and others. Examples of measurements of unsolicited behavioral cues of the user include measurements derived from one or more cameras (e.g., detecting body gestures, facial expressions, microexpressions), microphones (e.g., detecting vocal cues, analysis of user's unsolicited speech), movement sensors, acoustic sensors, and/or pressure sensors. The user measurements may utilize various existing, and/or yet to be invented, sensors and measurement devices that may be attached to the body, clothing (such as gloves, shirts, helmets), implanted in the user's body, and/or remote sensors external to the user's body. It is noted that the user measurement channels are often referred to in the literature as "modalities". In one embodiment, the user measurement channels may be received by the system as raw data, and/or after filtration (e.g., noise cancellation), and/or after signal processing (e.g., after speech recognition, image analysis, and/or feature extraction from inputs like facial expression, microexpressions, audio samples, user movements).

The user measurement channels do not include solicited feedback from the user, such as (i) questions the user may answer to rate an experience and/or activity (e.g., eBay seller feedback), (ii) a mechanism in which the user can actively provide a feedback, such as Facebook's "Like" button or Google's "+1" button, and/or (iii) a analysis of feedback in the form of text or speech, that is provided by the user upon request, or at an agreed upon time or situation, such as at the end of a video clip, or after prompting the user (e.g., by asking a question such as "how did you feel about that?"). One of the properties that distinguish between solicited and unsolicited feedback is that with solicited feedback the system can usually determine when the feedback is given and the object that is the target of the feedback, while with unsolicited feedback this information may need to be inferred, and thus usually requires additional steps.

The term "token" refers to a thing that has a potential to influence the user's affective response. Optionally, tokens may be categorized according to their source with respect to the user: external or internal tokens. In one embodiment, the tokens may include one or more of the following:

(i) Information referring to a sensual stimulus or a group of sensual stimuli that may be experienced or sensed by the user. These tokens usually have a specified source such as objects or systems in the user's vicinity or that the user is interacting with in some way, such as digital or printed media, augmented reality devices, robotic systems, food, and/or beverages. For example, a token may be an item (e.g. car), a movie genre (e.g., "comedy"), a type of image (e.g., "image of person"); a specific character (e.g., "Taco Bell Chihuahua"); web-site (e.g., "Facebook"); Scents or fragrances (e.g., "Chanel no. 5"); a flavor (e.g., "salty"), a physical sensation (e.g., "pressure on the back").

(ii) Properties or values derived from a stimulus or group of stimuli. For example, the rate in which scenes change in a movie; the sound energy level; the font-size in a web-page; the level of civility in which a robot conducts its interaction with a user.

(iii) Information about the environmental conditions that may influence the user's affective response. For example, a token may refer to the user's location (e.g., home vs. outdoors), the time of day, lighting, general noise level, temperature, humidity, speed (for instance, when traveling in a car).

(iv) Information about the user's physiological and/or cognitive state. For example, the user's estimated physical and/or mental health, the user's estimated mood and/or disposition, the user's level of alertness and/or intoxication.

A token and/or a combination of tokens may represent a situation that if the user becomes aware of it, is expected to change the user's affective response to certain stimuli. In one example, monitoring the user over a long period, and in diverse combinations of day-to-day tokens representing different situations, reveals variations in the affective response that are situation-dependent, which may not be revealed when monitoring the user over a short period or in a narrow set of similar situations. Examples of different situations may involve factors such as: presence of other people in the vicinity of the user (e.g., being alone may be a different situation than being with company), the user's mood (e.g., the user being depressed may be considered a different situation than the user being happy), the type of activity the user is doing at the time (e.g., watching a movie, participating in a meeting, driving a car, may all be different situations). In some examples, different situations may be characterized in one or more of the following ways: (a) the user exhibits a noticeably different affective response to some of the token instances, (b) the user is exposed to significantly different subsets of tokens, (c) the user has a noticeably different user emotional state baseline value, (d) the user has a noticeably different user measurement channel baseline value, and/or (e) samples derived from temporal windows of token instances are clustered, and samples falling into the same cluster are assumed to belong to the same situation, while samples that fall in different clusters are assumed to belong to different situations.

The term "token instance" refers to the manifestation of a token during a defined period of time and/or event. The relationship between a token and its instantiation (i.e., the token instance) is somewhat similar to the relationship between a class and its object in a programming language. For example, a movie the user is watching is an instance of the token "movie" or the token "The Blues Brothers Movie"; an image of a soda can viewed through a virtual reality enabled device is a token instance of "soda can"; the sound of the soda can opening in an augmented reality video clip played when viewing the can may be considered a token instance of "soda can popping sound"; the scent of Chanel 5 that the user smelt in a department store while shopping for a present is an instance of the token "perfume scent", or a more specific token may be "scent of Chanel no. 5"; the temperature in the room where the user is sitting may be considered an instance of the token "temperature is above 78 F"; the indication that the user sitting alone in the room is an instance of the token "being alone", and the indication that the user is suffering from the flu may be considered an instance of the token "sick".

The term "exposure" in the context of a user being exposed to token instances means that the user is in a position to process and/or be influenced by the token instances, be they of any source or type.

The response of a user to token instances may refer to the affective response of the user to being exposed to the token instances. Optionally, response may be expressed as a value, and/or a change to a value, of a user measurement channel. Additionally or alternatively, the response may be expressed as a value, and/or a change to a value, of an emotional state.

The term "token source" refers to an element that influences the user's affective state via the user's exposure to the element's token instances. The token instances may be generated by the token source (e.g., a robot providing token instances describing its operations), by the system (e.g., the system performs semantic analysis to a voice conversation), and/or received from a third party (e.g., the system accesses token instance repository for multimedia the user was exposed to). The term "distinct token sources" refers to token sources that are both distinguishable from the user's perspective and operate essentially independently. For example, a massage robot, a television, and a word processing software operating simultaneously are distinct token sources, while audio and video stimuli generated by a computer game are considered as originating from the same token source. In one embodiment, a token instance may be associated with one or more sources. Optionally, a token instance without a defined token source may be attributed to an arbitrary token source, such as the environment.

The term "temporal window of token instances", also referred to as "window", refers to a set of token instances and other optional values, which correspond to a temporal scope defined by the window. In one example, the window may contain token instances for which at least some portion of their existence took place within the temporal scope that defines the window. In another example, the temporal window of token instances is a snapshot of the token instances that existed in a specific time point. Optionally, the window may have a fixed duration. Optionally, the window may have a variable length, for example spanning a certain event, such as the user's viewing of a commercial, visiting a web site, interacting with a robot, or reading an article. Optionally, the window may include values other than token instances derived from other sources such as user measurement channels.

Deciding which token instances belong to a temporal window of token instances may be arbitrary. For example, a system may decide that certain images the user is exposed to in a video clip are described by token instances, while others may be left without incorporating token instances associated with them into the temporal window of token instances.

When a user is exposed to a temporal window of token instances, it means that the user is exposed to the token instances that belong to the temporal window of token instances. Similarly, a user's response to a temporal window of token instances is the response of the user to the token instances that belong to the temporal window of token instances.

In one embodiment, any group of token instances that occur within a certain temporal scope may be considered a temporal window of token instances that corresponds to the certain temporal scope.

In some embodiments, "target value" describes the result of applying a machine learning prediction algorithm to an input instance. The target value may be represented by a state, a category, and/or a measurement. Optionally, a target value may be associated with a temporal window of token instances or with one or more token instances. For example, a target value may be an emotional state prediction of the user, or a value derived from the user measurement channels. Optionally, the target value may be represented by discrete categories, a univariate value, or a point in a multidimensional space. In one example, the target value represents a transition between two categorical states. In another example, the target value represents the difference between the user's states at times corresponding to the end and beginning of a temporal window of token instances. In still another example, the target value represents an average value of a variable computed over the values of the variable during the time covered by a temporal window of token instances.

FIG. 1 illustrates one embodiment of a system configured to estimate a response of a user to a token instance of interest 430. The system includes at least a memory 426 and a processor 428.

The memory 426 is configured to store token instances 420 to which the user is exposed. The memory 426 is also configured to store a total response 422 of the user to the token instances 420.

In addition, the memory 426 is configured to store at least two respective representations of attention level 424 of the user in at least two of the token instances. Optionally, each of the two respective representations enables an assignment of an interest level in one of the token instances. Additionally, the at least two token instances have overlapping instantiation periods (i.e., there is a time during which the user is simultaneously exposed to the two token instances).

The processor 428 is configured to select the token instance of interest 430 from among the at least two of the token instances based on the representations of attention level 424. The processor 428 is also configured to estimate the response to the token instance of interest 432 from the total response of the user to the token instances 422.

Figure 2:
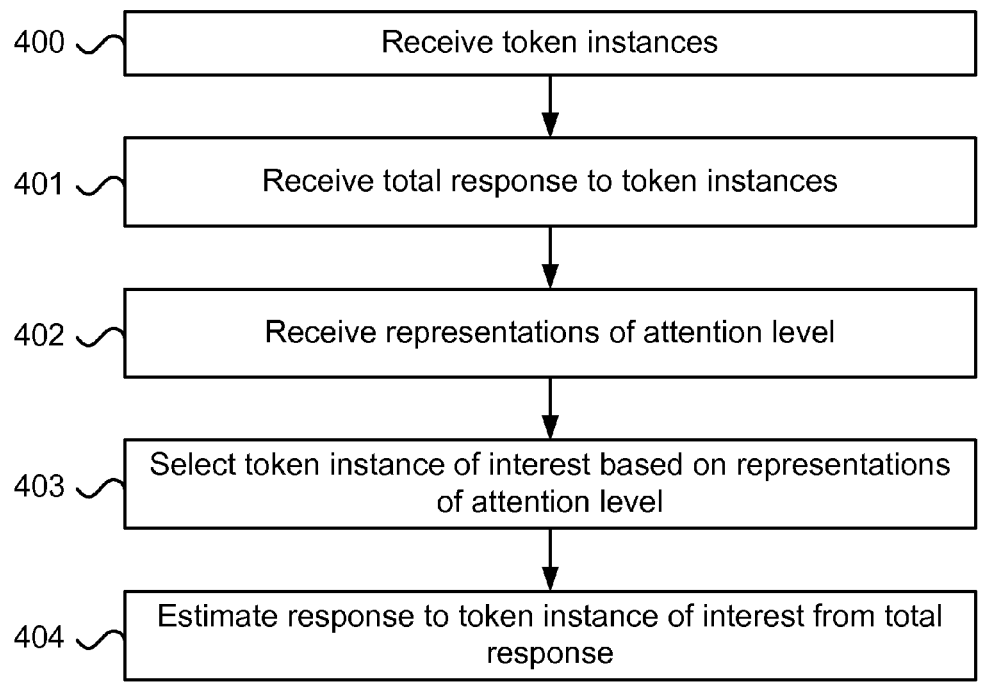
FIG. 2 illustrates a block diagram for identifying a token instance of interest and estimating the response to it.

FIG. 2 illustrates one embodiment of a method for estimating a user's response to a token instance of interest. The method includes the following steps:

In step 400, receiving token instances to which the user was exposed during a certain duration. Optionally, the token instances may belong to a certain temporal window of token instances that spans the certain duration.

In step 401, receiving a total response of the user to the token instances.

In one embodiment, the total response of the user is derived from measurements of the user taken with a sensor. Optionally, values representing the total response of the user are expressed as an affective response in terms of values of a user measurement channel and/or changes to values of a user measurement channel. Optionally, values representing the total response of the user are expressed as an affective response that may be emotional state and/or change to an emotional state.

In step 402, receiving at least two representations of attention level representing the user's attention in at least two of the token instances. The at least two token instances have overlapping instantiation periods (i.e., there is a time during which the user is simultaneously exposed to both token instances). Optionally, the representations of attention levels may be used to assign at least one of the at least two token instances with an attention level (e.g., a relative or absolute value representing the attention in the token instance).

In step 403, selecting a token instance of interest from among the at least two token instances according to the attention level values. Optionally, the token instance of interest is selected as the token instance for which the attention level is highest.

And in step 404, estimating the response to the token instance of interest from the total response of the user to the token instances.

In one embodiment, the received token instances correspond to various types of entities, e.g., images, plot elements, semantic meanings, sounds, sensations, flavors, temperatures, and/or the user's situation. Optionally, the received token instances originate from multiple distinct sources. For example, tokens from a server describing digital content the user is viewing and tokens from a computerized system linked to video cameras that describe the people in the user's vicinity. Optionally, received token instances are detected by the user using essentially different sensory pathways. For example, some of the received token instances describe images the user saw and are detected and processed by the user's visual sensory pathway, while other received token instances correspond to sounds heard by the user (possibly at the same time the images were seen), and are detected and processed by the user's auditory sensual pathway. Optionally, at least some of the token instances to which the user was exposed during the time frame are received in the form of temporal windows of token instances to which.

In one embodiment, the token instances that are received may belong to a certain temporal window of token instances that spans a certain duration. Optionally, the certain duration is essentially a fixed duration, for example 10 seconds. Alternatively, the certain duration may have a variable length that corresponds to certain objects or events, such as the length of a scene in a movie, a video clip, or the time required to complete a mission or play through a level in a game. Additionally or alternatively, the certain duration may correspond to the relative time needed to detect a change in a user measurement channel. For example, a duration suitable for detecting a change in heart rate signals might last a few seconds, while a duration suitable for detecting change in skin temperature measurements might span minutes.

In one embodiment, the total response is a measured response, i.e., it is derived from measurements of the user. Alternatively or additionally, the total response may be a predicted response, i.e., it is derived with the aid of a predicting algorithm, such as machine learning-trained predictor.

In one embodiment, the total response is a based on affective response values such as emotional response values. For example, the total response is computed to be the difference between an emotional state of the user before and after being exposed to the token instances (e.g., the difference in the degree of excitement of the user before and after the exposure).

In one embodiment, the total response is based on values of a user measurement channel of the user. For example, the total response may be computed from physiological values of the user such as a heart rate or brainwave signals measured with EEG.

In one embodiment, the total response is proportional to difference between the responses of the user before and after the user was exposed to the token instances. For example, the response may be expressed as a change in the heart rate of the user as determined by heart rate measurements taken before and after the exposure to the token instances.

In one embodiment, computing the total response involves receiving a baseline value for the user's response. The computation of the total response due to the user's exposure to the token instances maybe done with adjustments with respect to the baseline value. For example, the user's total response may include a heart rate value which is the difference between heart rate measurements before and after exposure to token instances. This computation can also take into account the distance of values from the baseline value. Thus, for example, part of the difference between the measurement values before and after the exposure may be attributed to the heart rate returning to the baseline value.

In one embodiment, the response to the token instance of interest is the response of the user to the token instance of interest. For example, the response to the token instance of interest is derived from a total response that was based on measurements of the user or on a prediction made from a model of the user (e.g., the model was trained on training data that includes measurements of the user). Additionally or alternatively, the response to the token instance of interest may be considered a response of a general and/or representative user. For example, the response to the token instance of interest is derived from a total response is based on a prediction of a general model (trained mostly on data that does not involve the user).

In one embodiment, the representations of attention level are derived from a measurement channel of the user. For example, for visual token instances (e.g., images of objects), the representations of attention level may be derived from a camera and eye-tracking software that tracks the gaze of the user. Attention level of the user in a visual token instance (e.g., image of a dog) may be expressed as the proportion of time the user spends staring at the object.

In another embodiment, the representations of attention level are predicted based on the token instances. For example, for visual token instances, the representation of attention levels may be from algorithm that predicts levels of interest in objects and/or in regions of an image. Attention level of the user in a token instance may be expressed as the predicted level of interest in the token instance and/or the region in the visual field in which the token instance resides.

In one embodiment, multiple token instances of interest may be selected from among the received token instances. Optionally, less than half of the token instances are considered to be the token instances of interest. Optionally, at most one token instance at a time is considered to be the token instance of interest, i.e., token instances of interest do not have overlapping instantiation periods.

In one embodiment, estimating the response to the token instance of interest from the total response involves attributing a portion of the total response to the token instance of interest. In one example, more than 50% of the total response may be attributed to the response to the token instance of interest. Thus, if the total response is an increase of 10% to the heart rate, then the response to the token instance of interest is an increase of more than 5% to the heart rate. In another example, more than 90% of the total response is attributed to the response to the token instance of interest. In still another example, essentially all of the total response is attributed to the response to the token instance of interest, i.e., the response to the token instance of interest essentially equals the total response.

In one embodiment, estimating the response to the token instance of interest from the total response takes into consideration properties of the token instance of interest. For example, the portion of the total response that may be attributed to the token instance of interest may depend on properties such as the relative amount of time the user is exposed to the token instance of interest and/or the level of attention the user pays to the token instance of interest. Thus, if the user is exposed to the token instance of interest for a relatively short while, and/or the user pays relatively little attention to the token instance of interest, the estimated response to the token instance of interest may be relatively weak; for instance, only a small portion of the total response (e.g., 10%) is attributed to the response to the token instance of interest. However, if the user is exposed to the token instance for a relatively long time, and/or pays a lot of attention to the token instance of interest, the response attributed to the token instance of interest may be relatively higher, e.g., 90% of the total response.

Figure 3:
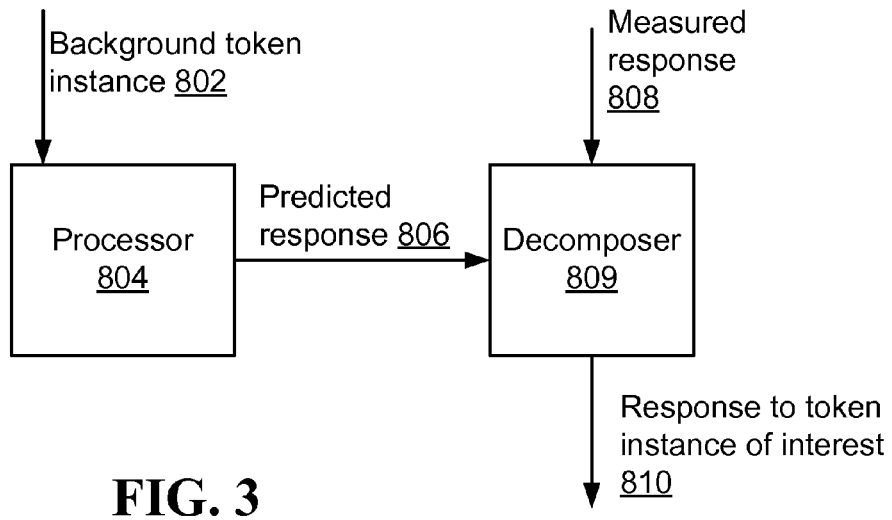
FIG. 3 illustrates a system that estimates a response to a token instance of interest from measurements and a predicted response to the background.

FIG. 3 illustrates one embodiment of a system configured to estimate a response of a user to a token instance of interest. The system includes at least a processor 804 and a decomposer 809. Optionally, the processor 804 and the decomposer are realized in the same device. Optionally, the processor 804 provides the functionality of the decomposer 809. For example, the decomposer 809 is realized via a program that runs on the processor 804.

The processor 804 is configured to receive a background token instance 802 to which the user was exposed. Optionally, the processor 804 may receive additional token instances. The processor 804 is also configured to predict a response 806 due to exposure to the background token instance. Optionally, the predicted response 806 is a response to being exposed to the background token instance 802 and possibly to other token instances that do not include the token instance of interest.

The decomposer 809 is configured to receive a measured response 808 of the user due to simultaneous exposure to both the background token instance 802 and the token instance of interest, and to estimate response of the user to the token instance of interest 810 based on the difference between the predicted response 806 and the measured response 808. For example, the predicted response 806 is subtracted from the measured response 808, and the difference is attributed to the response to the token instance of interest 810.

Figure 4:
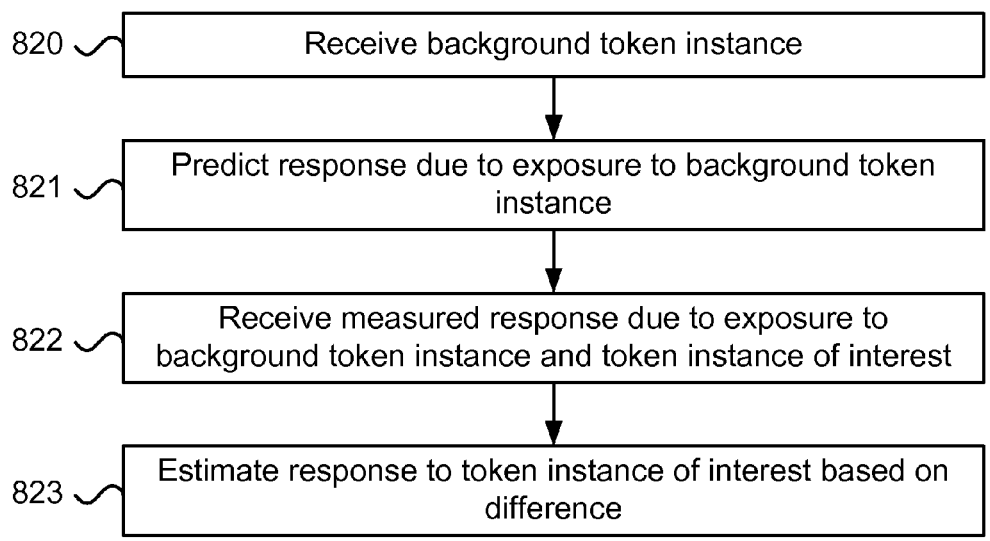
FIG. 4 illustrates a block diagram for estimating a response to a token instance of interest from measurements and a predicted response to the background.

FIG. 4 illustrates one embodiment of a method for estimating a user's response to a token instance of interest. The method includes the following steps:

In step 820, receiving token instances to which the user was exposed during a certain duration. The received token instances include a token instance that is considered a background token instance. Optionally, the token instances include multiple background token instances. Optionally, at least some of the background token instances have overlapping instantiation periods, i.e., there are times in which the user is exposed to more than one background token simultaneously.

In step 821, predicting response due to exposure to the background token instance. Optionally, predicting the response is done utilizing a machine learning-based predictor that is given an input that includes the background token instance or is derived, at least in part, from the background token instance. For example, the input to the predictor is a vector with a least one dimension whose value is set according to the background token instance.

In step 822, receiving a measured response of the user due to exposure to token instances comprising both the background token instance and the token instance of interest.

And in step 823, estimating response of the user to the token instance of interest based on difference between the predicted response and the measured response. For example, the predicted response is subtracted from the measured response, and the difference is attributed to the response to the token instance of interest.

Figure 5:
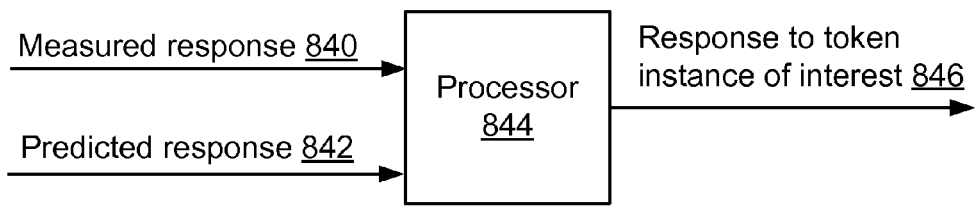
FIG. 5 illustrates a system in which a processor estimates a response to a token instance of interest from measurements and a received predicted response to the background.

FIG. 5 illustrates one embodiment of a system configured to estimate a response of a user to a token instance of interest. The system includes at least a processor 844.

The processor 844 is configured to receive a measured response 840 of the user due to exposure to token instances that include a background token instance and the token instance of interest. The processor 844 is also configured to receive a predicted response 842 due to exposure to the background token instance. From these inputs, the processor 844 is further configured to estimate the response of the user to the token instance of interest 846 based on the difference between the predicted response 842 and the measured response 840.

Figure 6:
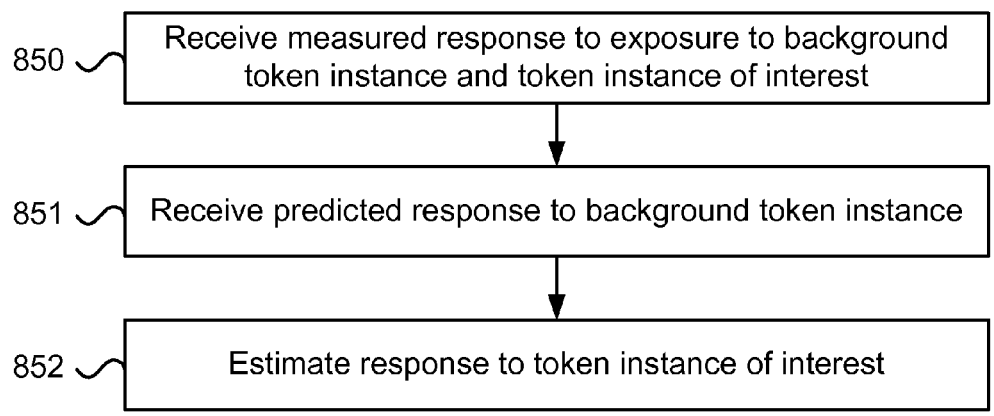
FIG. 6 illustrates a block diagram for estimating a response to a token instance of interest from measurements and a predicted response to the background and a received predicted response to the background.

FIG. 6 illustrates one embodiment of a method for estimating a user's response to a token instance of interest. The method includes the following steps:

In step 850, receiving a measured response of the user due to exposure to token instances comprising a background token instance and the token instance of interest. Optionally, the background token instance and the token instance of interest have overlapping instantiation periods, i.e., there are times in which the user is simultaneously exposed to both the token instance of interest and the background token instance.

In step 851, receiving a predicted response due to exposure to the background token instance. Optionally, the predicted response is obtained utilizing a machine learning-based predictor that is given an input that includes the background token instance or is derived, at least in part, from the background token instance. For example, the input to the predictor is a vector with a least one dimension whose value is set according to the background token instance.

And in step 852, estimating response of the user to the token instance of interest based on difference between the predicted response and the measured response. For example, the predicted response is subtracted from the measured response, and the difference is attributed to the response to the token instance of interest.

In one embodiment, a background token instance is a token instance that typically does not command user's attention to a large extent. During the time a user is exposed to a background token instance, the user is exposed to at least one more token instance (e.g., the token instance of interest) that is more likely to capture the user's attention than the background token instance. In one example, the token instance of interest is the main character in a video clip or game scene, and a background token instance may be a token instance corresponding to a minor characters appearing at the same time as the main character, a token instance corresponding to the background of the scene (e.g., the color of the room), and/or a token instance corresponding to the type of background music.

In one embodiment, a machine learning-based predictor is utilized to produce the predicted response. Optionally, the machine learning-based predictor is for the response of the user, e.g., the predictor is adapted to the user, such as being trained on training data that involves the user. Optionally, the machine learning-based predictor is trained on data collected over a long period, in which the user was in different situations. Optionally, values representing the predicted response of the user are given as an affective response in terms of values of a user measurement channel and/or changes to values of a user measurement channel. Optionally, values representing the predicted response of the user are given as an affective response, which may be an emotional state and/or a change to an emotional state.

In one embodiment, the measured response is derived from measurements of the user (e.g., taken with a sensor). Optionally, values representing the measured response of the user are given as an affective response in terms of values of a user measurement channel and/or changes to values of a user measurement channel. Optionally, values representing the measured response of the user are given as an affective response, which may be emotional state and/or change to an emotional state.

In one embodiment, the response to the token instance of interest is the response of the user to the token instance of interest. Additionally or alternatively, the response to the token instance of interest is considered a response of a general and/or representative user (e.g., the response is considered a generic response to the token instance of interest). Optionally, the response to the token instance of interest equals essentially the predicted response subtracted from the measured response.

In one embodiment, the background token instance belongs to a temporal window of token instances that is provided to the processor. The temporal window of token instances does not include the token instance of interest. The processor predicts the response by providing the temporal window of token instances to a machine learning-based predictor that predicts the response to the temporal window of token instances. Optionally, a collaborative filtering model for predicting the user's response to temporal windows of token instances is creating by using measured responses of other users to temporal windows of token instances. Optionally, the background token instance, and possibly other token instances that do not include the token instance of interest, are provided to a predictor that receives a stream of token instances as input.

In one example, the temporal window that includes the background token instance is generated by a video game graphics engine in which essentially all objects and characters are rendered, except for the lead character (operated by the user) and the lead virtual villain that the user's character must confront. The temporal window of token instances includes token instances extracted from the rendered by the video game. In another example, the temporal window of background token instances is generated by extracting token instances from a musical sequence without vocals or singing.

In one embodiment, the machine learning-based predictor for the user's response is trained on data collected over a long period, in which the user was in different situations. In another example, the machine learning-based predictor for the user's response is trained on samples including data of previous instantiations of token instances in order to create a habituation compensating machine learning-based predictor for the user's response due to the user's exposure to the background token instances.

In one embodiment, the predicted value of the user's response due to the user's exposure to the background token instance is calculated by selecting a machine learning-based predictor for the user's response appropriate to a situation the user is in from among at least two machine learning-based predictors for the user's response. Optionally, each of the machine learning-based predictors was trained on data collected from periods of time in which the user was in a situation belonging to a distinct set of situations specific to that machine learning-based predictor. Thus, the set of predictors comprises a set of situation-specific predictors, capable in some cases of producing more accurate situation-specific predictions.

In one embodiment, the predicted response levels are computed with respect to a received baseline value that is provided to the predictors as an additional input (e.g., a baseline value of a user measurement channel).

In one embodiment, the token instance of interest may be a token instance for which measured attention level of the user is highest. For example, of the visual token instances to which the user is exposed, the token instance of interest is the one that eye-tracking determines that the user spent the most timing looking at. Alternatively or additionally, the token instance of interest may be a token instance for which predicted attention level is the highest. For example, the token instance of interest may be one that a model predicts is most likely to cause a user to stare at.

In one embodiment, the response of a user to the token instance of interest is estimated based on the difference between the predicted response and the measured response. For example, the response to the token instance of interest essentially equals the difference between the value (e.g., heart rate) of the predicted response (which is a response to the background token instance), and the measured response (which is a response to both the background token instance and the token instance of interest). Optionally, the difference is computed by subtracting the value of the predicted response from the value of the measured response. Alternatively, the response to the token instance of interest may be proportional to the difference, and depend on properties related to the token instance of interest. For example, the portion of the difference that is attributed to the response to the token instance of interest may be proportional to how much attention the user pays to the token instance of interest, and/or how long the user is exposed to the token instance of interest; the more the user pays attention and/or the more the user is exposed, the larger the portion of the difference is attributed to the token instance of interest.

Figure 7:
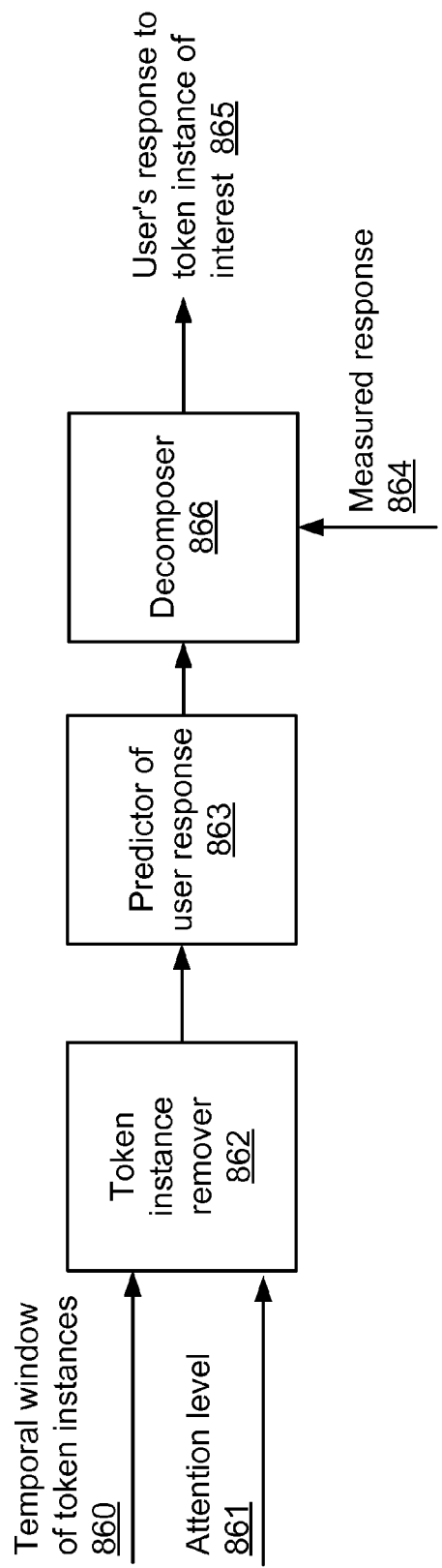
FIG. 7 illustrates a system that selects a token instance of interest to it and estimates the response to it utilizing a predicted response to the background.

FIG. 7 illustrates one embodiment of a system configured to estimate a response of a user to a token instance of interest. The system includes at least a token instance remover 862, a predictor of user response 863, and decomposer 866.

The token instance remover 862 is configured to receive a temporal window of token instances 860 and information regarding attention level 861. Optionally, the information regarding attention level 861 is the attention level of the user (e.g., as measured using eye-tracking). Additionally, or alternatively, the attention level 861 may be predicted from models. The attention level 861 provides information on the attention paid by the user to at least one of the token instances belonging to the window 860.

The token instance remover 862 is further configured to utilize the attention level 861 to select a token instance of interest from among the token instances belonging to the window, and remove the token instance of interest from the temporal window of token instances 860.

The predictor of user response 863 is configured to receive the temporal window of token instances from which the token instance of interest was removed and predict a response to being exposed to the temporal window of token instances without the token instance of interest.

The decomposer 866 is configured to receive a measured response 864 of the user due being exposed to the temporal window of token instances 860. The decomposer is further configured to estimate the user's response to the token instance of interest 865 based on the difference between the predicted response to being exposed to the temporal window of token instances without the token of interest and the measured response 864.

Figure 8:
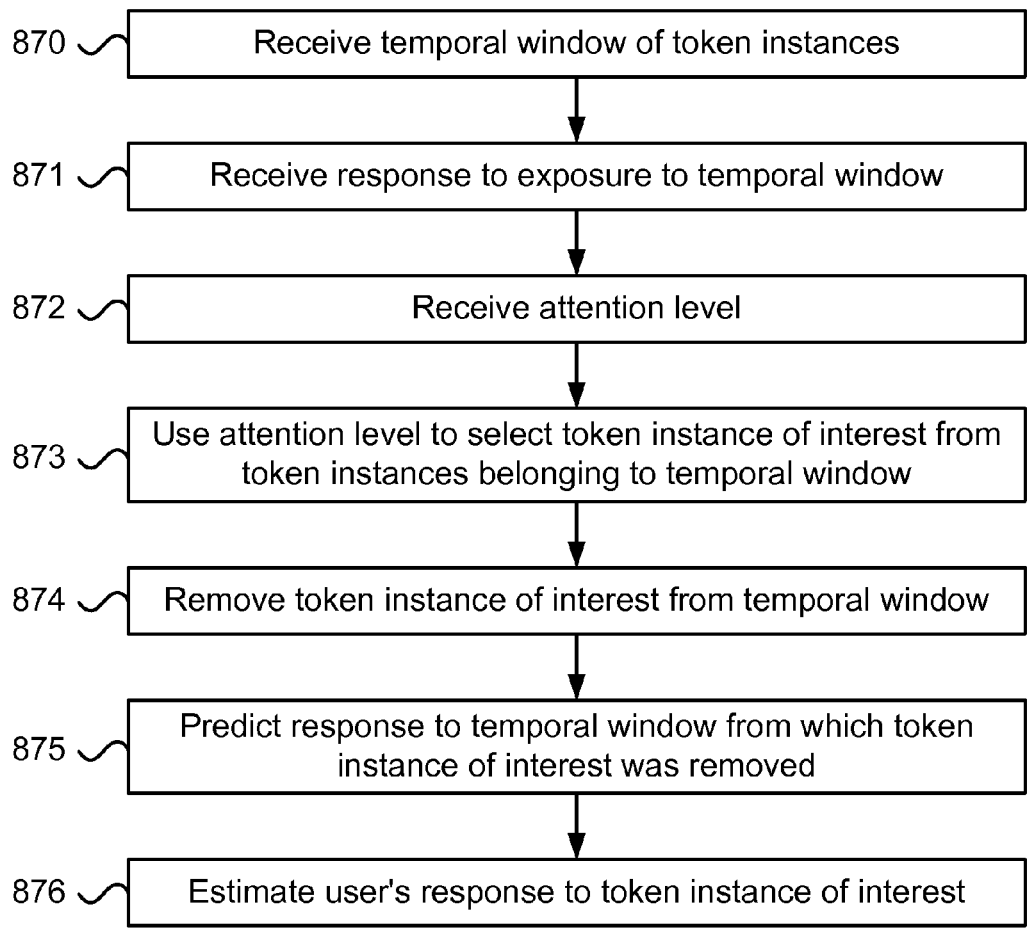
FIG. 8 illustrates a block diagram for selecting a token instance of interest and estimating the response to it utilizing a predicted response to the background.

FIG. 8 illustrates one embodiment of a method for estimating a response of a user e to a token instance of interest. The method includes the following steps:

In step 870, receiving a temporal window of token instances that includes a plurality of token instances, to which the user is exposed. At least two of the token instances have overlapping instantiation periods.

In step 871, receiving a measured response of the user due to the user being exposed to the temporal window of token instances (the window to which the user is exposed includes all the token instances).

In step 872, receiving attention level of the user in at least one of the token instances.

In step 873, using the attention level for selecting the token instance of interest from among the token instances. Optionally, most of the token instances are not of interest to the user, e.g., they are background token instances that are not considered to be the token instance of interest; less than a third of the token instances are considered to be of interest to the user.

In step 874, removing the token instance of interest from the temporal window of token instances. In step 875, predicting response of the user due to exposure to the temporal window of token instances from which the token instance of interest was removed.

And in step 876, estimating the response of the user to the token instance of interest from the difference between the predicted response and the measured response.

In one embodiment, a temporal window of token instances may be represented as a vector of feature values. In such a case, removing the token instance of interest from the temporal window of token instances may involve changing the value of features that correspond to the token instance of interest. For example, the token instance of interest may have features representing attributes such as the weight of the token instance of interest, the size of the token instance of interest, and/or the attention paid by the user to the token instance of interest. One or more of these values may be set to essentially zero in order to essentially remove the token instance of interest from the temporal window of token instances.

In another embodiment, a temporal window of token instances may be represented as a set of records corresponding to the token instances belonging to the window. In such a case, removing the token instance of interest from the temporal window of token instances may involve removing one or more record corresponding to the token instance of interest from the set of records.

In one embodiment, the attention level information is derived from a measurement channel of the user. For example, for visual token instances (e.g., images of objects), the attention level may be derived from a camera and eye-tracking software that tracks the gaze of the user. Alternatively or additionally, the attention level may be predicted based on the token instances. For example, for visual token instances, the representation of attention levels may be from algorithm that predicts levels of interest in objects and/or in regions of an image.

In one embodiment, a temporal window of token instances provided to a predictor in order to compute the user's response is created by using information regarding a user's observed and/or predicted attention level to one or more token instances. For example, if the temporal window of token instances provided to the predictor corresponds to a scene in a game or video, token instances corresponding to the main character may be deleted in order to create a temporal window of token instances describing the background of the scene. Optionally, the token instance with the highest user attention level is removed from the temporal window of token instances. Optionally, a fraction of the token instances is removed from the temporal window of token instances. For example, the token instances selected for removal comprise at most a third of all the token instances to which the user was exposed, and include the token instances to which the user paid the most attention.

In one embodiment, removing a token instance of interest from a temporal window of token instances comprises setting the value of one or more attribute values corresponding to the token instance of interest, such as weight, attention level, and/or size. Optionally, the attribute value is set to a very low value such as zero in order to indicate that the token instance has virtually no influence on the user. Optionally, removing a token instance of interest from a temporal window of token instances comprises removing all data records and/or fields corresponding to the token instance of interest from the data representation of the temporal window of token instances. In one example, a temporal window of token instances is represented as a list of records of the token instances to which the user is exposed, and the token instance of interest is removed from the list, producing a new shorter list of token instances.

In one embodiment, a machine learning-based predictor is utilized to produce the predicted response. Optionally, the machine learning-based predictor is for the response of the user, e.g., the predictor is adapted to the user, such as being trained on training data that involves the user. Optionally, the machine learning-based predictor is trained on data collected over a long period, in which the user was in different situations. Optionally, values representing the predicted response of the user are given as an affective response in terms of values of a user measurement channel and/or changes to values of a user measurement channel. Optionally, values representing the predicted response of the user are given as an affective response, which may be an emotional state and/or a change to an emotional state.

In one embodiment, the measured response is derived from measurements of the user (e.g., taken with a sensor). Optionally, values representing the measured response of the user are given as an affective response in terms of values of a user measurement channel and/or changes to values of a user measurement channel. Optionally, values representing the measured response of the user are given as an affective response, which may be emotional state and/or change to an emotional state.

In one embodiment, the response to the token instance of interest is the response of the user to the token instance of interest. Additionally or alternatively, the response to the token instance of interest is considered a response of a general and/or representative user (e.g., the response is considered a generic response to the token instance of interest). Optionally, the response to the token instance of interest equals essentially the predicted response subtracted from the measured response.

In one embodiment, the machine learning-based predictor for the user's response is trained on data collected over a long period, in which the user was in different situations. In another example, the machine learning-based predictor for the user's response is trained on samples including data of previous instantiations of token instances in order to create a habituation compensating machine learning-based predictor for the user's response due to the user's exposure to the background token instances.

In one embodiment, the predicted value of the user's response due to the user's exposure to the temporal window of token instances that does not include the token instance of interest is calculated by selecting a machine learning-based predictor for the user's response appropriate to a situation the user is in from among at least two machine learning-based predictors for the user's response. Optionally, each of the machine learning-based predictors was trained on data collected from periods of time in which the user was in a situation belonging to a distinct set of situations specific to that machine learning-based predictor. Thus, the set of predictors comprises a set of situation-specific predictors, capable in some cases of producing more accurate situation-specific predictions.

In one embodiment, the token instance of interest may be a token instance for which measured attention level of the user is highest. For example, of the visual token instances to which the user is exposed, the token instance of interest is the one that eye-tracking determines that the user spent the most timing looking at. Alternatively or additionally, the token instance of interest may be a token instance for which predicted attention level is the highest. For example, the token instance of interest may be one that a model predicts is most likely to cause a user to stare at it.

In one embodiment, the response of a user to the token instance of interest is estimated based on the difference between the predicted response and the measured response. For example, the response to the token instance of interest essentially equals the difference between the value (e.g., heart rate) of the predicted response (which is a response to the background token instance), and the measured response (which is a response to both the background token instance and the token instance of interest). Optionally, the difference is computed by subtracting the value of the predicted response from the value of the measured response. Alternatively, the response to the token instance of interest may be proportional to the difference, and depend on properties related to the token instance of interest. For example, the portion of the difference that is attributed to the response to the token instance of interest may be proportional to how much attention the user pays to the token instance of interest and/or how long the user is exposed to the token instance of interest; the more the user pays attention and/or the more the user is exposed, the larger the portion of the difference is attributed to the token instance of interest.

While interacting the physical and/or digital world, a user may experience similar events and/or stimuli multiple times (e.g., as characterized by the token instances the user is exposed to each time); such cases may be referred to as repetitive scenes. Repetitive scenes may have various variants, which may differ on some of the details (e.g., in each variant some of the token instances may be different and/or have different weights). However, the overall experience the user has in each variant of the repetitive scene is relatively similar. In one example, when playing the same computer game level multiple times (e.g., trying to clear a level), each time the level is played, the sequence of events or occurrences in game play is very similar; therefore, though there might be slight variations between each repetition of playing the level, the user's experience is quite similar (e.g., as defined via token instances to which the user is exposed each time). Thus, the different occurrences of playing the same level or screen in a computer game can be considered variants of a repetitive scene. In another example, multiple visits to a website (e.g., a news site, a virtual store, a social network), may be considered repetitive scenes. Since in each visit, the user may be exposed to similar content, a similar design of the site (fonts, color schemes, themes), and/or might have a similar interaction with the site. In yet another example, repeatingly touring the same region in a virtual world may be considered a repetitive scene. For example, each time the user walks down the main street of a virtual village, it may be considered a variant or a repetitive scene. Though in each visit, some details might be different (e.g., background music, the other characters that are present, and/or the events that are taking place), the overall experience of each virtual walk may be similar.

Since the user's experience in repetitive scenes is often quite similar, differences in the user's response (e.g., emotional response and/or change to values of measurement channels) may be attributed to the variations between the variants of the repetitive scenes. By identifying the differences between the variants, such as a token instance that appears in one variant but not in another, it is possible to gain understanding towards the user's response to the token instance.

Figure 9:
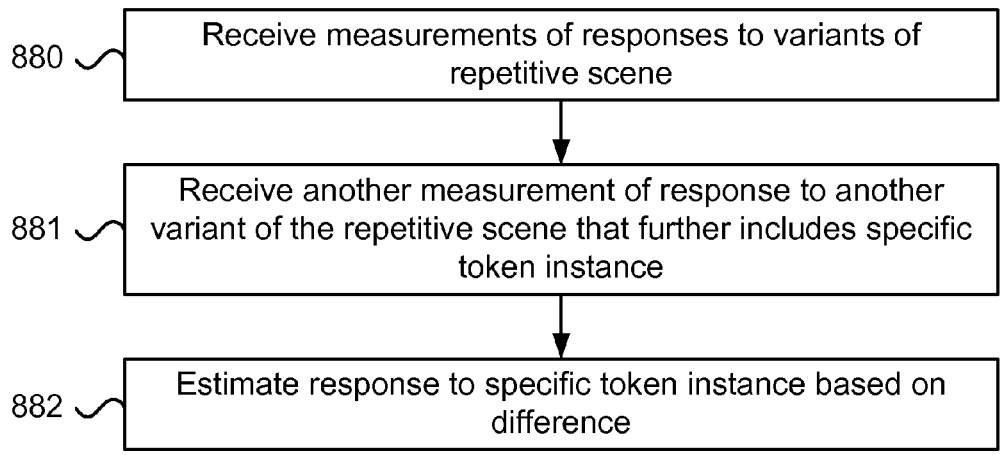
FIG. 9 illustrates a block diagram for estimating the response to a token instance that is added to a variant of a repetitive scene.

FIG. 9 illustrates one embodiment of a method for estimating a user's response to a specific token instance in a variant of a repetitive scene. The method includes the following steps:

In step 880, receiving measurements of responses taken at multiple exposures to variants of the repetitive scene. A specific token instance for which the user's response is estimated does not appear in the variants of repetitive scenes. For example, if the variants of the repetitive scenes may be described using temporal windows of token instances, the specific token instance is not included in the windows or has a weight of essentially zero in the windows.

In step 881, receiving another measurement of response of the user taken while the user is exposed to another variant of the repetitive scene that includes the specific token instance. Optionally, the another variant includes a token instance having an overlapping instantiation period with the specific token instance, i.e., at least during some time the user is exposed to the specific token instance the user is also simultaneously exposed to another token instance.

And in step 882, estimating the response of the user to the specific token instance based on difference between the other measurement and a representation of the measurements.

Figure 10:
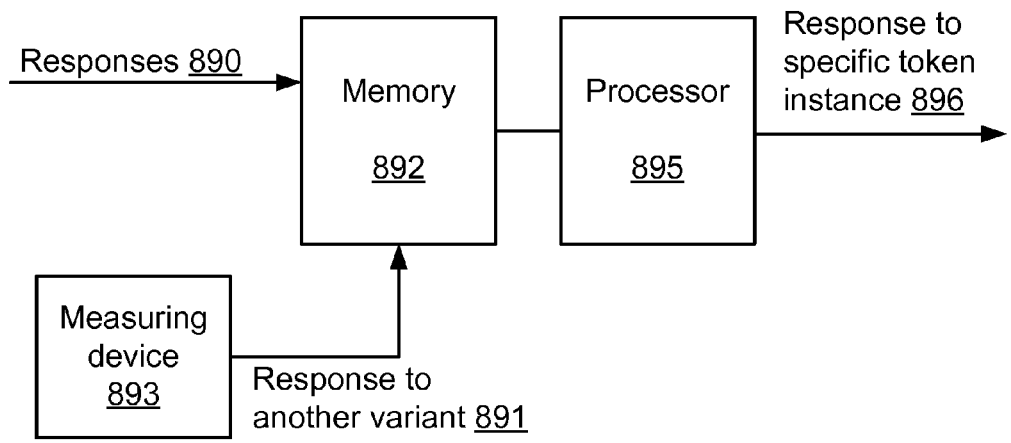
FIG. 10 illustrates a system that estimates the response to a token instance that is added to a variant of a repetitive scene.

FIG. 10 illustrates one embodiment of a system configured to estimate a response of a user to a specific token in a repetitive scene. The system includes at least a memory 892 and a processor 895.

The memory 890 is configured to receive measurements of responses taken at multiple exposures to variants of the repetitive scene. The specific token instance for which the user's response is estimated does not appear in the variants of repetitive scenes. For example, if the variants of the repetitive scenes may be described using temporal windows of token instances, the specific token instance is not included in said windows or has a weight of essentially zero in those windows. The memory 890 is further configured to receive, from a measuring device 893, another measurement of a response 891 of the user taken while the user is exposed to another variant of the repetitive scene that includes the specific token instance. Optionally, the another variant includes a token instance having an overlapping instantiation period with the specific token instance, i.e., at least during some time the user is exposed to the specific token instance the user is also simultaneously exposed to another token instance.

The processor 895 is configured to estimate the response of the user to the specific token instance based on difference between the other measurement and a representation of the measurements.

In one example, the method for estimating a user's response to a specific token instance in a variant of a repetitive scene characterizes the user's response to token instances in domains like video games and virtual worlds, since in such domains measurements of the user may be taken multiple times while experiencing essentially the same repetitive scenes/missions. In addition, since the content in such domains is generally created by computational processes, exact knowledge of which elements are present in each scene is easily obtainable, thus making it possible to accurately identify differences between various variants of a repetitive scene. By coupling accurate knowledge of the difference between scenes with measurements of the user's response, the user's response to specific added token instances might be deduced.

In one embodiment, the representation of the measurements is given as a measurement value, and the response of the user to the specific token instance is obtained by essentially subtracting the value of the representation of the measurements from the other measurement.

Determining whether two scenes are variants of a repetitive scene may be done in various ways:

1) Two variants may be considered variants of a repetitive scene if a certain portion of the token instances of both variants is the same.

In one embodiment, variants of scenes are represented by token instances, and two variants may be considered variants of a repetitive scene if at least 50% of their token instances are essentially the same. For example, when each variant is represented as a temporal window of token instances, at least 50% of the token instances in the first variant also appear in the second variant. Alternatively or additionally, the weight that is assigned to the token instances belonging to the first variant that also belong to the second variant is at least 50% of the weight assigned to token instances belonging to each variant.

2) Two variants may be considered variants of a repetitive scene if an ordinary person is likely to declare that both variants are similar and are essentially two variants of a repetitive scene. For example, an experiment is conducted in which a number of people are asked whether the two variants are similar. The proportion of peoples that answer that the two are variants of a repetitive scene may be interpreted as the probability that the two are variants of the repetitive scene.

In one embodiment, two variants are considered variants of a repetitive scene if there is a probability of at least 20% that an ordinary user exposed to the two variants reports that the two are variants of a repetitive scene. Alternatively, a higher threshold may be used: In one embodiment, two variants are considered variants of a repetitive scene if there is a probability of at least 80% that an ordinary user exposed to the two variants reports that the two are variants of a repetitive scene.

3) Two variants are considered variants of a repetitive scene if low-level features derived from the two variants are similar. Low-level features are typically concerned with general characteristics of the scene and not specific details. For example, low-level features of images may include features that are typically statistical in nature, such as average color, color moments, contrast-type textural feature, and edge histogram and Fourier transform based shape features. In another example, low-level auditory features may involve statistics regarding the beat, tempo, pitch, and/or sound energy.

In one embodiment, two variants are considered variants of a repetitive scene if vectors containing the values of the low-level features of each variant are similar. For example, the vectors of the two variants of a normalized dot product of at least 0.3 (i.e., the cosine of the angle between the two vectors is at least 0.3).

In one embodiment, the representation of the measurements is essentially an average of the measurements of the responses taken at multiple exposures to the variants of the repetitive scene.

In one embodiment, the representation of the measurements is calculated based on the measurements of responses utilizing a predefined formula. For example, the representation of the measurements may be a weighted average assigning a higher weight to measurements corresponding to variants to which the user was exposed to at later times (which are more likely to represent the user's current response to the repetitive scene). In another example, the representation of measurements may be computed by assigning a higher weight to variants for which there is evidence that the user was paying attention to the scene (e.g., by analyzing results of eye-tracking of the user during the exposure).

In one embodiment, variants of the repetitive scene are stored as temporal windows of token instances, which are used to create training samples. In addition, the responses to the variants, e.g., as determined from affective response measurements, are also stored and used as target values for the training sample. The training samples and target values are utilized to train a model for response of the user to variants of the repetitive scene. Optionally, the training is performed on the processor 895. Alternatively, the training is performed on a different processor.

In one embodiment, the representation of the measurements is obtained by providing the prediction model with a temporal windows of token instances corresponding to the variants of the repetitive scene, which does not include the specific token instance. Thus the representation of the measurements may be determined without the need for receiving measurements of the user corresponding to the exposure to the variants of the repetitive scene.

In one embodiment, the specific token instance included in the variant of the repetitive scene does not significantly alter the essence of the repetitive scene compared to the other variants of the repetitive scene that do not include the specific token instance. For example, the specific token instance maybe related to the background of an event occurring in the scene or to a minor character. Thus if the specific token is removed or changed, it does not alter what is happening in the scene in a significant way.

In one embodiment, the other measurement is derived from multiple measurements of response of the user taken while the user was exposed to variants of the repetitive scene that include the specific token instance. For example, the other measurement may be an average value obtained from measurements of variants of the repetitive scene that include the specific token instance. Optionally, the measurements are weighted according to the weight of the specific token instance in each variant.

In one embodiment, the repetitive scene is generated by a computer game, and the specific token instance included in the repetitive scene does not significantly alter the game's plot compared to the other variants of the repetitive scene that do not include the specific token instance. For example, the specific token instance may relate to the background music, a specific sound effect, visual effect (e.g., extent of explosion), and/or a minor character with which the user does not significantly interact.

In one embodiment, the measurements of responses taken at multiple exposures to variants of the repetitive scene are measurements of responses of the user taken at multiple exposures of the user to variants of the repetitive scene. Alternatively, most of the measurements of responses taken at multiple exposures to variants of the repetitive scene are measurements of responses of other users.

Figure 11:
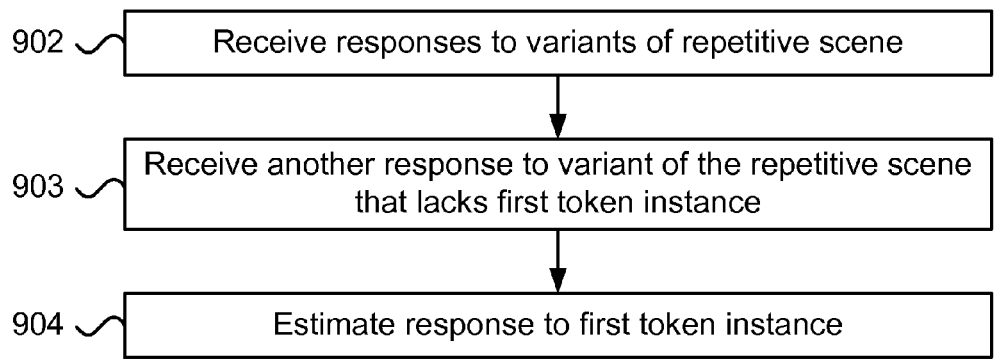
FIG. 11 illustrates a block diagram for estimating the response to a token instance in a repetitive scene by utilizing the response to a variant of the scene that lacks the token instance.

FIG. 11 illustrates one embodiment of a method for estimating a response of a user to a first token instance in a repetitive scene. The method includes the following steps:

In step 902, receiving measurements of responses taken at multiple exposures to variants of the repetitive scene comprising the first token instance and a second token instance.

In step 903, receiving another measurement of response of the user taken while the user is exposed to another variant of the repetitive scene that lacks the first token instance that appeared in the repetitive scenes corresponding to the measurements. Optionally, the first token instance and the second token instance have overlapping instantiations periods, i.e., there is a time in which the user is simultaneously exposed to both the first and the second token instances.

And in step 904, estimating the response of the user to the first token instance based on difference between the other measurement and a representation of the measurements.

Figure 12:
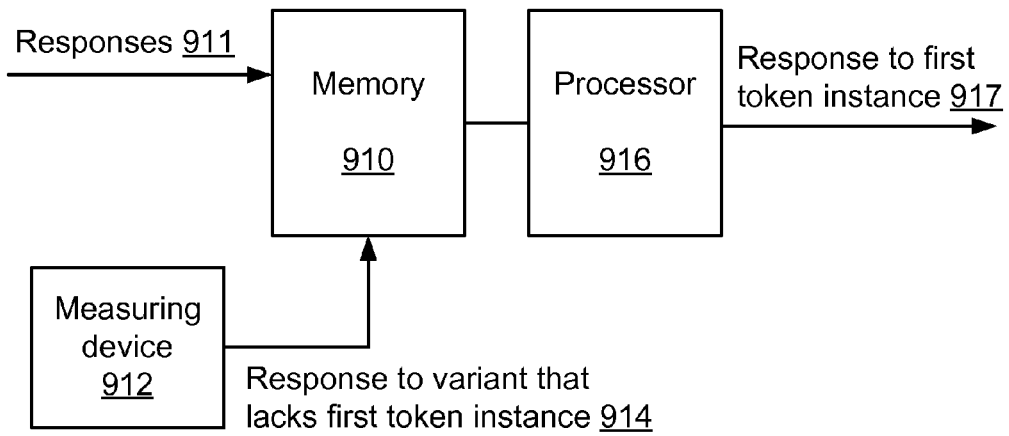
FIG. 12 illustrates a system that estimates the response to a token instance in a repetitive scene by utilizing the response to a variant of the scene that lacks the token instance.

FIG. 12 illustrates one embodiment of a system configured to estimate a response of a user to a first token instance in a repetitive scene. The system includes at least a memory 910 and a processor 916.

The memory 910 is configured to receive measurements of responses taken at multiple exposures to variants of the repetitive scene. For example, the measurements may be affective response measurements of the user taken with a sensor.

The memory 910 is further configured to receive, from a measuring device 912, another measurement of a response 914 of the user taken while the user is exposed to another variant of the repetitive scene that lacks the first token instance.

The processor 916 is configured to estimate the response of the user to the specific token instance based on difference between the other measurement and a representation of the measurements.

In one embodiment, the representation of the measurements is given as a measurement value, and the response of the user to the first token instance is obtained by essentially subtracting the value of the other measurement from the representation of the measurements.

Determining whether two scenes are variants of a repetitive scene may be done in various ways:

1) Two variants may be considered variants of a repetitive scene if a certain portion of the token instances of both variants is the same.

In one embodiment, variants of scenes are represented by token instances, and two variants may be considered variants of a repetitive scene if at least 50% of their token instances are essentially the same. For example, when each variant is represented as a temporal window of token instances, at least 50% of the token instances in the first variant also appear in the second variant. Alternatively or additionally, the weight that is assigned to the token instances belonging to the first variant that also belong to the second variant is at least 50% of the weight assigned to token instances belonging to each variant.

2) Two variants may be considered variants of a repetitive scene if an ordinary person is likely to declare that both variants are similar and are essentially two variants of a repetitive scene. For example, an experiment is conducted in which a number of people are asked whether the two variants are similar. The proportion of peoples that answer that the two are variants of a repetitive scene may be interpreted as the probability that the two are variants of the repetitive scene.

In one embodiment, two variants are considered variants of a repetitive scene if there is a probability of at least 20% that an ordinary user exposed to the two variants reports that the two are variants of a repetitive scene. Alternatively, a higher threshold may be used: In one embodiment, two variants are considered variants of a repetitive scene if there is a probability of at least 80% that an ordinary user exposed to the two variants reports that the two are variants of a repetitive scene.

3) Two variants are considered variants of a repetitive scene if low-level features derived from the two variants are similar. Low-level features are typically concerned with general characteristics of the scene and not specific details. For example, low-level features of images may include features that are typically statistical in nature, such as average color, color moments, contrast-type textural feature, and edge histogram and Fourier transform based shape features. In another example, low-level auditory features may involve statistics regarding the beat, tempo, pitch, and/or sound energy.

In one embodiment, two variants are considered variants of a repetitive scene if vectors containing the values of the low-level features of each variant are similar. For example, the vectors of the two variants of a normalized dot product of at least 0.3 (i.e., the cosine of the angle between the two vectors is at least 0.3).

In one embodiment, the representation of the measurements is essentially an average of the measurements of the responses taken at multiple exposures to the variants of the repetitive scene.

In one embodiment, the representation of the measurements is calculated based on the measurements of responses utilizing a predefined formula. For example, the representation of the measurements may be a weighted average assigning a higher weight to measurements corresponding to variants to which the user was exposed to at later times (which are more likely to represent the user's current response to the repetitive scene). In another example, the representation of measurements may be computed by assigning a higher weight to variants for which there is evidence that the user was paying attention to the scene (e.g., by analyzing results of eye-tracking of the user during the exposure).

In one embodiment, variants of the repetitive scene are stored as temporal windows of token instances, which are used to create training samples. In addition, the responses to the variants, e.g., as determined from affective response measurements, are also stored and used as target values for the training sample. The training samples and target values are utilized to train a model for response of the user to variants of the repetitive scene. Optionally, the training is performed on the processor 916. Alternatively, the training is performed on a different processor.

In one embodiment, the representation of the measurements is obtained by providing the prediction model with a temporal window of token instances corresponding to the variants of the repetitive scene, which does not include the first token instance. Thus, the representation of the measurements may be determined without the need for receiving measurements of the user corresponding to the exposure to the variants of the repetitive scene.

In one embodiment, the first token instance lacking from the variant of the repetitive scene does not significantly alter the essence of the repetitive scene compared to the other variants of the repetitive scene that do not lack the first token instance. For example, the first token instance maybe related to the background of an event occurring in the scene or to a minor character. Thus if the first token is removed or changed, it does not alter what is happening in the scene in a significant way.

In one embodiment, the other measurement is derived from multiple measurements of response of the user taken while the user was exposed to variants of the repetitive scene that lack the first token instance. For example, the other measurement may be an average value obtained from measurements of variants of the repetitive scene that lack the first token instance.

In one embodiment, the measurements of responses taken at multiple exposures to variants of the repetitive scene are measurements of responses of the user taken at multiple exposures of the user to variants of the repetitive scene. Alternatively, most of the measurements of responses taken at multiple exposures to variants of the repetitive scene are measurements of responses of other users.

Computing Affective Responses

As used herein, the term response, when used to refer to the response of the user (e.g., the response of the user to a token instance), refers to an affective response, which may be measured and/or predicted. Similarly, as used herein terms like "total response" refers to a total affective response.

In one embodiment, response such as a measured response or a predicted response are expressed as an absolute value. For example, a response may be an increase of 5 beats per minute to the heart rate or an increase of 2 points on a scale of arousal. Alternatively or additionally, a response may be expressed as a ratio (compared to an initial or baseline value). For example, the total response to being exposed to token instances may be an increase of 10% to the heart rate compared to a measurement taken before the exposure to token instances. Alternatively or additionally, a response may be expressed as relative or qualitative change. For example, a response may be paraphrased as the user being slightly happier than his/her original state.

In one embodiment, the response of the user to being exposed to token instances, e.g., a measured response or a predicted response, may be computed by comparing an early response of with a response of the user corresponding to a later time. For example, the early response may correspond to the beginning of the exposure, while the later response may correspond to the end of the exposure. Optionally, the response is obtained by subtracting the early response from the later response. Optionally, the total response is obtained by computing the ration between the later response and the early response (e.g., by dividing a value of the later response by a value of the early response).

In one example, the total response may be expressed as a change in the user's heart rate; it may be computed by subtracting a first heart rate value from a later second heart rate value, where the first value is taken in temporal proximity the beginning of the user's exposure to the received token instances while the later second value is taken in temporal proximity to the end of the user's exposure to the received token instances. In another example, the total response to the token instances is computed by comparing emotional states corresponding to the beginning and the end of the exposure to the token instances. For example, the total response may be the relative difference in the level of happiness and/or excitement that the user is evaluated to be in (e.g., computed by dividing the level after the exposure to the token instances by the level before the exposure to the token instances).

Herein, temporal proximity refers to closeness in time. Two events that occur in temporal proximity occur at times close to each other. For example, measurements of the user used that are taken at temporal proximity to the beginning of the exposure of the user to the token instances, may be taken a few seconds before and/or possibly a few seconds after the beginning of the exposure (some measurement channels such as GSR or skin temperature may change relatively slowly compared to fast changing measurement channel such as EEG). Similarly, measurements of the user that are taken at temporal proximity to the beginning of the exposure of the user to the token instances may be taken a few seconds before and/or possibly a few seconds after the beginning of the exposure.

In one embodiment, responses used to compute the measured or predicted response to token instances may be a product of a single value. For example, a response corresponding to before the exposure to the token instances may be a measurement value such as a single GSR measurement taken before the exposure. Alternatively, responses used to compute the measured or predicted response to token instances may be a product of may be a product of multiple values. For example, a response may be average of user channel measurement values (e.g., heart rate, GSR) taken during the exposure to the token instances. In another example, a response is a weighted average of values; for instance, user measurement values used to derive the response may be weighted according to the attention of the user as measured at when the user measurements were taken.

In one embodiment, the response of the user to the token instances to which the user is exposed is computed by comparing a response of the user with a baseline value. Optionally, the baseline value may be computed from measurements (e.g., the user's resting heart rate as computed over several hours). Additionally or alternatively, the baseline value may be predicted such as a machine learning-trained model. For example, such a model may be used to predict that in a certain situation such as playing a computer game, the user is typically mildly excited. Optionally, the response may be computed by subtracting a baseline value from the measured response to being exposed to token instances.

In one embodiment, computing a response involves receiving a baseline value for the user. The computation of the user's response maybe be done with adjustments with respect to the baseline value. For example, the user's response may be described as a degree of excitement that is the difference between how excited the user was before and after being exposed to the token instance. This computation can also take into account the distance of values from the baseline value. Thus, for example, if before the exposure to the token instances, the user was in an over-excited state (much above the baseline), and after the exposure the user's excitement level was only slightly above the base line, part of the decline may be attributed to the user's natural return to a baseline level of excitement.

In one embodiment, the response of the user to a certain token instance (e.g., a token instance of interest) is estimated according to the difference between two values, such as two measured responses, a measured response and a representation of measurements, and/or a measured response and a predicted response. Optionally, the difference is obtained by subtracting one of the values from the other (e.g. subtracting the value of a measured response from the representation of measurements). Optionally, the difference may be obtained using a distance function. For example, the difference between response values expressed as multi-dimensional points may be given according to the Euclidean distance between the points. Additionally or alternatively, the difference between two multi-dimensional values may be expressed as a vector between the points representing the values.

In one embodiment, the estimated response to the certain token instance may be derived from the value of the difference in addition to one or more normalizations and/or adjustments according to various factors.

In one example, estimating the response of the user to the certain token instance of interest takes into account the response that was determined for other users. Optionally, the other users have similar responses to the user (e.g., they respond to many token instances in the same way). Thus, if in some cases, the user's response is significantly different from the response other users have to the certain token instance, the user's response may be normalized and set to be closer to the other users' response (e.g., by setting the user's response to be the average of the other users' response and the user's originally estimated response).

In another example, estimating the response of the user to the certain token instance may take into account a baseline value for the user. If the user's initial state before being exposed to the certain token instances is different from a received baseline value, then the estimated response may be corrected in order to account for a natural return to the baseline. For example, if the user's response is described via a physiological measurement such as a change to the heart rate, estimating the response to the certain token instance needs to take into account the rate at which the user's heart rate returns to the baseline value (which may happen within tens of seconds to a few minutes). Thus, for example an initial estimate of the response may show that the response to the certain token instance was not substantial (e.g., there was very little change to the heart rate). However, if the user was unexcited to begin with, then over the time the user's heart rate should decrease to return to the baseline. However, if the heart rate did not return to the baseline at the expected rate, this can be attributed, at least in part, to the user's response to the certain token instance; thus the estimation of the response may be amended in this case (e.g., by increasing the value of the estimated response to account for the tendency to return to the baseline value).

In still another example, estimating the response of the user to the certain token instance may take into account information regarding the other token instances the user was exposed at the time. In some cases, the user's attention may be focused on a single token instance or small number of token instances at any given time (e.g., if the user is looking at details in an image). If there are many token instances to which the user is exposed simultaneously, this can lead to saturation, in which due to the sensory overload, the user's response to individual token instances may be diminished. Thus, estimating the user's response to the certain token instance may take into account corrections due to saturation. For example, if the user is exposed to many token instances at the same time, the original estimate of the response may be increase to compensate for the fact that there were many token instances competing for the user's attention that may have distracted the user from the certain token instance.

Token Instances of Interest

In one embodiment, the attention level values representing the user's attention in token instances are derived from a measurement channel of the user. For example, the attention levels are determined using video cameras, motion sensors, and/or eye-tracker to determine which images the user was looking at and how long the user looked at each image. Optionally, the attention level assigned to token instances corresponding to the images may be proportional to the time the user spent looking at each image. Additionally or alternatively, the attention level assigned to token instances corresponding to images may be determined using algorithms for prediction of interest and/or saliency in images and/or video sequences. Additionally or alternatively, the attention levels assigned to token instances may be computed using heuristics, for example, by assigning a high predicted attention level to token instances corresponding to large images of talking characters (which may be determined by algorithms for face recognition and detection of movement of the lips), and assigning low attention levels to token instances corresponding to inanimate objects that are not in the center of the frame.

In one embodiment, a token instance of interest is selected using attention level information corresponding to one or more of the token instances to which the user was exposed. Optionally, the attention level data is derived from measurements, such as user measurement channels. For example, attention level in some token instances may be computed using eye tracking, movement sensors, and/or pressure sensors. Optionally, the attention level data is derived using models and/or algorithms for predicting the user's attention level in some of the tokens.

In one embodiment, at some times at most one token instance is selected as a token instance of interest. In one example, the token instance for which the user's predicted and/or measured attention level had a maximal value compared to the other token instances to which the user was exposed at the corresponding time. In another example, the token instance of interest is chosen to be the token instance for which the user's integrated sum of attention levels is highest, compared to the other token instances of interest the user was exposed to during the corresponding time period.

In one embodiment, various proportions of the total response may be attributed to the user's response to the token instance of interest. For example, 50% of the total response is attributed to the response to the token instance of interest. Optionally, most of the total response may be attributed to the token instances of interest. For example, 90% of the total response is attributed to the token instance of interest. In another example, essentially the entire total response is attributed to the user's response to the token instance of interest.

In one embodiment, at some times, multiple token instances may be chosen to be token instances of interest. Optionally, token instances of interest may have overlapping periods of instantiation (i.e., there are times in which the user was simultaneously exposed to two or more token). Optionally, only a portion of token instances are considered token instances of interest. For example, less than half of the token instances are considered to be token instances of interest.

In one embodiment, token instances of interest may be selected according to various criteria. In one example, a certain number of token instances for which the user's predicted and/or measured attention levels were highest are selected to be token instances of interest. In another example, token instances for which the user's predicted and/or measured attention levels exceed a certain threshold are selected to be token instances of interest. In still yet another example, essentially all token instances are considered token instances of interest.

In cases in which there are multiple token instances of interest, the total response may be attributed to individual token instances of interest in different ways. For example, an equal proportion of the total response is attributed to each token instance of interest. In another example, the response to a token instance of interest is proportional to the attention level corresponding to the token instance.

User Measurements

In one embodiment, values from a user's user measurement channels are collected by using one or more sensors and/or measurement devices that may be attached to the body, clothing (e.g., gloves, shirts, helmets), implanted in the user's body, and/or remote sensors external to the user's body (e.g., camera, microphone).

In some embodiments, the duration in which the sensor operates in order to measure the user's affective response may differ depending on one or more of the following: (i) the type of content the user is exposed to, (ii) the type of physiological and/or behavioral signal being measured, and (iii) the type of sensor utilized for the measurement. In some cases, the user's affective response to token instances may be measured by the sensor substantially continually throughout the period in which the user is exposed to the token instances. However, in other cases, the duration during which the user's affective response to the token instances is measured need not necessarily overlap, or be entirely contained in the time in which the user is exposed to the token instances.

With some physiological signals, there is an inherent delay between the time in which a stimulus occurs and changes the user's emotional state, and the time in which the corresponding affective response is observed via a change in the physiological signal's measurement values. For example, an affective response comprising changes in skin temperature may take several seconds to be detected by a sensor. In addition, some physiological signals may depart very rapidly from baseline values, but take much longer to return to the baseline values.

In some cases, the physiological signal might change quickly as a result of a stimulus, but returning to the pervious baseline value (from before the stimulus), may take much longer. For example, the heart rate of a person viewing a movie in which there is a startling event may increase dramatically within a second; however, it can take tens of seconds and even minutes for the person to calm down and for the heart rate return to a baseline level.

The lag in time it takes affective response to be manifested in certain physiological and/or behavioral signals can lead to it that the period in which the affective response is measured occurs after the exposure to the content. Thus, in some embodiments, measuring the affective response of the user to the token instances may end, and possibly even start, essentially after the user is exposed to the token instances. For example, measuring the user's response to a surprising short scene in a video clip (e.g., a gunshot lasting a second), may involve taking a GSR measurement a couple of seconds after the gunshot was played to the user. In another example, the user's affective response to playing a level in a computer game may include taking heart rate measurements lasting even minutes after the game play is completed.

In some embodiments, determining the user's affective response to the token instances may utilize measurement values corresponding to a fraction of the time the user was exposed to the token instances. The user's affective response to the token instances may be measured by obtaining values of a physiological signal that is slow to change, such as skin temperature, and/or slow to return to baseline values, such as heart rate. In such cases, measuring the user's affective response to token instances does not have to involve continually measuring the user throughout the duration in which the user is exposed to the token instances. Since such physiological signals are slow to change, reasonably accurate conclusions regarding the user's affective response to the token instances may be reached from samples of intermittent measurements taken at certain periods during the exposure (the values corresponding to times that are not included in the samples can be substantially extrapolated). In one example, measuring the user's affective response to playing a computer game involves taking measurements during short intervals spaced throughout the user's exposure, such as taking a GSR measurement lasting two seconds, every ten seconds. In another example measuring the user's response to a video clip with a GSR, heart rate and/or skin temperature sensor may involve operating the sensor mostly during certain portions of the video clip, such as a ten-second period towards the end of the clip.

In some embodiments, determining the user's affective response to the token instances may involve measuring a physiological and/or behavioral signal of the user before and/ or after the user is exposed to the token instances. Optionally, this is done in order to establish a baseline value for the signal to which measurement values of the user taken during the exposure to the token instances, and/or shortly after the exposure, can be compared. For example, the user's heart rate may be measured intermittently throughout the duration, of possibly several hours, in which the user plays a multi-player game. The values of these measurements are used to determine a baseline value to which measurements taken during a short battle in the game can be compared in order to compute the user's affective response to the battle. In another example, the user's brainwave activity is measured a few seconds before displaying an exciting video clip and also while the clip is played to the user. Both sets of values, the ones measured during the playing of the clip and the ones measured before it, are compared in order to compute the user's affective response to the clip.

In one embodiment, some values of the user measurement channels are stored in a database as time series with short durations between consecutive measurement points. Optionally, the user's measurement channels are stored at different temporal resolutions, i.e., the typical difference in time between consecutive entries in the database may vary between measurement channels. Optionally, the temporal resolution of the same channel may vary at different points in database, for example, regions where low complexity in the measurement values is detected and/or regions with noisy measurements may be stored with lower temporal resolution, i.e., longer intervals between values. Optionally, the system supports queries that provide the values of the user measurements at a required time, for instance by interpolating and/or extrapolating values from the stored measurements at different times.

In one embodiment, the user measurement data may be processed and/or normalized in many ways, before, during and/or after the data is stored. In one example, the values of some of the measurements are scaled to be in the range $[-1,+1]$. In another example, the values of some of the measurements are normalized to z-values, which bring the mean of the values recorded for the modality to 0, with a variance of 1. In yet another example, some user measurements may be processed and/or converted to analyzable features in several ways. For instance, through extracting statistics for the values of each measurement channel in a predefined window size, such as the minimum, maximum, and/or various moments of the distribution, such as the mean, variance, or skewness. In still another example, user measurements are subjected to feature extraction and/or reduction techniques, such as Fisher projections, Principal Component Analysis (PCA), and/or feature selection techniques like Sequential Forward Selection (SFS) or Sequential Backward Selection (SBS). In still another example, some of the images and video images may be processed using various detection algorithms for identifying cues like movement, smiling, laughter, concentration, facial expressions and/or microexpressions (for example, by human facial expressions taxonomy such as "Facial Action Coding System" by Paul Ekman), body posture, body language, gaze. Images may also be processed with algorithms for detecting and describing local features such as Scale-Invariant Feature Transform (SIFT), Speeded Up Robust Features (SURF), and/or scale-space representation. In still another example, body movements (e.g., using motion sensors), and/or audio samples (e.g., using microphone) may be measured and processed to identify cues like attitude, attention, affective response, and/or satisfaction. In still another example, auditory and/or written data are processed using speech analysis and/or semantic analysis methods.

Some embodiments may utilize known and to be discovered methods for pre-processing user measurement data and extracting features from the measured data. For example: (i) a variety of physiological measurements may be preprocessed according to the methods and references listed in van Broek, E. L., Janssen, J. H., Zwaag, M. D., D. M. Westerink, J. H., & Healey, J. A. (2009), Prerequisites for Affective Signal Processing (ASP), In Proceedings of the International Joint Conference on Biomedical Engineering Systems and Technologies, INSTICC Press, incorporated herein by reference; (ii) a variety of acoustic and physiological signals may be pre-processed and have features extracted from them according to the methods described in the references cited in Tables 2 and 4, Gunes, H., & Pantic, M. (2010), Automatic, Dimensional and Continuous Emotion Recognition, International Journal of Synthetic Emotions, 1 (1), 68-99, incorporated herein by reference; (iii) Pre-processing of Audio and visual signals may be performed according to the methods described in the references cited in Tables 2-4 in Zeng, Z., Pantic, M., Roisman, G., & Huang, T. (2009), A survey of affect recognition methods: audio, visual, and spontaneous expressions, IEEE Transactions on Pattern Analysis and Machine Intelligence, 31 (1), 39-58, incorporated herein by reference; and (iv) pre-processing and feature extraction of various data sources such as images, physiological measurements, voice recordings, and text based-features, may be performed according to the methods described in the references cited in Tables 1, 2, 3, 5 in Calvo, R. A., & D'Mello, S. (2010). Affect Detection: An Interdisciplinary Review of Models, Methods, and Their Applications. IEEE Transactions on affective computing 1(1), 18-37, incorporated herein by reference.

Tokens

In one embodiment, the system extracts, receives, and/or accesses a stream of token instances. The token instances may be annotated using any appropriate manual, semi-automatic, and/or automated techniques. For example, manual token labeling may be achieved using manual annotation or marking. In another example, the token labeling is partially automated using algorithms to segment media into scenes, or segment and/or outline objects in images. In still another example, the token instances are extracted from audio-visual content and labeled automatically utilizing known and to be discovered image and/or video segmentation, and/or object detection algorithms. In another example, some of the token instances may be extracted from audio-visual monitoring of the user's surroundings, for example using one or more microphones and/or one or more cameras on the user and/or in the surroundings. In another example, some of the tokens may be extracted by semantic analysis of text, uttered words, conversations, blog posts, twits, or emails; such tokens may represent specific words, phrases, or concepts that can be derived from the content of the stimuli. In another example, some of the tokens may be derived from location-based data.

In one embodiment, a single object such as an image, a sentence, a location, or a sound may be the cause of multiple token instantiations. For example, a cute black puppy may instantiate the tokens "dog" and "black" (its dominant color) and "cute" (its general appearance). A song may instantiate the tokens "Rock 'n Roll" and "loud music".

In one embodiment, token instances are stored as records in a database. Optionally, the token instances are stored as a time-series, where entries in the database correspond to certain times or events and may contain information about the tokens instantiated at that time or event. Optionally, records in the database are stored in a structure that links between the token instances and emotional state annotations of the user corresponding to times in temporal proximity of the user's exposure to said token instances. Optionally, records in the database are stored in a structure that links between the token instances and user measurement channel data corresponding to times in temporal proximity of a user's exposure to said token instances.

In one embodiment, token instances may include values for various attributes such as a token identification number, weight (importance), size, and/or intensity, when applicable to the type of token instance being stored. Optionally, token instances may include the duration, and/or start time and duration, and/or start time and end time, and/or any other equivalent notation designating a period of time, or events, in which the user was exposed to the token instances.

In one embodiment, a token may be instantiated multiple times, optionally, at overlapping times. For example, a scene in which there are several characters appearing, may annotated as having several instances of the token "person".

In one embodiment, some tokens may be grouped into different classes, types and/or abstraction levels. Optionally, a token may belong to one or more groups of tokens. In one example dealing with media a user is viewing, the type of media the user is watching may be a high-level token group called "media type", which may include various tokens like "movie", "tv program", "web cast". On a lower level, there may be tokens describing scenes in a movie, which may grouped together under the label "scene type", which may include tokens like "romantic scene", "action sequence", "dramatic climax". In another example dealing with a user's visit to a supermarket while using a device with augmented reality capabilities (like a smart phone), a high level token group may be "locations", which may include tokens like "user's home", "supermarket", "user's office". A lower level group of tokens may be labeled "sub locations", and include various tokens like "dairy department", "soft drinks section", "checkout line". A group of low-level tokens may include specific products like "cranberry juice", "yogurt", or "bread".

In one embodiment, tokens may be grouped according to various criteria such as the tokens' typical context, and/or location of experience by the user. In one example, a high-level token group may be "activity type" which will typically include activities that may last hours like "watching a movie", "rock climbing", "reading a book", "surfing the web". A low-level token group may be "images on computer screen", which will include various images seen on the computer screen with a typical short duration.

In one embodiment, token instances may be grouped according to their source or cause of instantiation. For example, all token instances instantiated by the playing of a movie (a token for the whole movie, tokens for types of scenes, tokens for images, sounds), can be grouped as having the movie as their source. In another example, all token instances corresponding to words and phrases appearing on a web-page share the web-pages URL as their source, and may be grouped together accordingly.

In one embodiment, tokens may be described using one or more hierarchies. For example, a dog may have the following hierarchical tokens: level 1—animal, level 2—dog, level 3—puppy, level 4—Labrador puppy, level 5—black Labrador puppy. A song may be given the following hierarchical tokens: level 1—music, level 2—rock n' roll, level 3—music by Kiss, level 4—"Rock n' Roll all Night" performed by Kiss.

In one embodiment, patterns of tokens, or subsets of tokens, may be grouped together and represented by a new pattern token. For example, if in a certain time interval, such as the one defined by a temporal window of token instances, instances of the individual tokens comprising the pattern are found, they may be replaced with the corresponding pattern token. Optionally, the pattern token's weight at that time point may equal the sum of its individual tokens' weights and/or the cardinality they have for the purpose of token counts, for instance if saturation is included in the model, may equal the number of tokens in the pattern. Following this stage, the model creation, optimization, and analysis may treat the instances of pattern tokens as regular token instances.

In one embodiment, subsets of tokens that may serve as pattern tokens may be found using algorithms for finding frequent patterns. Optionally, some patterns may involve attribute values of some of the token instances. For example, some of the algorithms described in Han, J., Cheng, H., Xin, D., & Yan, X. (2007), Frequent pattern mining: current status and future directions, Data Mining and Knowledge Discovery, 15(1), 55-86, incorporated herein by reference, may be used for detecting frequent patterns in various ways.

Attention

In one embodiment, some of the token instances may be assigned values reflecting the level of interest a user is predicted to have in said token instances. The terms "interest level" and "attention level" are used herein interchangeably. Optionally, interest level data in tokens may be compiled from one or more sources, such as (i) attention level monitoring, (ii) prediction algorithms for interest levels, and/or (iii) using external sources of information on interest levels. Optionally, interest level data in tokens may be stored as a numerical attribute of token instances. Optionally, the interest level data in tokens may express the relative interest levels in the various token instances. Optionally, interest level data in tokens may be grouped into broad categories, for example, the visual tokens may be grouped into three categories according to the attention they are given by the user: (i) full attention, (ii) partial/background attention, (iii) low/no attention.

In one embodiment, a user's level of interests in some of the tokens may be derived from the user measurement channels, which are processed to detect the level at which the user is paying attention to some of the token instances at some of the times.

In one embodiment, the general attention level may be measured, for example by a camera and software that determines if the user's eyes are open and looking in the direction of the visual stimuli, and/or by physiological measurements that may include one or more of the following: heart rate, electromyography (frequency of muscle tension), electroencephalography (rest/sleep brainwave patterns), and/or motion sensors (such as MEMS sensors held/worn by the user), which may be used to determine the level of the user's consciousness, co-consciousness, and/or alertness at a given moment. In one example, the fact that a user is looking or not looking at a display is used to determine the user's level of interest in a program appearing on the display.

In one embodiment, object-specific attention level may be measured for example by one or more cameras and software that performs eye-tracking and/or gaze monitoring to detect what regions of a display, or region of an object, or physical element the user is focusing his/her attention at. The eye-tracking/gaze information can be compared to object annotation of the picture/scene the user is looking at to assign weights and/or attention levels to specific token instances, which represent the objects the user is looking at.

In one embodiment, various methods and models for predicting the user's interest level are used in order to assign interest level scores for some token instances.

In one embodiment, user interest levels in image-based token instances are predicted according to one or more automatic importance predicting algorithms, such as the one described in Spain, M. & Perona, P. (2011), Measuring and Predicting Object Importance, International Journal of Computer Vision, 91 (1). pp. 59-76. In another embodiment, user interest in objects is estimated using various video-based attention prediction algorithms such as the one described in Zhai, Y. and Shah, M. (2006), Visual Attention Detection in Video Sequences Using Spatiotemporal Cues, In the Proceedings of the 14th annual ACM international conference on Multimedia, pages 815-824, or Lee, W. F. et al. (2011), Learning-Based Prediction of Visual Attention for Video Signals, IEEE Transactions on Image Processing, 99, 1-1.

Optionally, the predicted level of interest from such models may be stored as an attribute value for some token instances. In one example, a model for predicting the user's interest level in various visual objects is created automatically using the one or more selected automatic importance predicting algorithm, using token instances for which there is user attention-monitoring, as training data. In one embodiment, different types of tokens are tagged with different attention data, optionally in parallel.

Analysis of previous observations of the user's interest in some tokens may be used to determine interest in new, previously unobserved, tokens. In one embodiment, a machine learning algorithm is used to create a model for predicting the user's interest in tokens, for which there is possibly no previous information, using the following steps: (i) extracting features for each token instance, for example describing the size, duration, color, subject of visual objects; (ii) using the attention-level monitoring data as a score for the user's interest; (iii) training a predictor on this data with a machine learning algorithm, such as neural networks or support vector machines for regression; and (iv) using the trained predictor to predict interest levels in instance of other (possibly previously unseen) tokens.

In one embodiment, analysis of previous observations of the user may be used to determine interest in specific tokens.

In one embodiment, a predictor for the level of attention a user is expected to pay to different token instances is created by combining the attention predictor models and/or prediction data from other users through a machine learning collaborative filtering approach.

In one embodiment, information gathered from other users who were essentially exposed to the same token instances as the user may be used to assign interest levels for the user, for example, in cases where the user's interest level data is missing or unreliable. In one example, when assigning interest level to tokens extracted from a multimedia, at times when the user's eye-tracking information is missing or inconclusive for a token instance, the interest levels for that token instance can be set to average interest levels given to that token instance by other users who viewed the same multimedia content.

In one embodiment, an external source may provide the system with data on the user's interest level in some tokens and/or token instances. In one example, information on users' interest may be provided by one or more humans by answering a questionnaire indicating current areas of interest. The questionnaire may include areas such as pets, celebrities, gadgets, media such as music and/or movies (genres, performers, etc.), and more. The questionnaire may be answered by the user, friends, relations, and/or a third party. In another example, semantic analysis of the user's communications such as voice and/or video conversations, instant messages, emails, blog posts, twits, comments in forums, keyword use in web searches, and/or browsing history may be used to infer interest in tokens describing specific subjects, programs, and or objects of interest. In yet another example, some of the user's subjects of interest may be provided by third parties, such as social-networking sites like Facebook, and/or online retailers like Amazon.

In one embodiment, a temporal attention level is computed for the user at a specific time. Optionally, the user's temporal attention level refers to a specific token instance or group of token instances. In one example, the temporal attention level is stored as a time series on a scale from no attention being paid to full attention is being paid. Optionally, temporal attention level data is extracted from a visual attention data source (e.g., eye-tracking, face expression analysis, posture analysis), an auditory data sources, monitoring the users movement (e.g., analysis of motion sensor coupled to the user), and/or physiological measurements (e.g., EEG).

In one embodiment, interest levels obtained from various sources are combined into a single "combined interest level score". The combined interest level score may be stored as an attribute in some of the token instances. In one example, the interest level scores from various sources such as attention-level monitoring, predicted interest based on the user's historical attention-levels, and/or interest data received from external data sources, may be available for a token instance. Optionally, the combined interest level score may be a weighted combination of the values from the different sources, where each source has a predefined weight.

Token Instance Weights

In one embodiment, token instances are given a weight attribute, which is correlated with the estimated magnitude of the token instances' influence on the user's affective response. Optionally, a token instance may have a single value or multiple values for the weight attribute. For example, multiple values may describe the token instance weight at various time points. In one embodiment, the system supports queries that provide the values of a token instance's weight at a required time, for example by interpolating and/or extrapolating values from token instance weights at different time points.

In one embodiment, the token instance weight is a predetermined value. In one embodiment, q weight attributes are assigned to a token instance, for example, weights $w_1, \ldots, w_q$ for q different segments of the duration of the token instance's existence. The total weight assigned to the token instance equals $w = w_1 + \ldots + w_q$, and may be distributed to the q attribute values in different ways. In one example, the weight is distributed uniformly, such that $w_1 = \ldots = w_q = w/q$. In another example, the weights may be distributed in a non-uniform way, such as assigning higher weights to earlier segments in the duration of the token instance's existence to reflect the fact that the token's influence on the affective state diminishes as time goes by. Optionally, the weight assignment to various points may follow a parametric distribution, such as an exponential or Gamma distribution, with predefined parameters, and/or parameters that are set as part of the affective response model training.

In one embodiment, attribute values for some of the token instances may be used to modify the weights of the token instances. For example, tokens that have an attribute "size" or "intensity" may be reweighted, for instance, by multiplying the token instance weight with the attribute value(s), to reflect the fact that larger or more intense instances have a stronger influence on the user's affective state.

In one embodiment, some of the attention level scores may be used to reweight token instances. For example, the token instance weight may be multiplied by the attention score for the token instance which is in the range [0,1], or multiplied by the average attention score.

In one embodiment, different types of tokens may be assigned different attention levels at the same time, depending on the circumstances. For example, when viewing media on a screen, if it is determined from a camera monitoring the user that he/she is momentarily not looking at the screen, all visual token instances may be given an interest level reflecting that fact, for instance a weight of 0. At the same time, it may be assumed that the user is still listening; therefore, sound-related token instances may still be given a weight greater than zero.

In one embodiment, general attention levels are allowed to affect long-lasting token instances that involve things like the genre, program, or main characters; while short lasting token instances, like object tokens such as a dog or a car, are not influenced by the general attention levels unless the content is about the specific token instance. For example, a user is watching a movie where the scene takes place in a living room: If the user is not paying attention to the media, there is no reason to assign a weight to token instances of items in the background of the scene, such as the sofa or napping dog, since the user is not paying attention to the scene and thus anything learned about the user's affective response towards those token instances is probably noise.

In one embodiment, the weights of token instances in a database are normalized. For example, the weights may be normalized in such a way that the sum of weights from all token instances in the database at a given time, or all instances in a temporal window of token instances, equals a required value. Optionally, weights of token instances may be normalized in such a way that depends on the sum of the token instance weights (denoted by S). For example, token instance weights may be normalized in such a way that they sum up to $\log(1+S)$, or the square root of S.

Emotions

In one embodiment, the user's emotional state is annotated at some time points, or for some temporal windows of token instances, using various methods for representing emotions. Optionally, the annotations are obtained utilizing a transformation from a domain representing measurements to a domain representing internal emotional states. Optionally, the user's emotional state is annotated by the user, for example using self-report systems such as questionnaires or GUIs.

In some embodiments, the user's emotional state may be represented using different methods:

In one embodiment, emotional states are represented using discrete categories. For example, the emotion categories may include three categories: negatively excited, positively excited, and neutral. In another example, the emotion categories include happiness, surprise, anger, fear, disgust, and sadness.

In yet another example, the categories can relate to a user's level of interest in content comprising token instances, such as interested or not interested.

In one embodiment, emotional states are represented using a multidimensional representation, which characterizes the emotional state in terms of a small number of latent dimensions. In one example, the emotional states are represented as points in a two dimensional space of Arousal and Valence. Arousal describes the physical activation and valence the pleasantness or hedonic value. Each detectable experienced emotion is assumed to fall in a specified region in that 2D space. Other dimensions that may be used to represent emotions include: potency/control (refers to the individual's sense of power or control over the eliciting event), expectation (the degree of anticipating or being taken unaware), and intensity (how far a person is away from a state of pure, cool rationality). The various dimensions used to represent emotions may be correlated. For example, the values of arousal and valence are often correlated, with very few emotional displays being recorded with high arousal and neutral valence. In one embodiment, emotional states are represented as points on a circle in a two dimensional space pleasure and arousal (e.g., the "circumplex").

In one embodiment, emotional states are represented using a numerical value that represents the intensity of the affective state with respect to a specific emotion. For example, a numerical value stating how much the user is enthusiastic or happy. Optionally, the numeric value for the emotional state may be derived from a multidimensional space representation. For example, let P be a path or collection of points in the multidimensional space. For every point p in P, a numerical value d(p) can be computed, for instance by computing the distance that needs to be traveled along P from a reference point serving as zero to reach p. Given a point q in the multidimensional emotional space, which is not in the set of points P, the projection of q on P is a point q' in P, for which the Euclidean distance (q,q') is essentially minimal. The numerical value for the point q may be assigned the same value as its projection on P, which equals d(q').

In one embodiment, emotional states may be modeled using componential models that are based on the appraisal theory, as described by the OCC model (Ortony, Clore & Collins, 1998). According to this theory, a person's emotions are derived by appraising the current situation (including events, agents, and objects) with respect to the person goals and preferences.

In one embodiment, emotional states represented by categories are converted to a multidimensional representation, for example, by assigning each category a representative point in the multidimensional space.

In one embodiment, emotional states described as points in a multidimensional space are converted into a categorical representation in several ways. In one example, there are predefined categories, with each category having one or more representative points in the multidimensional space. An unassigned point P in the multidimensional space may be assigned to the category that has a representative point P' for which the Euclidian distance between P and P' is smaller or equal to the distance between P and all other category representative points. In another example, the multidimensional space representing emotions is partitioned into a number of regions that cover the entire multidimensional space. Following that, the points falling in the same region belong to the same category. For example, a valid partition may be splitting the arousal-valence space into four quadrants; consequently, each point in the multidimensional space belongs to one of the four resulting categories. In yet another example, the multidimensional emotional space contains N or more points describing emotions, for example, from the emotional states of multiple people and/or multiple time points. The points in the multidimensional space are then clustered into N clusters, using an algorithm like K-means with the Euclidean distance metric. Each cluster may then represent a category, with the mean of each cluster serving as a representative point for the category. Each existing or new point P in the dimensional space may then be assigned a category by choosing the category whose representative point has a minimal distance to P.

In one embodiment, emotional states are described using a scalar value, and may be converted to a categorical representation, for example, using predefined categories, where each category has one or more representative scalar value(s). An unassigned point P in the space may be assigned to the category which has a representative point P' for which the value $|P-P'|$ is minimal.

In one embodiment, a method is provided for computing the distance between two emotional state annotations. In one example, the distance between two categorical annotations may be computed using a pre-defined distance matrix that holds the distance between pairs of annotations. In another example, the distance between two annotations in a scalar representation may equal the absolute value of the result of the subtraction of the value of the first annotation from the second. In yet another example, the distance between two annotations using a multidimensional emotional state representation may equal the Euclidean distance between both annotations.

Situations

In one embodiment, a user's exposure to tokens and/or the user's response are monitored over a long period of time that spans various situations. Different situations may affect the user's behavior and response. For example, the user's reaction to certain token instances may change depending on the situation in which the user was in while being exposed to the token instances. For example, a user may react calmly to adult-themed material when viewing alone (one situation), however the same user may react angrily if such material was to appear while the user's children were present (a different situation). In another example, the user's baseline value for an emotional state and/or user measurement channel may change significantly in different situations, such as when the user is driving vs. relaxing at home, or when the user is alert vs. inebriated.

In one embodiment, information describing a user's situation during certain times and/or events is stored in a database. Optionally, some situations are described using one or more token instances and/or attribute values of one or more token instances. Optionally, information describing a situation is linked to some of the token instances. Optionally, information describing a situation may be linked to database records corresponding to temporal windows of token instances. Optionally, information describing some situations may be in the form of situation identifiers.

In some embodiment, the situation identifiers are received describing the user's situation during certain times and/or events. Optionally, a classifier may be trained to identify the situation occurring during new times and/or events. Optionally, the training samples used to train such a classifier comprised of one or more of the following elements corresponding to a certain time and/or event: values of some token instances and/or their attributes, values from one or more user measurement channels, an emotional state annotation, a baseline value for the emotional state, and/or baseline values for one or more user measurement channels. Optionally, some training samples are assigned labels corresponding to their respective situation identifiers. Optionally, a machine learning classification algorithm is trained using the training samples, in order to produce a classifier that may identify the situation in which the user is at various times and/or events. For example, the machine learning algorithm used to train a classifier may be a neural network classifier, a support vector machine, a maximum entropy classifier, or a random forest. In one embodiment, the training data may be comprised of both labeled and unlabeled data (for which the situation is unknown), and a semi-supervised machine learning method may be employed to train the classifier.

Figure 13:
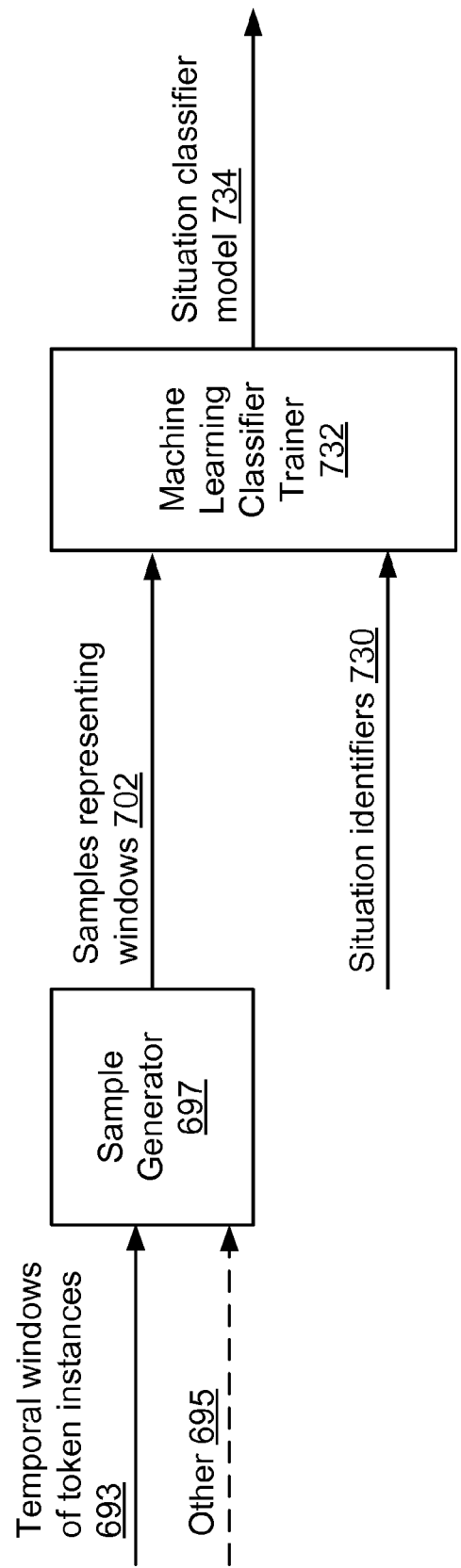
FIG. 13 illustrates an ML-based situation predictor training.

FIG. 13 illustrates one embodiment of a system that trains a machine learning-based situation predictor. The sample generator 697 is configured to receive temporal windows token instances 693 and possibly other inputs 695 such as information regarding a baseline values. The sample generator 697 produces samples 702 corresponding to the temporal windows of token instances 693 and the other inputs 695; the samples 702 are provided to a machine learning classifier trainer 732, which also receives situation identifiers 730 that serve as target values for the sample. The trainer 730 utilizes a machine learning model training algorithm to train situation classifier model 734 (e.g., the model may be for a classifier such as a decision tree, neural network, or a naive Bayes classifier).

In one embodiment, data may initially not include a description of situations, so situations may need to be discovered from the data in an unsupervised or semi-supervised fashion. The following examples describe different situation characterizations that can be discovered automatically:

(i) Certain situations may be characterized by a small set of specific token instances. For instance, the situation in which the user is driving may be characterized by a token instance "user is driving", while the situation that the user is not alone may be characterized by a token instance "other people are in the user's vicinity".

(ii) Different situations may be characterized by the fact that the user is exposed to a different characteristic set of similar token instances, and/or token instances originating from similar sources. For example, in a situation labeled "watching TV" a user may be exposed to visual token instances belonging to images, while in a situation labeled "reading", the user may be exposed to many token instances corresponding to words.

(iii) Some situations may be characterized by the fact that the user exhibits a noticeably different response to instances of certain tokens. For example, in a situation that may be labeled "hungry" the user may experience a certain affective response such as high arousal when exposed to token instances related to food. However, in a situation labeled "not hungry", the user may exhibit a much milder affective response to the token instances related to food.

(iv) Some situations may be characterized by the fact that the user has typical baseline levels for the affective state and/or one or more of the user measurement channels. For example, when in the situation "driving" a user may have a typical affective state baseline that is at a high level of arousal for the whole duration or most of time in which the user this situation, while when the user is in the situation "relaxing at home", the baseline arousal level is much lower.

(v) Situations may be characterized by the fact that samples representing certain times or events in which the user was in the same situation, tend to belong to the same clusters when an unsupervised clustering algorithm is run on the samples. For example, the samples may be comprised of vector representations of temporal windows of token instances. When a clustering algorithm like K-means is applied to the data, each cluster of vectors of windows may be considered a different situation.

In one embodiment, a method for detecting different situations utilizes a mixture model and an Expectation Maximization (EM) algorithm. Optionally, the method comprises the following steps:

(i) Acquiring or receiving samples—data collected for certain times or events is received, for example in the form of vector representations of temporal windows of token instances. Optionally, variables in the vectors participating in the EM likelihood computation may be assumed to come from a distribution with a parametric form; for example, a variable with k possible values that may be considered to have a discrete distribution with k parameters $p1, \ldots, pk$, such that $pi \geq 0$, for $i=1 \ldots k$, and $p1+ \ldots +pk=1$, which correspond to the variable's k possible values. In another example, a real-valued variable may be assumed to have a parametric distribution, such as a Gaussian with parameters $\mu, \sigma^2$.

(ii) Initializing—the method receives a parameter N describing the desired number of situations. Initially some of the samples are assigned to the N situations. Optionally, some situation assignments are received as an input. Optionally, the samples are randomly assigned situations to N situations. Optionally, an initial partitioning of samples is done using one or more of the aforementioned characterizations of different situations. For example, all samples with a certain token instance (e.g., "driving") may be assigned the same situation. In another example, all samples for which there is a similar user measurement channel value (such as low heart rate), are assigned the same situation. Optionally, the assignment process to situations may be hierarchical, and use more than one round of partitioning. For example, all sample grouped together because of a low heart rate may be further refined by clustering them into several clusters. The partitioning into situations may continue until the total number of clusters of samples (corresponding to situations) reaches N. Optionally, certain samples may belong to more than one situation (i.e., their weight may be spread over several clusters).

(iii) Training a model using an EM approach—looping until the model converges, performing the following steps:

Expectation—using the current set of parameter values, compute for each sample the probability that it belongs to each of the situations. Optionally, in the first iteration, the initial assignments to situation clusters may be used instead.

Maximization—re-estimate the parameters using maximum a posteriori parameter estimation to find a set of parameter values that maximizes the expected log likelihood of the data.

(iv) Returning results—returning the model's parameters after convergence and/or situation assignments for samples in the form of probabilities of a sample being in the N different situations or returning only the most likely situation for each sample.

In one embodiment, samples with situation assignments obtained with the EM procedure may be used to train a classifier for predicting the situation for new unseen samples. Optionally, a machine learning method such as a neural network, support vector machine, random forest, decision tree, or other machine learning classification algorithms, may be used for this task.

Figure 14:
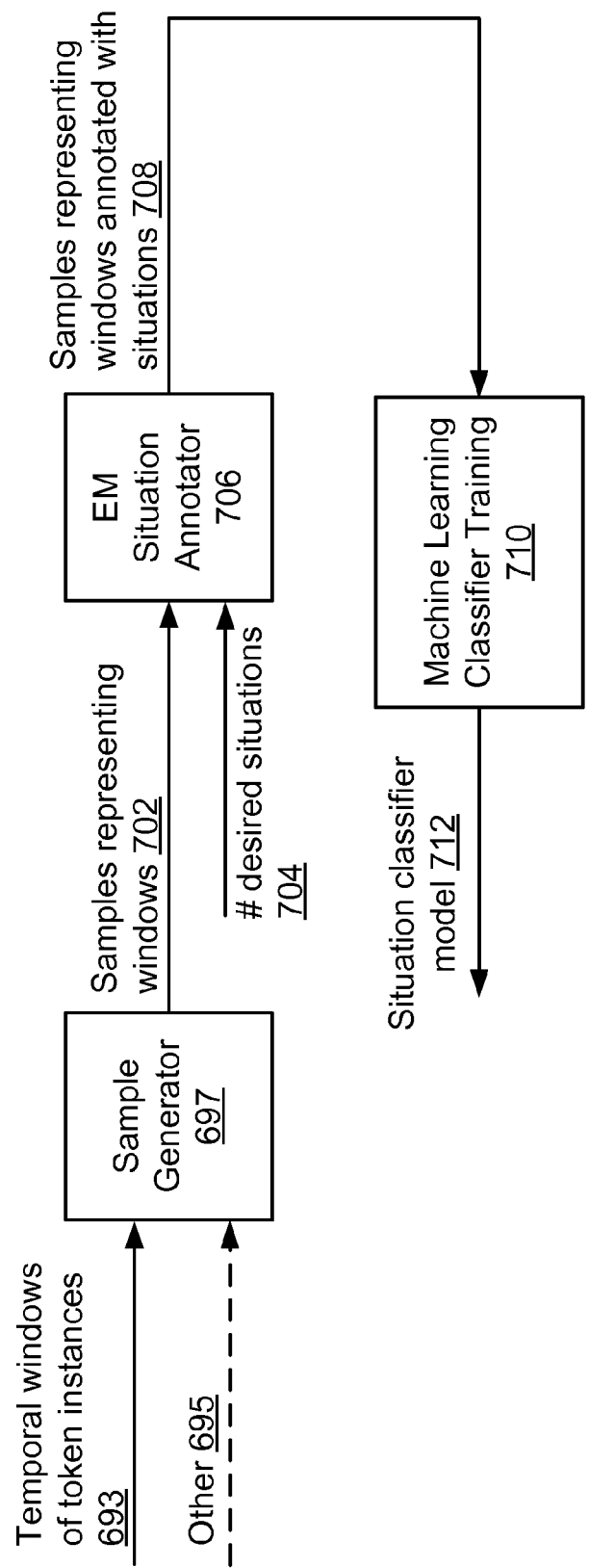
FIG. 14 illustrates EM-based situation discovery.

FIG. 14 illustrates one embodiment EM-based situation discovery in which a system trains a situation predictor. The sample generator 697 is configured to receive temporal windows token instances 693 and possibly other inputs 695 such as information regarding a baseline values. The sample generator 697 produces samples 702 corresponding to the temporal windows of token instances 693 and the other inputs 695. The samples 702 are provided to an EM-based situation annotator 706, which also receives a desired number of situations 704. After running the EM algorithm on the input data as described above, the EM situation annotator can add annotations describing the situation (e.g., group index) for the samples. The samples representing windows that are annotated with situations 708 are provided to a module that performs machine learning classifier training 710, in order to produce the situation classifier model 710. The module 710 utilizes a machine learning model training algorithm to train situation classifier model 712 (e.g., the model may be for a classifier such as a decision tree, neural network, or a naive Bayes classifier).

In one embodiment, a method for identifying different situations utilizes a clustering algorithm. Data collected for certain times or events is received and converted to samples that may be processed by the clustering algorithm, for example in the form of vector representations of temporal windows of token instances. Optionally, the clustering algorithm uses a distance function for samples that utilizes a function for computing the distance between two temporal windows of token instances. Optionally, the clustering algorithm utilizes a distance function that computes the distance between samples' emotional state annotations. Optionally, the distance function between samples combines the two measures, for example using a weighted sum, where a pre-defined weight $\alpha > 0$ is given to distance between the temporal windows of token instances of the two samples, and a weight $1-\alpha$ for the distance between the emotional state annotations of the two samples.

In one embodiment, a hierarchical bottom-up clustering algorithm is used to identify situations. Given a pre-defined number of desired situations, the algorithm is run iteratively, starting with each sample as a singleton cluster, and in each iteration, joining the most similar clusters. Optionally, the algorithm proceeds to run until a threshold is reached such as a maximal distance between joined clusters. Optionally, the algorithm proceeds until the number of clusters reaches a predefined target.

In another embodiment, partitioning clustering algorithm such as K-means is used to identify situations. Optionally, the algorithm is run using a pre-specified number of desired clusters. Optionally, the clustering algorithm is run several times with a different number of desired clusters, choosing the configuration producing a desired tradeoff between the number of clusters and the tightness of clusters (expressed for example, as mean squared distance to the cluster centers).

In one embodiment, after running the clustering algorithm, each sample is assigned a situation identifier corresponding to its cluster. The samples with situation assignments may be used to train a classifier for predicting the situation for new unseen samples. Optionally, a machine learning method such as a neural network, support vector machine, random forest, decision tree, or other machine learning classification algorithms, may be used for this task.

Figure 15:
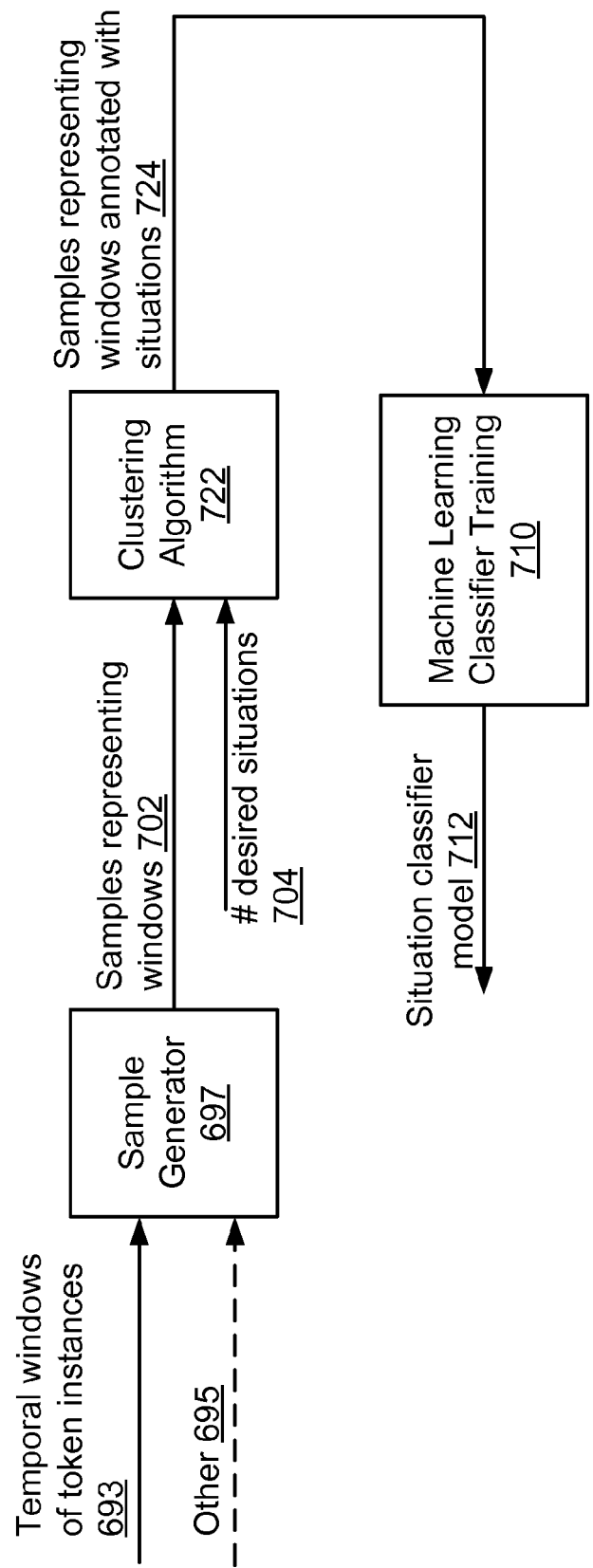
FIG. 15 illustrates clustering based situation discovery.

FIG. 15 illustrates one embodiment clustering based situation discovery in which a system trains a situation predictor. The sample generator 697 is configured to receive temporal windows token instances 693 and possibly other inputs 695 such as information regarding a baseline values. The sample generator 697 produces samples 702 corresponding to the temporal windows of token instances 693 and the other inputs 695; the samples 702 are provided to a clustering algorithm 722, which also receives a desired number of situations 704 (corresponding to the desired number of clusters). After running the clustering algorithm in the input data as described above, the clustering algorithm's output be utilized as annotations describing the situations for the samples (e.g., the cluster index for each sample). The samples representing windows that are annotated with situations 724 are provided to a module that performs machine learning classifier training 710, in order to produce the situation classifier model 710. The module 710 utilizes a machine learning model training algorithm to train situation classifier model 712 (e.g., the model may be for a classifier such as a decision tree, neural network, or a naive Bayes classifier).

Baselines

In one embodiment, one or more baseline levels are computed for the user's response, which may be a variable representing values of the user's affective state and/or values of some of the user measurement channels. A user's baseline response level is a representative value of the user's usual state, computed from multiple values acquired over a long period, such as a few hours, a day, a month, or even a year. A baseline level usually reflects the expected value for the user's response when not considering the effects of the user's short term-exposure to token instances. In one example, a response variable may correspond to an emotional state (is the user typically relaxed, anxious, excited). In another example, a response variable corresponds to a physiological signal value such as a user's typical heart rate.

In one embodiment, a user's baseline level is computed for a categorical response variable, such as the user's emotional state, which is represented by emotional categories. Optionally, the baseline level is computed by observing the values of the categorical response variable over a long period, and using for a baseline level the category that was the response variable's value the longest time. Optionally, the baseline level comprises a set of values that describe the proportion of time the response variable had each of the categorical values.

In one embodiment, a user's baseline level is computed for a real-valued response variable, such as a user measurement channel or a dimension in an emotional state representation. Optionally, the baseline level is computed from observations of the response variable's values collected over a long period. Optionally, a baseline level may be multidimensional, being comprised of several baselines corresponding to individual dimensions. For example, a user's emotional state baseline may be comprised of a baseline level for the user's arousal and a baseline level for the user's valence.

In one embodiment, a user's baseline level for a response variable is computed using a window of a fixed duration (such as an hour, a day, a week), from which the values of the response variable are collected for the baseline computation. Optionally, the baseline level is computed when the user is in a specific situation (such as being alone, watching TV, being in a happy mood) by collecting values of the response variable during periods when the user was in essentially the same situations.

In one embodiment, a user's baseline level for a response variable is computed by collecting multiple values of the response variable, optionally while the user is in similar situations, and applying various computational procedures to the collected values, such as: (i) averaging values in a sliding time window of a predefined size; (ii) a weighted average of the collected values; (iii) low-pass filtering to the values; (iv) Fourier transform to the collected values; and/or (v) wavelet transform analysis to the data.

In one embodiment, a baseline value may be comprised of a weighted combination of several baseline values computed from data collected at different time-scales and/or situations. For example, a baseline for the emotional state of a user watching an action movie on a television set may be comprised of the following baselines: 20% of the weight is given to the user's baseline computed from data collected during the previous 24 hour period (in all situations), 30% of the weight is given to the baseline computed from data collected from the user's most recent two hours of television viewing (of any program type), and the remaining 50% of the baseline weight is given to the baseline computed from the last 100 hours of the users viewing of action content (such as movies or television programs).

In one embodiment, the user's baseline level values for a response variable computed at different times and/or situations are stored in a database. Optionally, additional values are stored in the database such as (i): values and/or baseline values for user measurement channels; (ii) values and/or baseline values for the user's emotional state; (iii) situation identifiers denoting situations the user was in during the period in which data was collected for the baseline computation; (iv) values and/or baseline values of tokens describing the user's situation; and/or (v) linkage information between baseline values at certain times and records corresponding to temporal windows of token instances.

In practice, the ideal baseline function is often not a simple smooth average function, because the baseline level may strongly depend on the user's situation. As a result, the user's baseline level may change significantly during a short duration of time when there is a significant change in the user's situation. Thus in practice, the baseline does not often resemble a smooth slow-changing function typically observed when the baseline is computed as an average of values collected over long periods of time. For example, when the user is alone at home watching TV, he/she has one baseline level for the emotional state; if the user's mother-in-law enters the house, the user's emotional state baseline may change significantly in a very short time, and remain in that changed state for the duration of the mother-in-law's presence. This rapid change in baseline may not be reflected in a timely manner if the baseline is computed simply by averaging values in a large temporal window, while disregarding the context of different situations. The following paragraphs exemplify embodiments for computing such rapidly adjusting situation-dependent baselines.

In one embodiment, a user's baseline level is predicted using a machine learning method, such as a support vector machine, a regression method, a neural network, or support vector machine for regression. The training data for the machine learning method may include samples comprising response variable values and various input variable values. Optionally, the data for the samples is collected while the user is in specific situations, in order to train situation-specific baseline predictors for the user.

In one embodiment, the training data for a machine learning-based baseline value predictor for a user comprises data of one or more of the following types:

(i) Computed baseline values for the user for the response variable and/or other variables (such as user measurement channels). Optionally, the baseline values are computed using data collected in different ways, such as by collecting values from time intervals of different durations and/or times in which the user was in certain situations. Optionally, the baseline values for the time windows computed for the data from the time intervals using various methods such as averaging, low-pass filtering, Fourier transform, and/or wavelet transform.

(ii) Situation identifiers and/or values of some token instances, or their attributes, at specific times (such as the time for which the baseline is predicted), which may be used to define the user's situation. Note that the token instance values provided to the machine learning method may include long-lasting token instances that describe properties like the user's activity (e.g., watching a movie, driving, being massaged), or properties describing the user's environment (e.g., at home, sitting alone), or the user's state or mood (e.g., excited, tired). Such long-lasting token instances may have long-lasting influence on the user's baseline values.

(iii) Baseline values computed or collected from other data sources, such as models of other users.

In one embodiment, after using a machine learning training method to process the training data, the resulting model is used to predict the user's baseline level for a response variable. When information regarding the user's situation and/or situation-specific inputs are provided (such as baselines for specific situations), the resulting predictions for baseline values made by the classifier may rapidly adjust to situation changes that may lead to dramatic changes in the user's baseline level for some of the variables.

Figure 16:
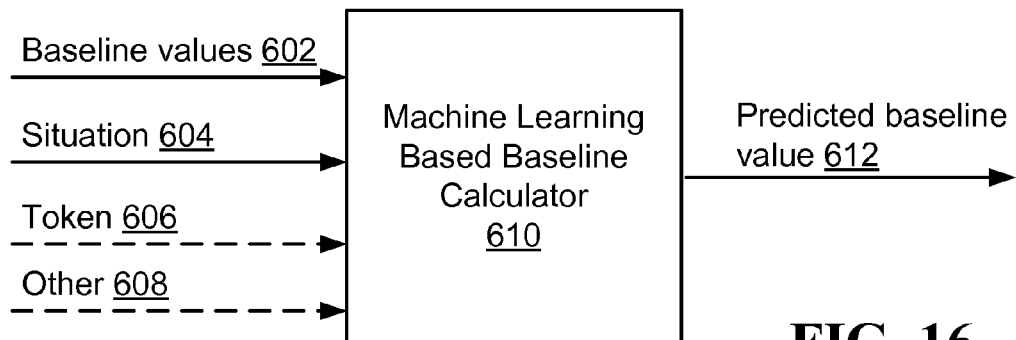
FIG. 16 illustrates a machine learning-based baseline calculator.

FIG. 16 illustrates one embodiment of a system in which a predicted baseline value 612 is calculated by a machine learning-based baseline calculator 610. The machine learning-based baseline calculator receives input such as baseline values (e.g., current and/or taken in the recent past), data regarding a situation 604 the user is in. Optionally, the calculator 610 receives additional information such as token 606 and/or other information such information as situation specific baseline values. The calculator 610 may utilize various machine learning methods such as predictor models (e.g., regression, support vector machine, decision trees) in order to calculate the predicted baseline value 612. The predicted baseline value 612 may be expressed in terms of an emotional state (e.g., level of excitement) and/or as a value of a user measurement channel (e.g., a heart rate).

In one embodiment, a method for calculating a situation-dependent rapidly adjusting baseline value predictor for a user utilizes a database, in which there are annotations describing the user's response and corresponding situation identifiers, for at least some of the annotations. Optionally, some of the annotations stored in the database correspond to emotional states. Optionally, some of the annotations stored in the database correspond to values from measurement channels of the user.

In one embodiment, a database is provided with a situation identifier, and optionally, a time scope from which to extract annotations. The database retrieves annotations corresponding to the provided situation identifier, optionally, occurring within the provided time scope. In some examples, the retrieved annotations span a long time, in which the user may have been in various situations. Thus, the retrieved annotations may correspond to intermittent time intervals, separated by intervals of time in which the user was in situations other than the one designated by the provided situation identifier.

In one embodiment, a baseline value for the response variable is computed from annotations retrieved from a database, for example, by averaging the values, or performing low-pass filtering on the values. Since the values retrieved from the database correspond to a specific situation, the computed baseline also corresponds to the situation. Thus, even if the user changes situations in a very short time, the computed baseline is adjusted rapidly to reflect the new situation. These situation-dependent changes in the baseline level occur despite the fact that the baseline may be computed by a weighted average data spanning a long duration. This is opposed to a sliding window approach in which, typically, if the window has a length of T (for example T=1 hour), the computed average changes slowly, taking time to reflect situation-dependent changes in the baseline. Thus, even after a situation changes, it typically takes a sliding window a long time, such as T/2, to significantly reflect the change in the baseline.

Figure 17:
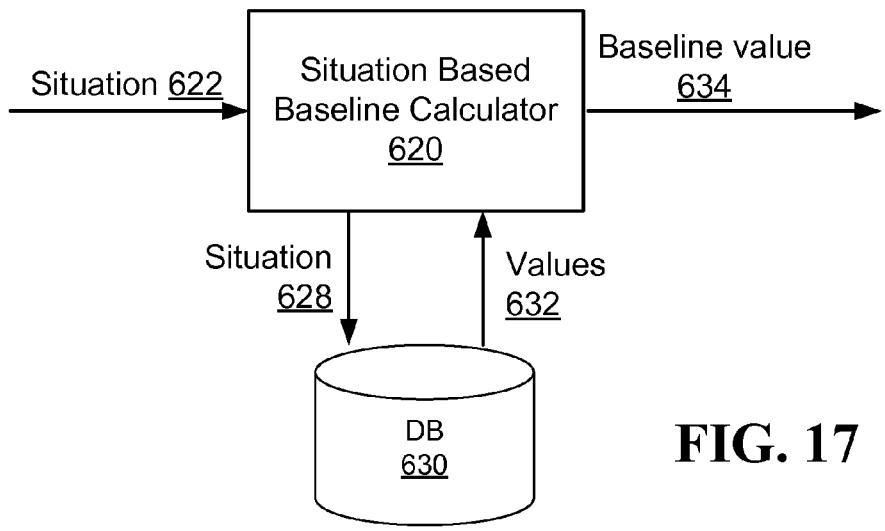
FIG. 17 illustrates a situation-based baseline calculator.

FIG. 17 illustrates one embodiment of a system in which a baseline value 634 is calculated by querying a database 630 according to a situation. A situation based baseline calculator receives data regarding a situation 622 in which a user may be. This data is used to formulate a query describing the situation 628, which is provided to the database 630. The database extracts information according to the situation 628 and returns it to the calculator 620 as values 632. The values 632 may be processed by the calculator 620 in order to generate the baseline value 634.

In one embodiment, a method for calculating rapidly adjusting baseline value predictor for a user, utilizes a database that comprises data such as annotations describing the user's affective response, information regarding the token instances the user was exposed to and/or values from the user's measurement channels. Optionally, the data in the database is accessible as a collection of temporal windows of token instances and their corresponding annotations. In addition, a distance function for computing the distance between database records is also utilized, for example, a function that computes the distance between vector representations of temporal windows of token instances. The computation of the baseline comprises the following steps: (i) The system is given an input record describing the time for which the baseline needs to be computed; (ii) Optionally, the system is given a time interval from which database records may be extracted as samples. Optionally, if one is not provided, the system may use a fixed time interval such as the last 48 hours; (iii) The system scans a database in the time interval, retrieving all records whose distance from the input record is below a pre-defined threshold; And (iv) The values, from which the baseline is to be computed, are extracted from the retrieved records, and a baseline value is computed, for example, by averaging the values, low-pass filtering, or applying a Fourier transform analysis.

Figure 18:
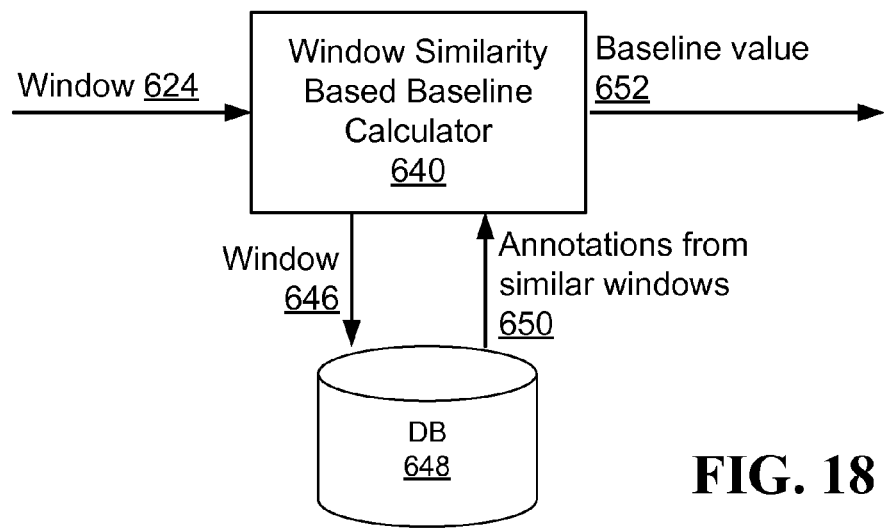
FIG. 18 illustrates a window similarity-based baseline calculator.

FIG. 18 illustrates one embodiment of a system in which a baseline value 652 is calculated by querying a database 648 according to a window 624. A window similarity-based baseline calculator 640 receives data regarding a window 624 to which a user may be exposed. This data is used to formulate a query describing the window 646, which is provided to the database 648. The database extracts information of known annotations to similar windows to the query window 646 and provides the annotations from similar windows 650 to the calculator 640 for processing in order to generate the baseline value 652.

Windows

In one embodiment, individual temporal windows of token instances may be assigned weights. For example, a certain window may be given a higher weight than others may be given if it is deemed more important, for instance, if it appears before a time where there is significant change in the user's predicted emotional state and/or user measurement values. In another example, certain windows may cover times in which the measurements are known to be more accurate, so the window weights may be increased in order to increase these windows' influence during model training.

In one embodiment, the token instances in a window are represented by a vector. For example, where the number of possible different tokens is N, a window is represented by a vector of length N, where position i in the vector holds the sum of the weights of all instances of token i in the window, or zero if there were no instances of token i in the window. Optionally, position i in the vector may hold the number of instances of token i that existed in the window.

In some embodiments, the vectors representing windows are preprocessed and/or modified using some of following methods.

In one embodiment, a set of token instances in a window is filtered to exclude some of the token instances. For example, only the top K token instances with the highest weights are represented in a window.

In one embodiment, weight values in a window's vector are normalized. Optionally, the weights are normalized so the sum of the weight attributes in the window's vector equals a pre-defined constant, for example 1. Alternatively, the weights in the vector, which before normalization sum up to W, are normalized to sum up to a function of W, such as log(1+W), or the square root of W. Optionally, the token instance weights are normalized according to the duration of the window. For example, by dividing a token's instance weight by the duration of the window, or by a function of the duration of the window.

In one embodiment, additional values may be added to a window's vector that are derived from various sources, such as the attribute values for the token instances in the window, attribute values from other windows, or various baseline values.

In one embodiment, window vectors include variables derived from the token instances' attribute values. For each attribute, variables may be added in one or more of the following ways: (i) A single variable representing all instances in the window. For example, the attribute describing the general interest level, as measured by an eye-tracking device, may be added as a single variable. In another example, a single variable "intensity" may be added to the vector and given the average value of the intensity attribute for all token instances that have that attribute. (ii) Multiple variables representing different groups of token instances. For example, separate variables for the attribute sound energy may be created for different types of token instances, such as "short sounds", tokens whose source is "music videos", and those whose source is "classical music". (iii) Multiple variables for each token instance. For example, each token instance may optionally have variables such as weight, interest level, and size.

In one embodiment, the vectors describing temporal windows of token instances include variables describing a baseline value and/or a situation identifier corresponding to the window's scope.

In one embodiment, the vectors describing temporal windows of token instances include variables describing the difference between the user's state at a certain time (e.g., user emotional state, or a value from a user measurement channel) and the user's baseline value for the corresponding time (e.g., the predicted baseline value for the user's emotional state or user measurement channel value).

In one embodiment, the vectors describing temporal windows of token instances include a variable describing the duration of the temporal windows of token instances.

In one embodiment, the vectors describing temporal windows of token instances include variables describing the number of token instances in the window and/or their weight. Adding such a variable may assist in incorporating the effects of sensory saturation into models. Often when saturation occurs, the effect of an additional stimulus is diminished when a large number of stimuli are experienced simultaneously. Optionally, separate variables may be added for different groups of tokens, such as image tokens, word tokens, or music tokens.

In one embodiment, the vectors describing temporal windows of token instances include variables describing the number of times a token had been instantiated previously in various windows. For example, a variable describing how many times in the past minute/hour/day a token had been instantiated is added for some tokens or groups of tokens in order to assist models account for affects of habituation, where repeated exposure to the same stimuli may diminish their effect on the user.

In one embodiment, variables in the vectors describing temporal windows of token instances may be split into b variables representing b bins for the values of the variables, each bin representing a different range of values.

In one embodiment, a variable may be split into several conditional variables, all corresponding to the same original variable; however, only one of the derivative variables is given a value in each window. The choice of which of the variables is given a value may depend on a value from another source such as token instance or baseline value. For example, a variable corresponding to the token "movie" may be split to two separate variables according to a token named "viewer is watching alone", so if the user is watching the movie alone, a non-zero value is given to the first variable corresponding to "movie". And if the user is not alone, a non-zero value is given to the second variable corresponding to "movie". In another example, variables are split according to the value of a baseline for the user. For example, splitting a variable according to the quadrant in a 2D arousal/valence space in which the baseline value falls. Such splits may assist certain models to account for the fact that certain token instances may have a dramatically different effect on the user, depending on the user's baseline emotional state (such as the person being in a good or bad mood).

In one embodiment, a new variable in a vector describing temporal windows of token instances may be assigned values that are the result of a function applied to one of the values of one or more variables in the vector. For example, a variable may equal the square of the weight assigned to a token instance. In another example, a variable may equal the weight of a token instance multiplied by the interest level of that token instance. Optionally, the new variable may replace one or more of the variables used to assign its value.

In one embodiment, a distance function is provided for computing the distance between vectors representing temporal windows of token instances. In one example, the distance function computes the dot product of two vectors. In another example, the distance function computes the distance between two vectors using a metric such as the Euclidean distance or Hamming distance. In yet another example, where X1 is the set of token instances in a first window and X2 is the set of token instances in a second window, the distance between the windows equals $1-(|X1 \cap X2|/|X1 \cup X2|)$.

Databases

In one embodiment, a database stores a list of the token instances representing stimuli that may influence a user's affective state. Optionally, each token instance in the list is stored as a token identifier linked to a record comprising additional attributes such as beginning time of the token's instantiation and/or the user's exposure to the token instance, duration of exposure and/or instantiation, the weight of the token instance, the user's interest/attention level in the token instance. Optionally, the database also includes affective response annotations, for example, an emotional state represented as a category, a scalar, or multidimensional value. Some of the stored token instances may be linked to the annotations, for instance by storing the annotation as an attribute of the token instances. Optionally, the database also includes situation identifiers describing the user's situation when being exposed to some token instances. For example, the situation identifiers may be added as token instances and/or attributes of token instances. Optionally, the database is used to supply data for training a machine learning-based affective response model for the user.

In another embodiment, a database stores a collection of temporal windows of token instances. Optionally, each window has a fixed duration, for example, ten seconds. Optionally, the token instances and some of their attributes (such as weight, interest/attention level, and size) are represented by a vector of values. Optionally, windows may be assigned annotations representing affective responses, such as an emotional state and/or change in state represented as a category, single dimensional value, and/or multidimensional values. Optionally, windows may be assigned one or more situation identifiers, denoting the user's situation when being exposed to the tokens in the window. Optionally, the situation identifiers are derived on demand from the stored tokens. Optionally, the database is used to supply data for training a machine learning-based affective response model for the user.

In one embodiment, the token instances stored in a database are obtained from long-term monitoring of the user, for example, for a period lasting from days to years. Optionally, the token instances stored in the database originate from multiple token sources, and the user may be exposed to them in many different situations. Optionally, the user is exposed to more than one token instance simultaneously, i.e., the user is exposed to multiple tokens with overlapping instantiation periods. Optionally, some of the stored tokens instances comprise representations of elements extracted from digital media content, such as images, sounds, and/or text. Optionally, some of the stored tokens instances comprise representations of elements extracted from an electromechanical device in physical contact with the user.

In one embodiment, database storing information about token instances, also stores information from at least one user measurement channel. Optionally, the database includes linking information such as time stamps to associate between token instances and the user measurement channels measured in temporal vicinity of the exposure to some of the token instances. Optionally, the user measurement channels may be stored at different time resolutions, for example, values of EEG signals may stored every 50 milliseconds, while skin temperature may be stored every two seconds.

Figure 19:
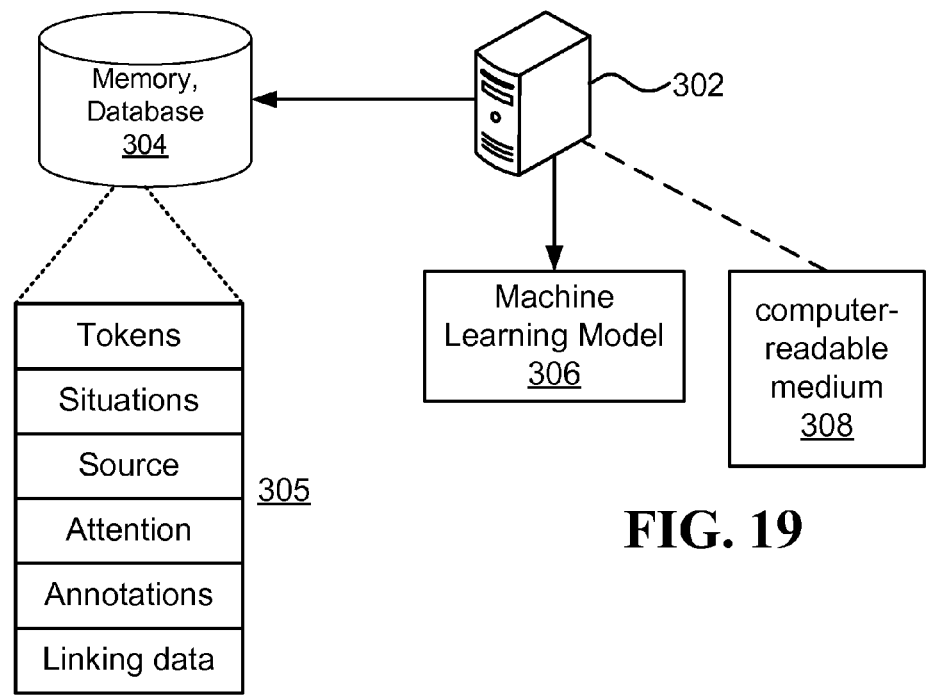
FIG. 19 illustrates a token database.

FIG. 19 illustrates a memory 304 for storing data for access by an application program 302 being executed on a data processing system. A data structure 305 stored in the memory 304 includes information resident in a database 304 used by the application program 302. The application program 302 trains a machine learning based affective response model for a user 306, using the data structure stored in the memory. In one example, the data structure 305 stored in the memory includes: (i) Token instances representing stimuli that influence a user's affective state, stored in the memory. The stored token instances are spread over a long period of time that spans different situations, and a plurality of the stored token instances have overlapping instantiation periods. (ii) Data representing levels of user attention in some of the token instances, used by the application program to improve the accuracy of the machine learning based affective response model for the user. (iii) Annotations representing emotional states of the user, stored in the memory. The stored annotations are spread over a long period of time that spans different situations. And (iv) linkage information between the token instances, the data representing levels of user attention, and the annotations. Further illustrated an optional computer-readable medium 308 that includes instructions for training the machine learning based affective response model for the user 306.

Figure 20:
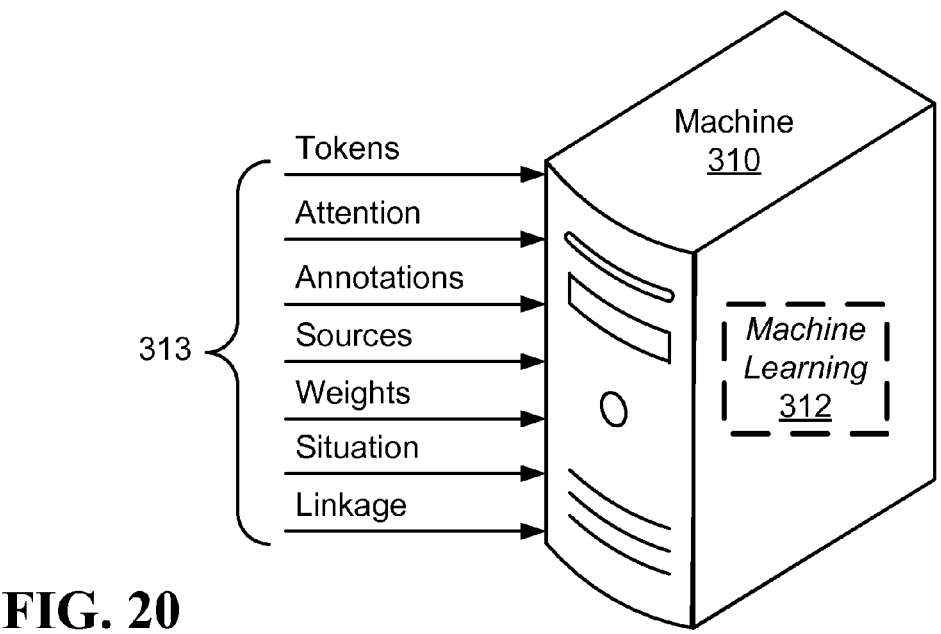
FIG. 20 illustrates a machine having a memory containing data used to train a machine learning based affective response model for a user.
Figure 21:
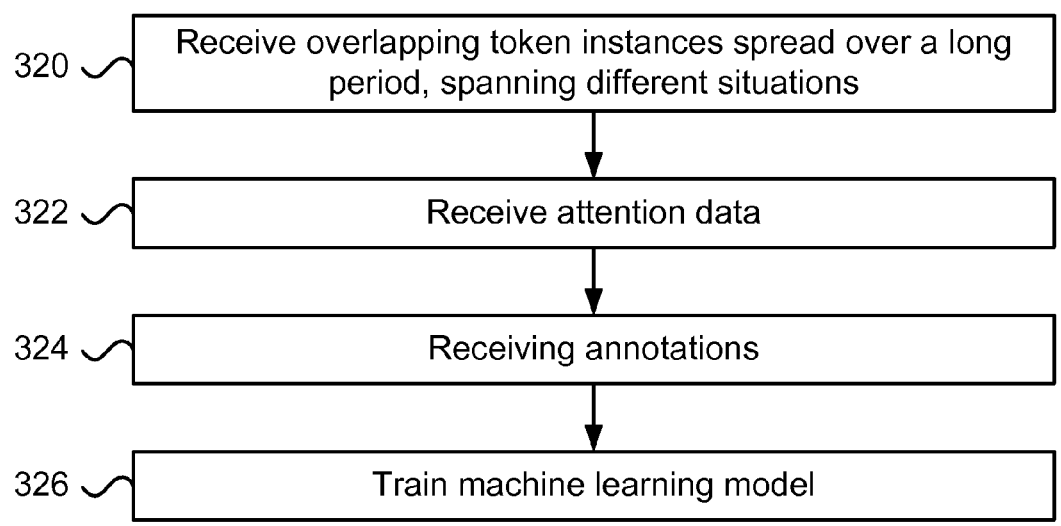
FIG. 21 illustrates a method in accordance with one embodiment.

FIG. 20 illustrates a machine 310 having a memory containing data used to train a machine learning based affective response model for a user 312 on at least some of the inputs 313. FIG. 21 illustrates one embodiment of a method for generating the machine learning based affective response model 312. The method includes the following steps: In step 320, receiving token instances representing stimuli that influence the user's affective state. The token instances are spread over a long period of time that spans different situations and have overlapping instantiation periods. In step 322, receiving data representing levels of user attention in some of the token instances used to improve the accuracy of the machine learning based affective response model for the user. In step 324, receiving annotations representing emotional states of the user. The annotations are spread over a long period of time that spans different situations. And in step 326, training the machine learning based affective response model for the user on the token instances, the data representing levels of user attention in some of the token instances, and the annotations.

Predictors

In one embodiment, a machine learning-based predictor is trained for predicting the user's response when exposed to token instances. Optionally, the predictor predicts the user's affective response when exposed to the token instances. Optionally, the predictor predicts the values corresponding to one or more of the user's measurement channels. Optionally, the predictor may utilize any known or yet-to-be invented machine learning methods for classification or prediction, which operate on data samples and return a predicted target value.

In one embodiment, a machine learning training procedure is supplied training data comprising of samples and corresponding target values (also referred to as labels). The samples include information derived from token instances. Optionally, samples are derived from temporal windows of token instances, for example, by using a vector representation for the windows. Optionally, the samples are preprocessed in various ways, for example, normalizing, filtering, and/or binning some of the values. Optionally, samples are augmented with additional information, for example, baseline values, user measurement channel values, values describing the distance from a baseline, values describing counts of samples in the temporal window of token instances (e.g., in order to account for saturation), and/or values corresponding to previous instantiation of some of the tokens (e.g., in order to account for habituation). Optionally, some samples are assigned weight values, for example, in order for the machine learning procedures to emphasize them appropriately in the training.

In one embodiment, the data used to create the samples for training a machine learning based predictor is collected by monitoring a user over a long period of time (for instance hours, days, months and even years), and/or while the user is in a large number of different situations. Optionally, the training data is comprised of token instances originating from multiple sources of different types. For example, some token instances comprise representations of elements extracted from digital media content. In another example, some token instances comprise representations of elements extracted from an electromechanical device in physical contact with the user. Optionally, the training data is comprised of some token instances with overlapping instantiation periods, i.e., the user may be simultaneously exposed to a plurality of token instances. Optionally, the user may be simultaneously exposed to a plurality of token instances originating from different token sources and/or different types of token sources.

In one embodiment, a machine learning-based predictor is trained to predict the user's response (which may also be referred to as a target value) when exposed to token instances. Optionally, the response is given in the form of a value of a categorical variable. Optionally, the response is given in the form of a value for scalar variable, such as an integer or real value. Optionally, the response is given in the form of a value of a multidimensional variable or vector.

In one embodiment, a machine learning-based predictor for a user's multidimensional response value may be obtained by merging the outcome of multiple predictors for single dimensional response values, corresponding to individual dimensions of a desired multidimensional response. In some cases, there are correlations between the dimensions of a multidimensional response, such as when the response is an affective response or the response is given in the form of user measurement channel values. Therefore, in one embodiment, the multidimensional response is predicted in a two-stage approach. First, a model for each response dimension is trained independently. In the second stage, a model for each response dimension is trained, wherein the response values for the other dimensions are also provided as an input. The final response is obtained by merging the results from the predictions of the models trained at the second stage. In one example, a multidimensional predictor utilizes single dimensional predictors using the method of output-associative fusion, as described in Nicolaou, M. A., Gunes, H., & Pantic, M. (2011) Continuous Prediction of Spontaneous Affect from Multiple Cues and Modalities in Valence—Arousal Space, IEEE Transactions on Affective Computing, where the correlations between dimensions is leveraged to increase the accuracy of a multidimensional prediction.

In one embodiment, some of the samples used for training the machine learning-based predictor do not have corresponding target values (also referred to as labels). In this case, training may be performed using semi-supervised machine learning techniques. Often semi-supervised methods are able utilize unlabeled samples, in order to gain additional accuracy. Optionally, different methods for semi-supervised training are used to train more accurate predictors, such as the methods discussed in Zhu, X. and Goldberg, A. (2009), Introduction to semi-supervised learning. Morgan & Claypool Publishers, which describe various approaches in which the unlabeled data may be utilized in the learning process, such as (i) mixture models in which the model's parameters are learned also from the unlabeled data using an expectation maximization (EM) algorithm; (ii) self-training (also referred to as bootstrapping), wherein the predictor or classifier is used to assign target values to unlabeled samples, and is thus able to increase the body of labeled samples from which it can learn; (iii) co-training, wherein two or more learners are trained on a set of examples and used to classify unlabeled samples, but with each learner using a different sets of features.

In one embodiment, in which there are many more training samples than target values, the target values may be collected or received intermittently. Optionally, by "intermittently", it is meant that there are periods of times in which target values (labels) are available, and those periods may be separated by periods of time in which target values are not available. Optionally, by "intermittently", it is meant that the target values may appear sporadically at times, i.e., single target values may be available at certain times, separated by periods in which there are no target values available.

In one embodiment, the machine learning-based predictor for the user's response to tokens is created by using ensemble methods that aggregate the results of different models; for example, methods applying boosting or bagging.

In one embodiment, various dimensionality reduction and/or feature extraction methods may be used to reduce the data's dimensionality, such as Principal Component Analysis (PCA), or Local Linear Embedding (LLE). In one embodiment, feature selection methods may be used in order to reduce the data dimensionality and remove dimensions that are irrelevant to the prediction task.

In one embodiment, a Naive Bayes model is trained on labeled training samples. Optionally, the Naive Bayes model is used as a classifier, returning a categorical response value. Optionally, some of the variables in the samples are converted into binary variables, such that all non-zero values are set to one. Optionally, the values of the variables in the input data are binned, such that the variables are converted to discrete multinomial variables. Optionally, some of the variables are assumed to be distributed according to a parametric distribution such as the Normal distribution. Optionally, the trained Naive Bayes model is comprised of class prior probabilities and class conditional probabilities; the class prior probabilities describe the prior probability for a sample to be labeled with a specific category; the class conditional probabilities describe the probability for a variable to have a specific value given the sample is labeled with a specific label (class).

In one embodiment, a Naive Bayes model is trained using both labeled and unlabeled data. Optionally, the Naive Bayes model is used as a classifier that predicts a categorical response value. Optionally, the model is trained using an Expectation Maximization algorithm comprising the following steps:

(i) Training a Naive Bayes classifier using only the labeled samples to obtain a set of parameters that includes the initial class prior and class conditional probabilities.

(ii) Repeating the following Expectation-step and Maximization-step while the classifier's parameters improve the performance, e.g., by reducing the classification error rate on an independent test set: (a) Expectation-step: Using the current classifier parameters, compute for all samples (both labeled and unlabeled) the probability that the samples belong to each of the classes (these probabilities are referred to as "component probabilities"). (b) Maximization-step: Re-estimate the classifier parameters from all samples using the updated component probabilities.

(iii) Outputting the parameters with which classifier obtained the best performance.

Optionally, the Naive Bayes model trained in a semi-supervised method comprises class prior probabilities and class conditional probabilities; the class prior probabilities describe the prior probability for a sample to be labeled with a specific category; the class conditional probabilities describe the probability for a variable to have a specific value given the sample is labeled with a specific label (class).

In one embodiment, a maximum entropy model is trained to be used as a classifier that predicts a categorical response value. Maximum entropy models are a multiclass extension of logistic regression models. Optionally, a maximal entropy model uses feature functions of the form f(x,c), where x is an input variable and c is a class. For example, for a certain sample, the value of f(x,c) may behave as follow, if the sample is labeled by class c, f(x,c) returns the value of feature x, otherwise f(x,c) returns 0. A maximal entropy model comprises weighting parameters $\lambda_{i,j}$, for $1 \leq i \leq N$, and $1 \leq j \leq C$, that correspond to the N×C feature functions used to train the model (assuming the input vectors have N features and there are C categories to predict). More information on Maximum entropy models and their training is available, for example, in Berger, A. L. Della Pietre, S. A. Della Pietra, V. J. (1996) Maximum Entropy Approach to Natural Language Processing. Computational Linguistics, 22(1), pages 39-72.

In one embodiment, a neural network model is trained in order to serve as a predictor of a categorical response value, a single dimensional response value, or a multidimensional response value. Optionally, the neural network comprises of an input layer or neurons, one or more hidden layers of neurons, and an output layer of neurons. Optionally, the neural network may utilize a feedforward topology. Alternatively, the neural network may be an Elman/Jordan recurrent neural network trained using back-propagation.

In one embodiment, a random forest is trained in order to serve as a classifier. A random forest is an ensemble method that aggregates the predictions of many decision trees. More information on random forests is available, for example, in Breiman, Leo (2001). "Random Forests". Machine Learning 45 (1): 5-32.

In one embodiment, a regression model is used as a predictor of a single dimensional response variable. Optionally, the regression technique used is Ordinary least squares. Optionally, the regression technique used is weighted least squares (to account for weighted input samples). Optionally, the regression technique used is least angle regression (which has been shown to work well with high-dimensional data). Optionally, the regression technique used is LASSO regression (which includes regularization terms).

In one embodiment, the regression may take the form $y = X \cdot \beta + \epsilon$, where y is the response vector (for example, emotional state arousal values), X is a matrix whose rows are the vectors representing the samples (for example, vector representations of temporal windows of token instances), $\beta$ is the model parameter vector, and $\epsilon$ is the error vector. The goal of the training is to minimize the squared error of the difference between y and $X \cdot \beta$.

In one embodiment, regression models are used for predicting a multidimensional response value. Optionally, the multidimensional prediction is done by training separate regression models for each of the predicted dimensions. Optionally, Multiple Response Regression may be used, as described in Hastie, T., Tibshirani, R. and Friedman, J. (2001) The Elements of Statistical Learning, Springer, which describes a regression technique that can leverage the correlations between different dimensions of the response values.

In one embodiment, a support vector machine for regression (SVR) is used as a predictor for a single dimensional response value.

In one embodiment, a Support Vector Machine (SVM) is trained in order to be a predictor for a categorical response value.

In one embodiment, an Input-Output Hidden Markov Model (IOHMM) is trained in order to be a predictor of a multidimensional response value. Like a Hidden Markov Model (HMM), an IOHMM has hidden discrete state variables. However, unlike HMM's, IOHMM also receives input values (in addition to emitting outputs). Each state may use a predictor, such as a neural network to predict the output values given the input values. In addition, similar to HMMs, the model also maintains transition probabilities to move between states. More information on IOHMMs is available, for example, in Bengio, Y. and Frasconi, P. (1996). Input/output HMMs for sequence processing. IEEE Trans. on Neural Networks, 7(5):1231-1249. Optionally, some of the training samples may have state assignments, for example, corresponding to situation identifiers, which can be used to initialize some of the parameters in the expectation maximization algorithm used to train the model's parameters.

Predictors for Response to Streams of Tokens

In some embodiments, it is necessary to predict a response of the user to being exposed to one or more token instances, e.g., during interactions in the physical and/or digital world. In one, example the token instances may belong to one or more temporal windows of token instances. Conceptually, the token instances may be viewed as a stream of token instances to which the user is exposed. Below are described various embodiments that may be used to predict the response of the user to a stream of token instances that includes one or more token instances. Optionally, the predicted response of the user the user's affective response (e.g., as expressed as an emotional state and/or change to an emotional state). Optionally, the predicted response of the user is a value of a measurement channel of the user and/or a change to a value of a measurement channel of the user. Optionally, predicting the response of the user is done utilizing a machine learning-based predictor.

FIG. 22 illustrates one embodiment of a system that trains an emotional state model 122. The sample generator 114 receives token instances 110, and optionally information regarding the user's baseline 112 and/or other input 113 such as data regarding the situation, data concerning habituation (e.g., previous exposure to token instances), and/or saturation data (e.g., data concerning the exposure of the user to the token instances 110 and/or other stimuli). The sample generator 114 utilizes the data it receives to generate a representation of the token instances and the other values inputs 116. For example, the representation of the token instances and the other values inputs 116 may be a vector of values (e.g., numeric values or categorial values). Target value generator 104 receives the user measurement channels 102 of the user, and optionally other inputs 103. The Target value generator 104 generates affective response annotations 106. For example, the affective response annotations 106 may correspond to emotional states and/or changes to emotional states. A machine learning trainer 120 receives the representation of the token instances and the other value inputs 116 and the affective response annotations 106, and generates the emotional state model 122. Optionally, the emotional state model 122 includes parameter values (e.g., regression weights) and/or a representation of a subset of the samples (e.g., samples that serve as support vectors for a support vector machine).

FIG. 23 illustrates one embodiment of a system in which the emotional state model 112 is used to predict an emotional state annotation 152. A sample processor 144 receives inputs that may include token instances 140, and optionally information regarding the user's baseline 142 and/or other input 143 such as data regarding the situation, data concerning habituation (e.g., previous exposure to token instances), and/or saturation data (e.g., data concerning the exposure of the user to the token instances 110 and/or other stimuli). The sample processor 144 utilizes the data it receives to generate a representation of the token instances and the other values inputs 146. For example, the representation of the token instances and the other values inputs 116 may be a vector of values (e.g., numeric values or categorial values). The representation of the token instances and the other values inputs 146 is provided as input the a machine learning predictor 150. The machine learning predictor utilizes the emotional state model 122 in order to predict the emotional state annotation 152 that corresponds to representation of the token instances and the other values inputs 146. For example, the emotional state annotation 152 may correspond to an emotional state (e.g., happiness) and/or to a change to an emotional state (e.g., increased excitement).

FIG. 24 illustrates one embodiment of a system that trains a user measurement model 172. The sample generator 114 receives token instances 110, and optionally information regarding the user's baseline 112 and/or other input 113 such as data regarding the situation, data concerning habituation (e.g., previous exposure to token instances), and/or saturation data (e.g., data concerning the exposure of the user to the token instances 110 and/or other stimuli). The sample generator 114 utilizes the data it receives to generate a representation of the token instances and the other values inputs 116. For example, the representation of the token instances and the other values inputs 116 may be a vector of values (e.g., numeric values or categorial values). A machine learning trainer 170 receives the representation of the token instances and the other value inputs 116 and the affective response annotations 106, and values of a user measurement channel 102 that serve as target values. The machine learning trainer utilizes the received data to generate the user measurement model 172. Optionally, the user measurement model 172 includes parameter values (e.g., regression weights) and/or a representation of a subset of the samples (e.g., samples that serve as support vectors for a support vector machine).

FIG. 25 illustrates one embodiment of a system in which the user measurement model 172 is used to predict a user measurement prediction 182. A sample processor 144 receives inputs that may include token instances 140, and optionally information regarding the user's baseline 142 and/or or other input 143 such as data regarding the situation, data concerning habituation (e.g., previous exposure to token instances), and/or saturation data (e.g., data concerning the exposure of the user to the token instances 110 and/or other stimuli). The sample processor 144 utilizes the data it receives to generate a representation of the token instances and the other values inputs 146. For example, the representation of the token instances and the other values inputs 116 may be a vector of values (e.g., numeric values or categorial values). The representation of the token instances and the other values inputs 146 is provided as input the a machine learning predictor 180. The machine learning predictor utilizes the user measurement model 172 in order to predict the user measurement prediction 182 that corresponds to representation of the token instances and the other values inputs 146. For example, the user measurement prediction 182 may correspond to user measurement channel value (e.g., heart rate, or an image of a smile) and/or change to a user measurement channel value (e.g., increase to heart rate and/or perspiration).

In one embodiment, training data used to train a machine learning-based predictor for a user's response after being exposed to a stream of token instances is collected by monitoring the user when he/she is exposed to a plurality of streams of token instances, optionally with the streams have varying durations. Optionally, the training data is collected by monitoring the user over a long period of time (for instance hours, days, months and even years), and/or when the user was in a large number of different situations. Optionally, the training data is comprised of token instances originating from multiple sources of different types. For example, some token instances comprise representations of elements extracted from digital media content. In another example, some token instances comprise representations of elements extracted from an electromechanical device in physical contact with the user. Optionally, the training data is comprised of some token instances with overlapping instantiation periods, i.e., the user may be simultaneously exposed to a plurality of token instances. Optionally, the user may be simultaneously exposed to a plurality of token instances with overlapping instantiation periods, possibly originating from different token sources and/or different types of token sources.

The following three methods (A, B, C) can utilize the aforementioned training data to train a machine learning-based predictor to predict the user's response after being exposed to a stream of token instances.

(A) In one embodiment, a method for predicting a user's response after being exposed to a stream of token instances represents a stream of token instances using a single temporal window of token instances. The stream of token instances is converted into a single vector representing a temporal window of token instances with a length approximately matching the duration of the token instance stream. Optionally, some of the values in the vector representing the temporal window of token instances, such as token instance weights, are normalized according to the duration of the stream of token instances. For example, the weights are divided by the duration of the stream in minutes, in order to be compatible with windows representing streams of other durations. Optionally, the duration of the token instance stream is provided as an additional input value as part of the vector representation of the temporal window of token instances. Optionally, additional information is incorporated into the vectors of the training data, such as variables identifying the situation in which the user is at the time, variables describing a baseline level, and/or variable describing a distance of a variable from a baseline value.

In one embodiment, the training data comprising a plurality of token instance streams to which the user was exposed is converted into temporal window of token instances, of possibly variable durations (e.g., one window per token instance stream), and the user's response is noted before and after the exposure to the stream of tokens. Optionally, the user's response before the exposure to the stream of tokens may be provided as part of the sample's data, while the response after the exposure to the token instance stream may serve as the target value for prediction. Optionally, the difference between the response after the exposure and the response before the exposure to the stream of token instances is used as the target value for prediction.

In one embodiment, training data is collected and used to train a machine learning-based predictor such as a recurrent neural network, support vector machine for regression, or regression model. Given a new stream of tokens, and optionally, the user's response before exposure, the trained predictor may be used to predict the user's response after an exposure to the stream of token instances, by converting the stream of token instances into a single vector representing a temporal window of token instances, and returning the predictor's result on the single vector.

(B) In one embodiment, a method for predicting a user's response after being exposed to a stream of token instances uses a representation for the stream of token instances as multiple vectors; wherein the vectors represent consecutive temporal window of token instances of a substantially fixed duration, for example 10 seconds. Optionally, the representation for the stream of token instances comprises multiple vectors corresponding to temporal windows of token instances of varying duration, for example, where each temporal window of token instances essentially describes a certain event or instance such as a scene in a movie. Training data comprising a plurality of token instance streams to which the user was exposed is collected and converted into temporal windows of token instances. The user's response is noted both at the beginning of temporal windows of token instance, and at their end. Optionally, the user's response at the beginning of the window may be provided as part of the sample vector data, while the response at the end of the window may serve as the target value for prediction. Optionally, the difference between the response at the beginning and end of the window may be used as the target value for prediction. Optionally, additional information is incorporated into the vectors of the training data, such as variables identifying the situation in which the user is at the time, and/or variables describing a predicted baseline level.

In one embodiment, training data is collected and used to train a machine learning-based predictor such as a recurrent neural network, support vector machine for regression, or regression model. Given a new stream of tokens, and optionally, the user's response before exposure, the model may be used to predict the user's response after the exposure to the stream of token instances. The stream of token instances is converted into a sequence of vectors representing consecutive temporal windows of token instances of an essentially same fixed duration. The prediction may proceed as follows. At the first step, the value of the user's response before exposure to the stream of tokens instances is used for the user's response value at the beginning of the first window. The user's response value after exposure to the first window is then predicted using the trained predictor. This predicted response then serves as the value of the user's response before the exposure to the second window and so on. Thus, the predicted response to window i serves as the initial response value of window i+1. This process proceeds until the user's response, after being exposed to the token instances of the last window, is predicted. This last predicted response value is returned as the user's response to being exposed to the entire stream of token instances.

Figure 26:
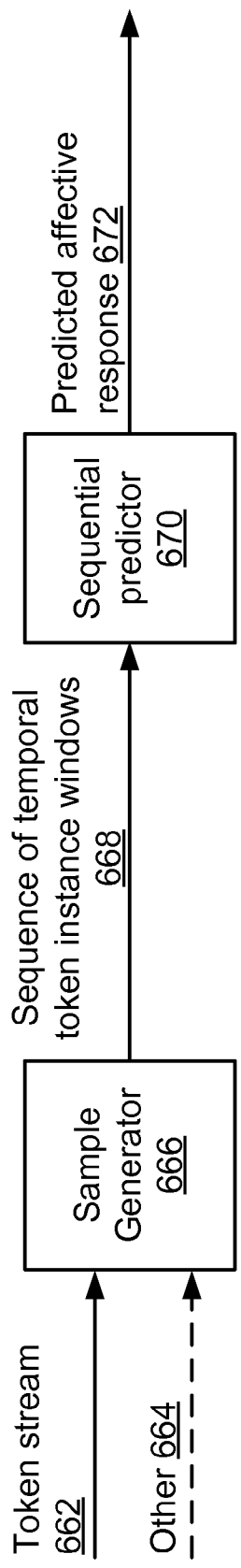
FIG. 26 illustrates an affective response predictor for a stream of token instances.

FIG. 26 illustrates one embodiment of a system that predicts an affective response to a stream of token instances. A sample generator 666 is configured to receive a stream of token instances 662 and possibly other inputs 664 such as information regarding a situation and/or baseline values. The sample generator 666 produces samples corresponding to a sequence temporal windows of token instances 668. For example, each sample of a temporal sequence of token instances may correspond to the token instances to which the user was exposed during a certain period (e.g., a fixed duration such as 10 seconds or a logical duration such as a scene in a video clip). The samples corresponding to a sequence temporal windows of token instances 668 are provided to a machine learning-based sequential predictor 670 that predicts the affective response to the sequence of windows by sequentially predicting the response to each window and optionally using a predicted response to a previous window as the initial response for the next window.

(C) In one embodiment, a method for predicting a user's response after being exposed to a stream of token instances uses a Hidden Markov Model (HMM). This method uses categorical state values to represent the user response, for example, emotional state categories such as anger, happiness, sadness, excitement, surprise. A stream of token instances is represented as multiple vectors; wherein the vectors represent consecutive temporal windows of token instances of a fixed duration, for example 10 seconds. Optionally, the representation for the stream of token instances comprises multiple vectors corresponding to temporal windows of token instances of varying duration, for example, where each temporal window of token instances essentially describes a certain event or instance such as a scene in a movie. Training data comprising one or more token instance streams to which the user was exposed is collected and converted into temporal windows of token instances. The user's categorical state value during each window is also noted and used as the label for the windows. Optionally, additional information is incorporated into the samples of the training data, such as variables identifying the situation in which the user is at the time, and/or variables describing a predicted baseline level.

In one embodiment, collected training data is used to train a Hidden Markov Model (HMM), in which the hidden states represent the categorical state values used to label the windows and the emitted symbols are the token instances observed in each window. The training data comprises sets of sequences of windows created from streams of token instances. Training the HMM involves finding a maximum likelihood estimate for parameters such as transition probabilities between states and the emission probabilities (the probability of observing token instances in the different states). Optionally, the parameters are set using a forward-backward algorithm, such as the Baum-Welch algorithm that uses an Expectation Maximization approach. Given a new stream of tokens, the HMM can be used to predict the user's response after being exposure to the stream as follows. First, the stream is converted into a sequence of vectors representing temporal windows of token instances of a fixed duration. Then a dynamic programming algorithm, such as the Viterbi algorithm, may be used to predict the most likely final state, in addition to the most likely path of states in which the user may be if exposed to the stream of token instances. Optionally, the user's initial state, which is the response level before exposure to the stream of token instances, may be used as the first state in the predicted path of states. Otherwise, the dynamic programming algorithm may consider all states as possible initial states according to prior probabilities learned during the HMM model training.

Figure 27:
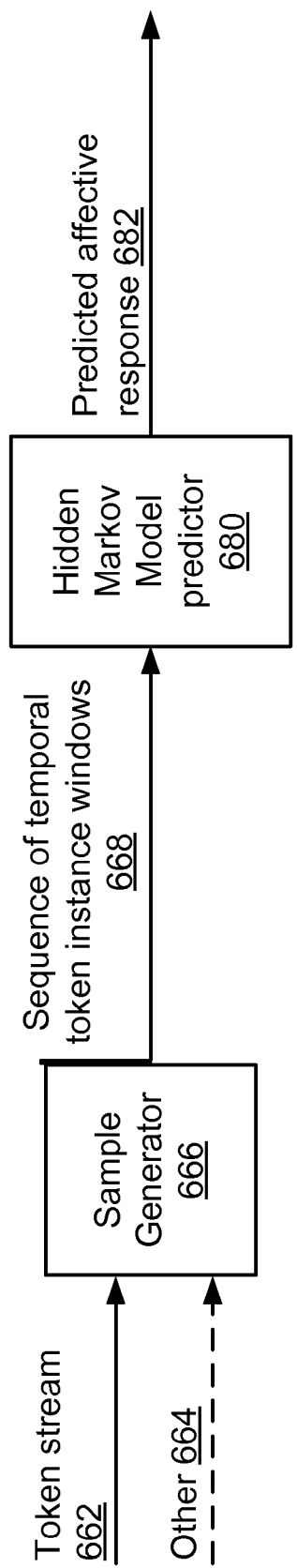
FIG. 27 illustrates an affective response predictor for stream of token instances based on HMM.

FIG. 27 illustrates one embodiment of a system that predicts an affective response to a stream of token instances. A sample generator 666 is configured to receive a stream of token instances 662 and possibly other inputs 664 such as information regarding a situation and/or baseline values. The sample generator 666 produces samples corresponding to a sequence temporal windows of token instances 668. For example, each sample of a temporal sequence of token instances may correspond to the token instances to which the user was exposed during a certain period (e.g., a fixed duration such as 10 seconds or a logical duration such as a scene in a video clip). The samples corresponding to a sequence of temporal windows of token instances 668 are provided to a Hidden Markov Model-based predictor 680, which may use a dynamic programming algorithm to predict the most likely affective response to being exposed to the stream of tokens described by the sequence of temporal windows of token instances 668.

Predicting Response from User Measurements

In one embodiment, machine learning algorithms are trained on data extracted from user measurement channels to create a model for predicting a user's emotional state at a required point in time. Optionally, data comprising token instances may also be used for training these models.

In one embodiment, models for a user's emotional state are periodically re-trained and/or updated to reflect new data that has been accumulated. Optionally, the models are re-trained following an event where the prediction error exceeds a threshold, and/or following an event where the performance deteriorates below a threshold.

In one embodiment, the data extracted from the user measurements may be normalized with respect to the user's baseline value for that time. Optionally, the normalization is performed periodically, such as every few hours or every day. Optionally, the normalization is performed following a large change in one or more of the user measurement channels, such as resulting from a situation change.

In one embodiment, a baseline function for the annotated emotional state may be used as an input to a machine learning algorithm for predicting the user's emotional state.

Some embodiments may utilize known and/or yet to be discovered systems to predict an emotional state from values from a single or multiple user measurement channels. The predictions may use various methods for emotional representation, such as categorical, dimensional, and/or appraisal-based. Examples of emotional state prediction methods that may be use include: (i) physiological-based predictors as described in Table 2 in van den Broek et al. (2009); (ii) Audio- and visual-based predictors as described in Tables 2-4 in Zeng, Z., et al. (2009); (iii) additional predictors for the emotional state that are both single-channel (unimodal) or multichannel (multimodal) as described in Tables 2, and 4 in (Gunes & Pantic, 2010); and/or (iv) predictors of the emotional state from low-level media features, such as described in Hanjalic, A., & Xu, L.-Q. (2005), Affective video content representation and modeling. IEEE Transactions on Multimedia, 7(1), 143-154.

In one embodiment, the machine learning system for predicting a user's emotional state may need to make decisions from multiple user measurement channels. Therefore, at some stage, the data from the different user measurement channels may need to be fused. Optionally, different types of data fusion may be employed, for example feature-level fusion, decision-level fusion or model-level fusion, as discussed in Nicolaou, M. A., Gunes, H., & Pantic, M. (2011), Continuous Prediction of Spontaneous Affect from Multiple Cues and Modalities in Valence-Arousal Space, IEEE Transactions on Affective Computing.

In one embodiment, the user's emotional state at certain time points is labeled by monitoring the user. In one example, the user is presented with sensual stimuli that are known to predict certain emotions, such as images, videos, and/or sounds that are known to elicit an emotional response. In another example, the user is presented with media clips which he/she views and after each one reports the elicited emotions (e.g., positive, negative, or neutral), or is asked to provide values in a dimensional space, for example in the Arousal/Valence dimensions. Optionally, users may use systems that aid emotional state annotation, for example, a system that describes various emotional states using cartoon images. In yet another example, the user may have the option to create training samples, for instance, by indicating that what he/she just saw gave a good or bad feeling. Alternatively, the user may be asked to imagine scenarios in which certain emotions are felt, and the user measurements at that time may be used as training sample.

In one embodiment, a pre-trained model for predicting the emotional state from user channel measurements is used to label the user's emotional state at certain time points. Optionally, the system is trained on data from multiple users.

In one embodiment, a pool of models for predicting the emotional state from user channel measurements may be available to label the user's emotional state. Optionally, each model was trained using a single individual. In order to accurately label the user's emotional state, a model belonging to a person similar to the user is selected for the labeling process. The similarity between people may be determined in several ways, for example, by observing similar patterns in the values of their user measurement channels and/or token instances to which they were exposed, by observing similar demographic and/or educational characteristics, and/or by semantic analysis of speech, text, and/or video content created by the people determine similar attitudes and/or world views.

In one embodiment, one or more methods are used to label an initial set of training points with the user's emotional state. These labeled points, in turn, are used to train the user's model for predicting the emotional state. Following that, several rounds of bootstrapping may ensue, in which the user's model is used to label additional points, which are then used to retrain the user's model. With each iteration, the user's model may better bit the training data. Optionally, the model's performance is tested on an independent test set, which was labeled using a different model (for example trained on another portion of the data set), in order to prevent overfitting. Optionally, other semi-supervised training methods may be used to create the model for predicting a user's emotional state.

Libraries

In one embodiment, a machine learning-based user response model is analyzed in order to generate a library of the user's expected response to tokens representing stimuli to which the user may be exposed. In one embodiment, the user's response is expressed as an expected affective (emotional) response and/or expected change to the user's affective response. In one embodiment, the response is expressed as the expected value and/or change in value for one or more user measurement channels. Optionally, the training data used to generate the model comprises of samples generated from temporal windows of token instances and target values corresponding to the temporal windows of token instances, which represent the user's response to the token instances from the temporal window of token instances.

In one embodiment, a library of the user's expected response to tokens (i.e., the user's expected response when exposed to one or more token instances), comprises various values and/or parameters extracted from the user's machine learning-based user response model. Optionally, the extracted values and/or parameters indicate the type and/or extent of the user's response to some tokens. Optionally, the extracted values and/or parameters indicate characteristics of the user's response dynamics, for example, how the user is affected by phenomena such as saturation and/or habituation, how fast the user's state returns to baseline levels, how the response changes when the baseline is at different levels (such as when the user is aroused vs. not aroused).

In one embodiment, a library comprises values generated by monitoring the results of experiments in which a user's machine learning-based user response model was run on various data samples. For example, experiments in which specific samples (for example, with specific token instances) were run through the model in order to gain insights into the user's response to the specific token instances. Optionally, the experiments may involve perturbed data, for example, by modifying the weight of certain token instance in order to observe how the response changes as a function of the modified input level.

In one embodiment, a library of the user's expected response to tokens is generated, with the response being expressed as a multidimensional value. For example, the response value may represent an emotional state as a point or vector in a multidimensional space. In another example, the response may be the value of a plurality of user measurement channels. Optionally, the library of expected responses to tokens may include response values expressed as multidimensional values, for example a point or a vector in a multidimensional space. Optionally, the library may include separate responses for the token for each of dimension in the multidimensional space used to represent the response value.

In one embodiment, the machine learning-based user response model used to generate the library of the user's expected response to tokens is trained on data collected by monitoring a user over a long period of time (for instance hours, days, months and even years), and/or when the user is in a large number of different situations. Optionally, the training data is comprised of token instances originating from multiple sources of different types. For example, some token instances comprise representations of elements extracted from digital media content. In another example, some token instances comprise representations of elements extracted from an electromechanical device in physical contact with the user. Optionally, the training data is comprised of some token instances with overlapping instantiation periods, i.e., the user may be simultaneously exposed to a plurality of token instances. Optionally, the user may be simultaneously exposed to a plurality of token instances originating from different token sources and/or different types of token sources. Optionally, some of the token instances originate from different token sources, and are detected by the user using essentially different sensory pathways (i.e., routes that conduct information to the conscious cortex of the brain).

In one embodiment, the training data collected by monitoring the user is collected during periods in which the user is in a large number of different situations. Optionally, the data is partitioned into multiple datasets according to the different sets of situations in which the user was in when the data was collected. Optionally, each partitioned training dataset is used to train a separate situation-dependent machine learning-based user response model, from which a situation-dependent library may be derived, which describes the user's expected response to tokens when the user is in a specific situation.

In one embodiment, data related to previous instantiations of tokens is added to some of the samples in the training data. This data is added in order for the trained machine learning-based user response model to reflect the influences of habituation. Thus, the library generated from the machine learning model may be considered a habituation-compensated library, which accounts for the influence of habituation on the user's response to some of the token instances. In some cases, habituation occurs when the user is repeatedly exposed to the same, or similar, token instances, and may lead to a reduced response on the part of the user when exposed to those token instances. By contrast, in some cases the user's response may gradually strengthen if repeatedly exposed to token instances that are likely to generate an emotional response (for example, repeated exposure to images of a disliked politician).

To account for the aforementioned possible influence of the user's previous exposures to tokens, in one embodiment, certain variables may be added explicitly to some of the training samples. Optionally, the added variables may express for some of the tokens information such as the number of times the token was previously instantiated in a given time period (for example, the last minute, hour, day, or month), the sum of the weight of the previous instantiations of the token in the given time period, and/or the time since the last instantiation of the token. Optionally, the habituation-related information may be implicit, for example by including in the sample multiple variables corresponding to individual instantiations of the same token in order to reflect the fact that the user had multiple (previous) exposures to the token.

In one embodiment, a classifier is provided in order to classify some of the tokens into classes. For example, two token instances representing images of people may be classified into the same class. Optionally, information may be added to some of the training samples, regarding previous instantiations of tokens from certain classes, such as the number of times tokens of a certain class were instantiated in a given time period (for example, the last minute, hour, day, or month), the sum of the weight of the previous instantiations of tokens of a certain class in the given time period, and/or the time since the last instantiation of any token from a certain class.

In one embodiment, data related to the collection of token instances the user is exposed to simultaneously, or over a very short duration (such as a few seconds), is added to some of the samples in the training data. This data is added so the trained machine learning-based user response model, from which the library is generated, will be able to model the influence of saturation on the user's response, and thus creating a saturation-compensated library. In some cases, saturation occurs when the user is exposed to a plurality of token instances, during a very short duration, and may lead to a reduced response on the part of the user (for instance due to sensory overload). Therefore, in one embodiment certain statistics may be added to some of the training samples, comprising information such as the number token instances the user was exposed to simultaneously (or during a short duration such as two seconds) and/or the weight of the token instances the user was exposed to simultaneously (or in the short duration). Optionally, a classifier that assigns tokens to classes based on their type can be used in order to provide statistics on the user's simultaneous (or near simultaneous) exposure to different types of token instances, such as images, sounds, tastes, and/or tactile sensations.

In one embodiment, the machine learning-based user response model used to generate a library of the user's expected response to tokens is trained on data comprising significantly more samples than target values. For example, many of the samples comprising temporal windows of token instances do not have corresponding target values. Thus, most of the samples may be considered unannotated or unlabeled. Optionally, the user's machine learning-based user response model is trained using a semi-supervised machine learning training approach such as self-training, co-training, and/or mixture models trained using expectation maximization. In some cases, the models learned by semi-supervised methods may be more accurate than models learned using only labeled data, since the semi-supervised methods often utilize additional information from the unlabeled data, thus being able to compute things like distributions of feature values more accurately.

In one embodiment, a library of the user's expected response to tokens may be accessed and/or queried using various methods: In one example, the library may be queried via a web-service interface. Optionally, the web-service is provided a user identification number and an affective response, and the service returns the tokens most likely to elicit the desired response. Optionally, the system is provided a token, and the system returns the user's expected response. Optionally, the service is provided a token, and the system returns a different token expected to elicit a similar response from the user.

In one embodiment, a Naive Bayes model is trained in order to create a library of a user's expected affective response to token instances representing stimuli. Optionally, the affective response is expressed using C emotional state categories. Optionally, the library comprises prior probabilities of the form $p(c)$, $1 \leq c \leq C$, and class conditional probabilities of the form $p(k|c)$, where k is an index of a token from 1 to N (total number of tokens). Optionally, the probability $p(c|k)$ is computed using Bayes rule and the prior probabilities and the class conditional probabilities. Optionally, for each class, the tokens are sorted according to decreasing probability $p(c|k)$, thus the library may comprise ranked lists of tokens according to how likely (or unlikely) they are to be correlated with a certain emotional states with the user.

In one embodiment, a maximum entropy model is trained in order to create a library of the use's expected response to token instances representing stimuli. Optionally, the model comprises the parameters $\lambda i,j$, for $1 \leq i \leq N$, and $1 \leq j \leq C$, that correspond to the N×C feature functions used to train the model (assuming the input vectors have N features and there are C emotional state categories to classify to), and creating j lists of the form $\lambda 1,j \ldots \lambda N,j$, one for each emotional state class $j=1 \ldots C$. Optionally, For each class $j=1 \ldots C$ the parameters $\lambda 1,j \ldots \lambda N,j$ are sorted according to decreasing values; the top of the list (most positive $\lambda i,j$ values) represents the most positively correlated token instances with the class (i.e., being exposed to these token instances increases the probability of being in emotional state class j); the bottom of the list (most negative $\lambda i,j$ values) represents the most negatively correlated token instances with the class (i.e., being exposed to these token instances decreases the probability of being in emotional state class j). Optionally, some input variables (for example, representing token instances) are normalized, for instance to a mean 0 and variance 1, in order to make the weights assigned to feature functions more comparable between token instances.

In one embodiment, a regression model is trained in order to create a library of the user's expected single dimensional real-valued response to token instances representing stimuli. Optionally, the model comprises the regression parameters $\beta i$, for $1 \leq i \leq N$, that correspond to the N possible token instances included in the model. Optionally, the parameters $\beta 1, \ldots \beta N$ are sorted; the top of the list (most positive $\beta i$ values) represents the token instances that most increase the response variable's value; the bottom of the list (most negative $\beta i$ values) represents the most negatively correlated token instances with the class (i.e., being exposed to these token instances decreases the probability of being in emotional state class j). Optionally, some input variables (for example, representing token instances) are normalized, for instance to a mean 0 and variance 1, in order to make the parameters corresponding to different variables more comparable between token instances. Optionally, the regression model is a multidimensional regression, in which case, the response for each dimension may be evaluated in the library separately.

In one embodiment, parameters from the regression model may be used to gain insights into the dynamics of the user's response. In one example, a certain variable in the samples holds the difference between a current state and a predicted baseline state, for instance, the user's arousal level computed by a prediction model using user measurement channel vs. the user's predicted baseline level of arousal. The magnitude of the regression parameter corresponding to this variable can indicate the rate at which the user's arousal level tends to return to baseline levels. By comparing the value of this parameter in the user's model, with the values of the parameter in other people's models, insight can be gained into how the user compares to the general population.

In one embodiment, a neural network model is trained in order to create a library of the use's expected response to token instances representing stimuli. Optionally, the response may be represented by a categorical value, a single dimensional value, or a multidimensional value. Optionally, the neural network may be an Elman/Jordan recurrent neural network trained using back-propagation. Optionally, the model comprises information derived from the analysis of the importance and/or contribution of some of the variables to the predicted response. For example, by utilizing methods such as computing the partial derivatives of the output neurons in the neural network, with respect to the input neurons. In another example, sensitivity analysis may be employed, in which the magnitude of some of the variables in the training data is altered in order to determine the change in the neural network's response value. Optionally, other analysis methods for assessing the importance and/or contribution of input variables in a neural network may be used.

In one embodiment, a library comprises of sorting token instances according to the degree of their contribution to the response value, for example, as expressed by partial derivatives of the neural network's output values (the response), with respect to the input neurons that correspond with token instances. Optionally, the list of tokens may be sorted according to the results of the sensitivity analysis, such as the degree of change each token induces on the response value. Optionally, some input variables (for example, representing token instances) are normalized, for instance to a mean 0 and variance 1, in order to make the parameters corresponding to different variables more comparable between token instances. Optionally, the neural network model used to generate a response, predicts a multidimensional response value, in which case, the response for each dimension may be evaluated in the library separately.

In one embodiment, a random forest model is trained in order to create a library of the user's expected response to token instances representing stimuli. Optionally, the response may be represented by a categorical value, for example an emotional state, or categories representing transitions between emotional states. Optionally, the training data may be used to assess the importance of some of the variables, for example by determining how important they are for classifying samples, and how important they are for classifying data correctly in a specific class. Optionally, this may be done using data permutation tests or the variables' GINI index, as described at http://stat-www.berkeley.edu/users/breiman/RandomForests/cc_home.htm.

In one embodiment, the library may comprise ranked lists or tokens according to their importance toward correct response classification, and towards correct classification to specific response categories. Optionally, some input variables (for example, representing token instances) are normalized, for instance to a mean 0 and variance 1, in order to make the parameters corresponding to different variables more comparable between token instances.

Figure 28:
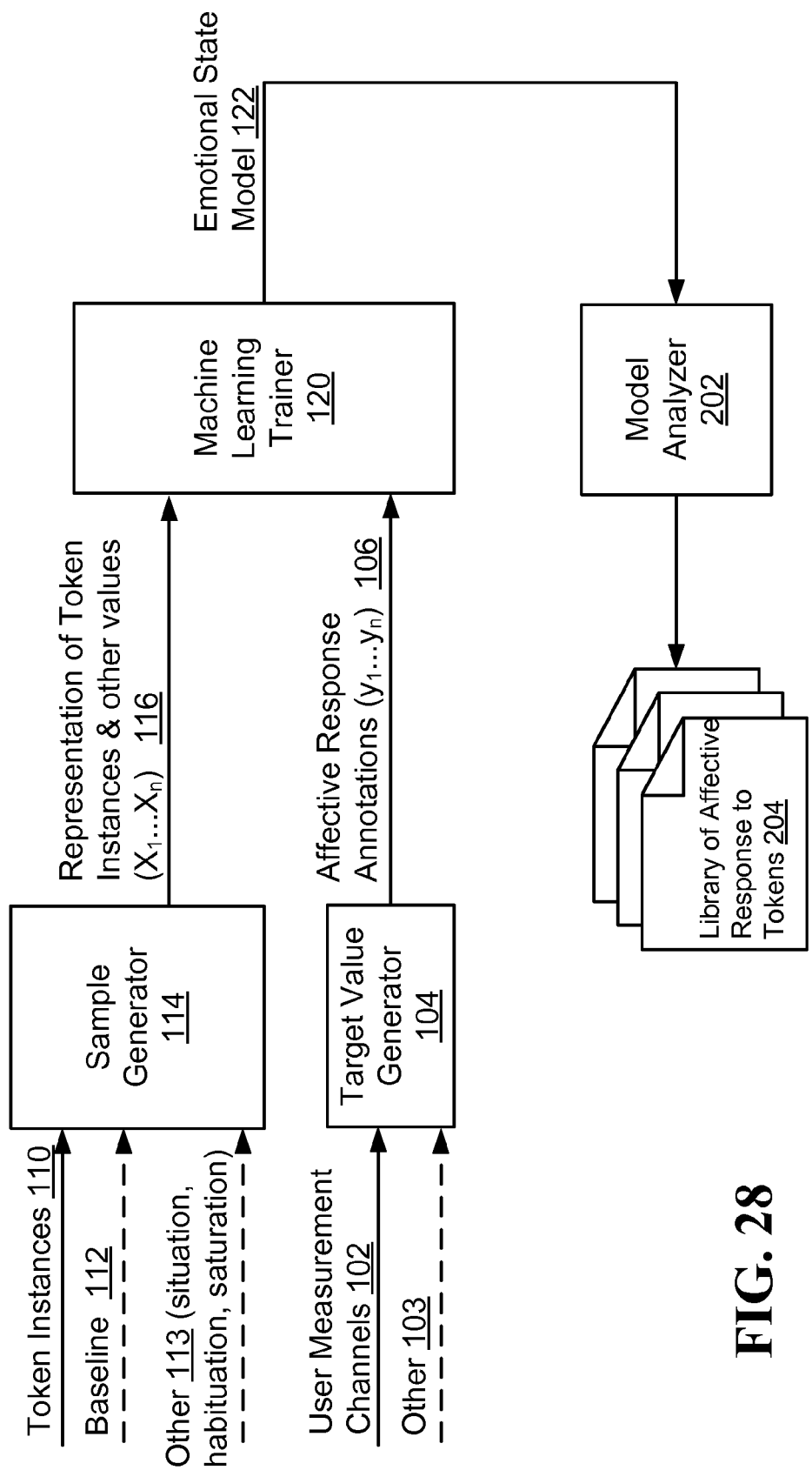
FIG. 28 illustrates an affective response library from machine learning.

FIG. 28 illustrates a machine learning based system for generating a library of affective response to tokens 204. Sample generator 114 receives token instances 110, and optionally other inputs 113 that may include for example the user's baseline 112, situation data, habituation data, and/or saturation data. The sample generator 114 generates a representation of the token instances and the other value inputs 116. Target value generator 104 receives the user measurement channels 102 of the user, and optionally other inputs 103. The Target value generator 104 generates affective response annotations 106. A machine learning trainer 120 receives the representation of the token instances and the other value inputs 116 and the affective response annotations 106, and generates an emotional state model 122 that is analyzed by a model analyzer 202 to generate the library of affective response to tokens 204.

Figure 29:
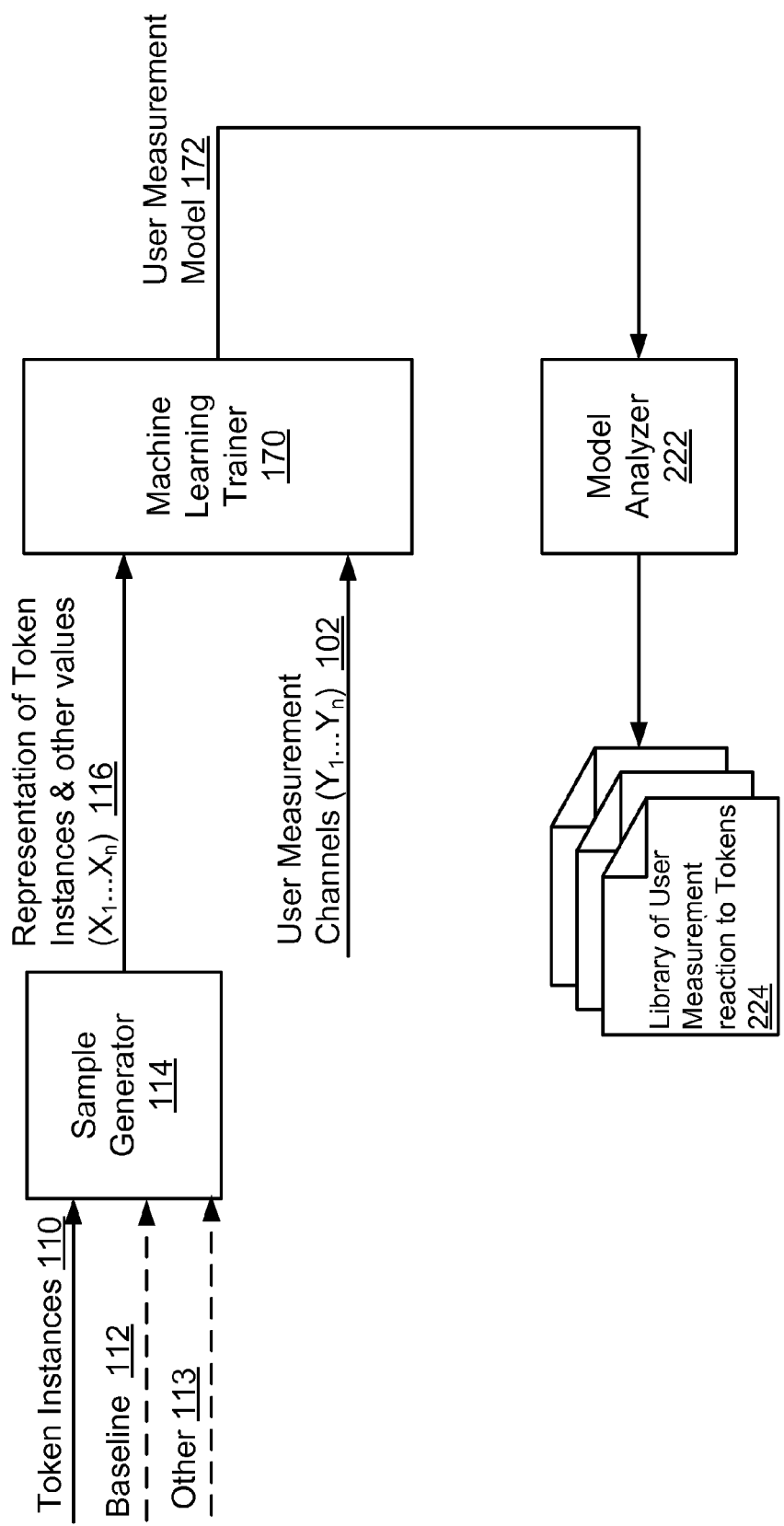
FIG. 29 illustrates a measurement library from machine learning.

FIG. 29 illustrates a machine learning based system for generating a library of user measurement reaction to tokens 224. A machine learning trainer 170 receives the representation of the token instances and the other value inputs 116 and the user measurement channels 102, and generates user measurement model 172 that is analyzed by a model analyzer 222 to generate the library of user measurement reaction to tokens 224.

Figure 30:
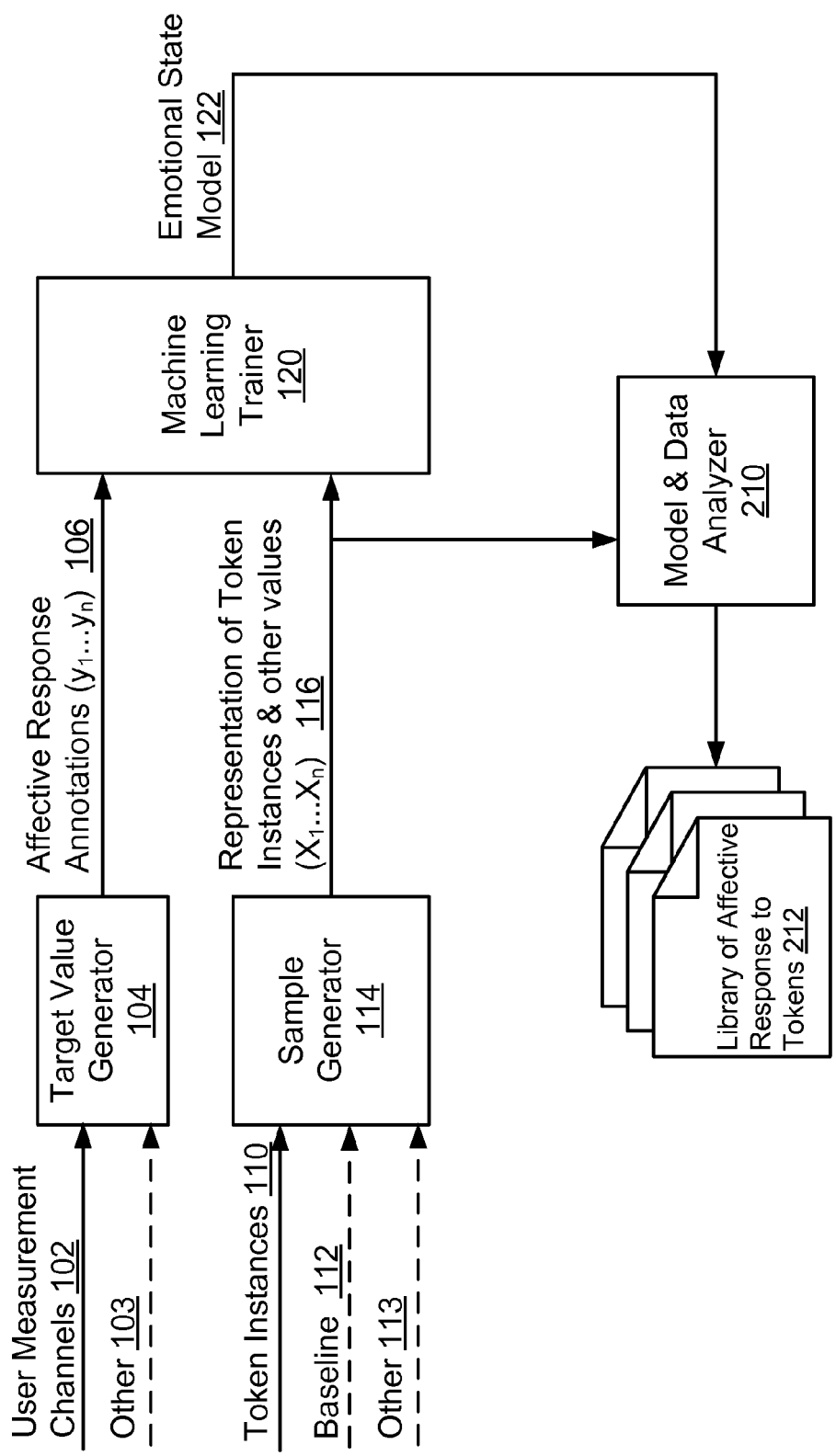
FIG. 30 illustrates an affective response library with input base dynamic analysis.

FIG. 30 illustrates a machine learning based system with input base dynamic analysis for generating a library of affective response to tokens 212. Sample generator 114 receives token instances 110, and optionally other inputs 113 that may include for example the user's baseline 112, situation data, habituation data, and/or saturation data. The sample generator 114 generate a representation of the token instances and the other value inputs 116 that is forwarded to both a machine learning trainer 120 and a model and data analyzer 210. The machine learning trainer 120 receives representation of the token instances and the other value inputs 116 and the affective response annotations 106, and generates an emotional state model 122 that is analyzed by the model and data analyzer 210, together with the representation of the token instances and the other value inputs 116, to generate the library of affective response to tokens 212.

Figure 31:
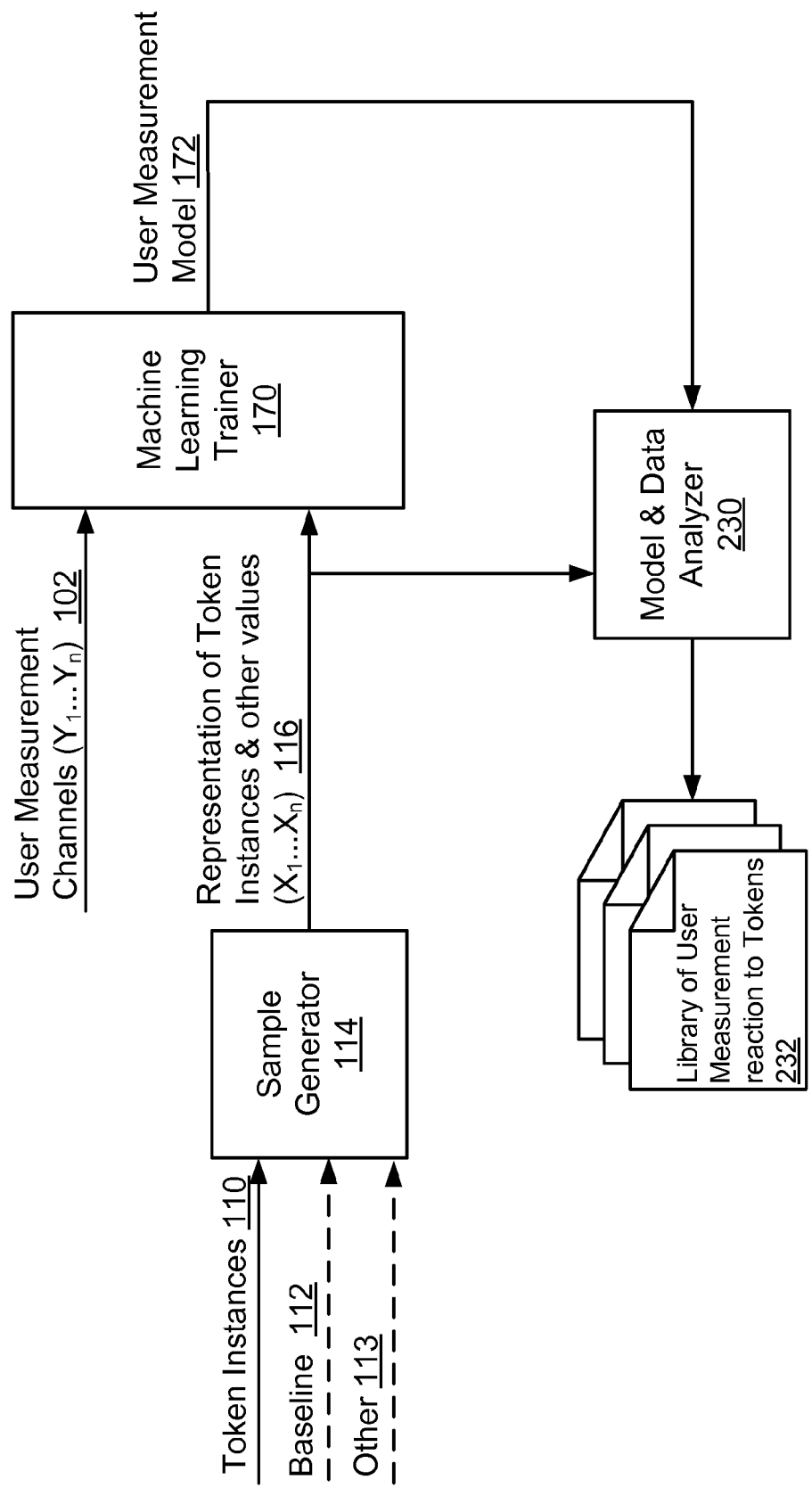
FIG. 31 illustrates a measurement library with input base dynamic analysis.

FIG. 31 illustrates a machine learning based system with input base dynamic analysis for generating a library of user measurement reaction to tokens 232. Sample generator 114 receives token instances 110, and optionally other inputs 113 that may include the user's baseline 112. The sample generator 114 generate a representation of the token instances and the other value inputs 116 that is forwarded to both a machine learning trainer 170 and a model and data analyzer 230. The machine learning trainer 170 receives representation of the token instances and the other value inputs 116 and the user measurement channels 102, and generates a user measurement model 172 that is analyzed by the model and data analyzer 230, together with the representation of the token instances and the other value inputs 116, to generate the library of user measurement reaction to tokens 232.

Figure 32:
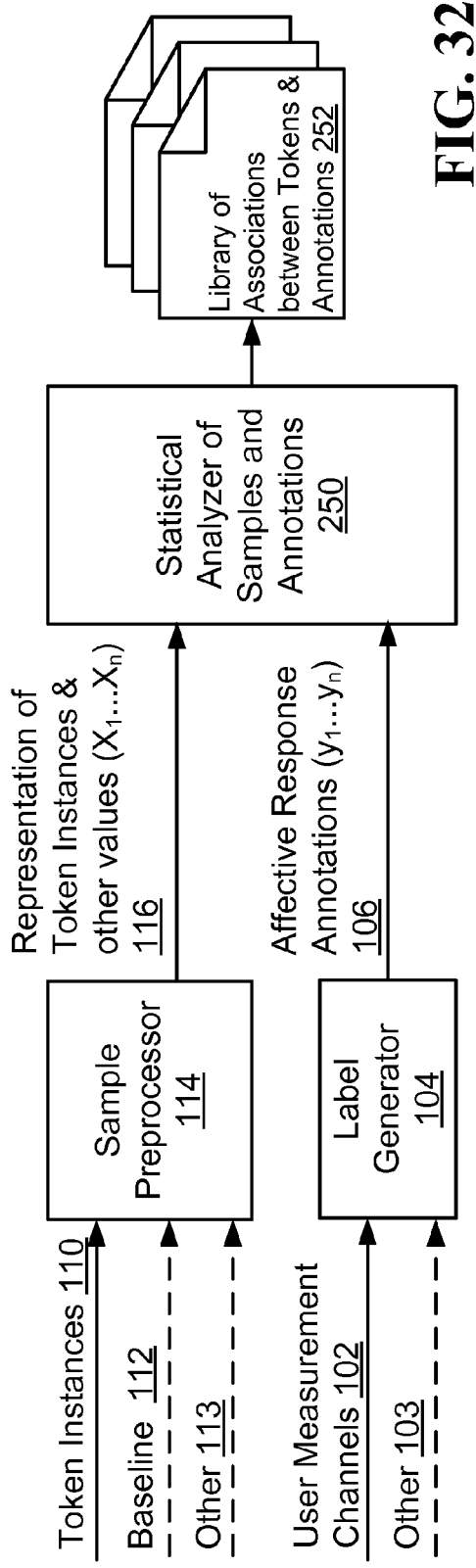
FIG. 32 illustrates a statistics based system for generating a library of association between tokens and annotations.

FIG. 32 illustrates a statistics based system for generating a library of association between tokens and annotations 252. A statistical analyzer of samples and annotations 250 receives the representation of the token instances and the other value inputs 116 and the affective response annotations 106, and generates the library of association between tokens and annotations 252.

Figure 33:
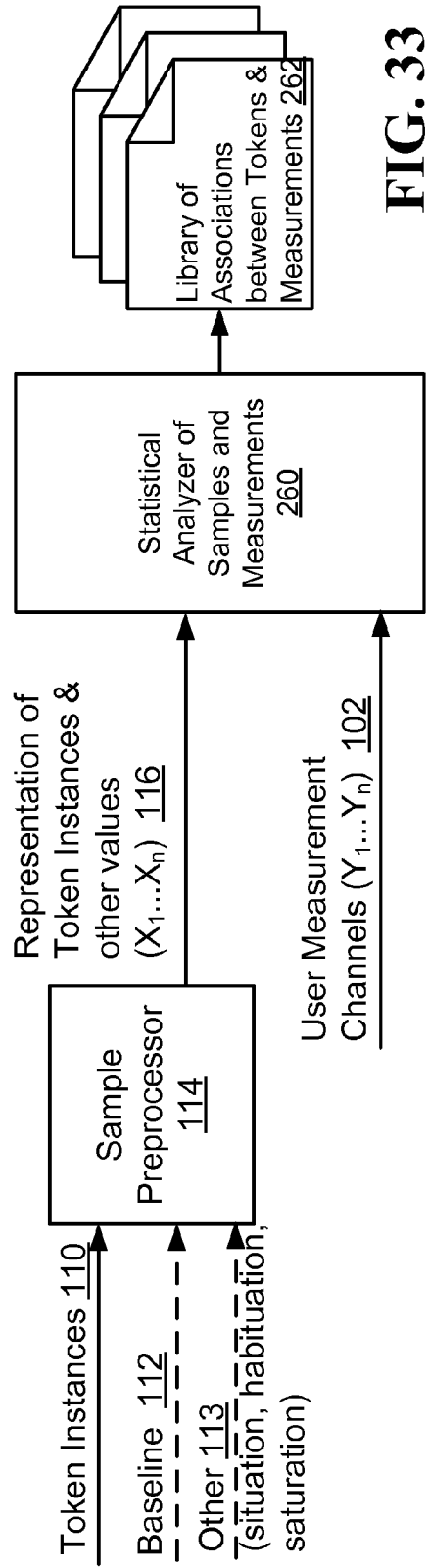
FIG. 33 illustrates a statistics based system for generating a library of association between tokens and user measurements.

FIG. 33 illustrates a statistics based system for generating a library of association between tokens and user measurements 262. A statistical analyzer of samples and measurement 260 receives the representation of the token instances and the other value inputs 116 and the user measurement channels 102, and generates the library of association between tokens and user measurements 262.

In one embodiment, a method for generating a situation-dependent library comprising a user's expected response to tokens representing stimuli that influence the user's affective state, includes the following steps:

In step 1, receiving samples comprising temporal windows of token instances to which the user was exposed, wherein the token instances have overlapping instantiation periods and are spread over a long period of time that spans different situations; at least one token is expected to elicit from the user a noticeably different affective response in the different situations.

In step 2, receiving target values corresponding to the temporal windows of token instances; the target values represent the user's responses to the token instances from the temporal windows of token instances.

In step 3, training a machine learning-based user response model using the samples and the corresponding target values.

And in step 4, analyzing the machine learning-based user response model to generate the situation-dependent library comprising the user's expected response to tokens, which accounts for the variations in the user's affective response in the different situations.

Affective Response Predictor for Human Interactions

In one embodiment, an affective response predictor for human interactions is used to predict how a user will react to a shared experience with another individual (also referred to as the "partner" for the interaction). The user's personal affective response predictor is trained on data collected from previous interactions the user had, including representations of the profiles of the individuals the user shared experiences with. Optionally, the data used for training the affective response predictor, also includes a representation of the user's profile, the situation the user was in, and/or a representation of details regarding the activity or interaction between the user and another individual. In addition, the data used for training the affective response predictor also includes prediction target values, derived from measurements of the user's affective response to the corresponding interactions.

In one embodiment, representation of a profile of a partner, and optionally the profile of the user, may include token instances describing various details, such as the person's age, gender, race, education, hobbies, income, appearance, languages spoken, and/or the person's situation (such as, the time of day, location, time available for interaction). Optionally, a person's profile is generated from data obtained from the content of the person's account on a web site, such as a social network profile (e.g., information obtained from a person's Facebook or LinkedIn accounts). Optionally, a person's profile further includes token instances corresponding to content consumed by the person and/or activities the person partook in, for example games played, URLs of web-sites visited, and/or movies viewed. Optionally, the representation of a person's profile further includes token instances representing the results of semantic analysis of content produced by the person and/or some of the person's previous social interactions, such as recorded voice or video conversation, blog posts, post on twitter, comments and/or reviews on websites (e.g., Amazon, eBay, IMDb ratings and/or reviews), and/or status updates or comments on social networks. Optionally, the details regarding the activity or interaction between the user and a partner include token instances related to information such as the expected duration of the interaction, the location of the interaction, the nature of the interaction (e.g., chat, playing a game together, going to a movie, etc.), and/or the plot or content involved in the interaction (e.g., the type of game that is to be played, the content of the video that is to be viewed, the type of food that is going to be eaten in a restaurant).

Identifying Relevant People for Shared Experience

In one embodiment, a method for predicting a user's affective response to a partner for a shared experience with the user includes the following steps:

In step 1, receiving a sample including token instances describing the partner. Optionally, the partner's description includes the partner's profile. Optionally, the sample further includes token instances describing the user, and/or token instances describing details of the shared experience. Optionally, the sample may further include token instances describing the user's situation. Optionally, the sample further includes at least one token instance representing an emotional state of the user. Optionally, the sample may also include at least one token instance representing a baseline value of the user at a time close to the start of the expected experience (e.g., a value derived from a user measurement channel and/or an estimation of the user's baseline emotional state such as the user's mood). For example, in a case where the shared experience is expected to occur in a short while, referred to as an "imminent shared experience", a sample may include a token instance describing the user's emotional state at that time (e.g., happy or sad), or a value derived from a user measurement channel (e.g., a measurement of the user's heart rate). In addition, the sample may also include a baseline value, such as the user's average heart rate in a window of two hours prior to the experience.

In step 2, evaluating the partner by providing the sample to a personal affective response predictor of the user, trained on training samples including token instances and measured affective responses of the user. The affective response measurements are taken from the user at times close to the shared experiences, reflecting the user's affective response to the experience. Some of the token instances in the samples describe the user's partners to the shared experience, and optionally, include additional token instances that describe the user (e.g., the user's situation at the time of the experience), and/or details related to the shared experience (e.g., content, location). Optionally, some of the samples may further include values representing emotional states of the user at times corresponding to the shared experiences, for example values of user measurement channels taken before commencing with the share experience with the partner.

And in steps 3, returning the user's predicted affective response to the partner for the shared experience. Optionally, the predicted affective response is the user's estimated emotional state after the shared experience or the change in the user's emotional state after the shared experience. Optionally, the predicted affective response is an expected value for the user for a measurement channel of the user after going through the shared experience, or the predictive value may be the change in the expected value of the measurement of the user.

In one example, training data for a personal affective response predictor may include samples describing previous shared experiences the user had with partners during shared missions in an adventure game played in a virtual world. In this example, each training sample includes token instances describing the characters of the partners in the game, such as statistics regarding the character's ability (e.g., experience points, strength, dexterity) and/or token instances describing the partner himself or herself, for example the partner's gender, age, location. Optionally, the sample to the predictor may also include token instances related to the user and the user's situation (e.g., the user's location, the time of day, the user's mood). Optionally, the samples may also include token instances describing the partner's situation. Optionally, the sample may also include token instances related to the shared experience, such as the type of game, the type of mission (e.g., relaxed exploration or intense battle), and/or the expected duration. In addition, at least some of the training samples may include affective response target values, such as the heart rate, and skin conductance measured for the user, before, during, and/or after the shared experience corresponding to the sample. The affective response may be expressed as measurement values, and/or as an emotional state (for example, as estimated via an emotional state predictor that takes as inputs values from user measurement channels).

In another example, training samples for the user's personal affective response predictor may include samples describing previous shared experiences the user had chatting with other people in a virtual chat room in which people are represented by avatars. In this example, each training sample includes token instances describing the partners such as details taken from the partner's profile (e.g., Facebook account) including details like gender, age, occupation, hobbies, and/or the partner's favorite bands, books and/or movies. Optionally, a sample may include token instances derived from content created or consumed by the partner (e.g., token instances derived from analysis of the content, and/or demeanor of the partner during conversations, status updates, comments on websites). Optionally, a sample may further include token instances describing the user's and/or the partner's situation (e.g., location, time of day, mood as estimated from semantic analysis of conversation or affective state measurements). Optionally, a sample may include token instance corresponding to the user's affective state prior to the experience, such as values derived from heart rate monitoring of the user in order to estimate the user's level of excitement. In addition, at least some of the training samples may include affective response target values corresponding to the user's affective response to the chat, such as the estimated change in emotional state, which is obtained from a predictor that bases its predictions on data including video camera measurements, which can be used to detect behavioral cues and facial expressions, and/or audio measurements, which can be used to detect tension in the voice. These measurements may be combined and provided to a predictor in order obtained an estimate of the change in the user's emotional state.

In yet another example, training samples for the affective response predictor may include samples describing previous shared experiences the user had viewing movies with friends. In this example, each training sample includes token instances describing the partners (friends) such as details taken from the partner's profile (e.g., Facebook account) and ratings they provided to movies (e.g., ratings on IMDb or Amazon). Optionally, a sample may also include token instances describing ratings the user gave to movies. Optionally, a sample may include token instances describing the shared experience, such as the genre of the movie, the lead actors, and the location of the viewing (e.g., at home or at the theatre). In addition, at least some of the training samples may include affective response target values corresponding to the user's affective response to movie viewing for example, by using motion sensors and skin temperature measurements, to estimate if the user was engaged or bored during the viewing.

In one embodiment, the affective response predictor for human interactions is a machine learning model trained on data including token instances. Optionally, the data including token instances is organized as vectors of token instances, lists of token instances, and/or temporal windows of token instances.

In one example, a personal affective response predictor of the user includes a "K nearest-neighbors" predictor (for values K>1), which stores some of the training samples in a space (for example as real-valued points in a multidimensional space), along with each point's measured affective response. Given a new sample as a query, the K nearest neighbor predictor finds the K nearest stored samples to the query sample, for example by using a distance metric such as Euclidean distance, or the dot product between the vectors corresponding to the points. The predictor then returns an average of the K affective response values corresponding to the K nearest samples as the predicted affective response to the query samples.

In another example, a personal affective response predictor of the user includes a decision tree classifier (e.g., a C4.5 classifier or an alternating decision tree), which can predict a categorial emotional state for the user from an input vector of token instances (which may contain values that are numerical or categorical). Such a classifier builds a classification tree from the training data; the structure and values along the trees branches reflect rules learned from the data that may be applied to a new query sample in order for the classifier to determine the most likely affective response the user is expected to have after the shared experience with the partner.

In yet another example, a personal affective response predictor of the user includes a neural network predictor, which is trained on samples including vectors of numerical data (the token instances) and affective responses which are categorial, univariate, or multivariate values representing the user's affective response (or change in the affective response) after experiencing the shared experience corresponding to the sample. Given the training data, the neural network learns a topology (e.g., connectivity between perceptions) and sets weights on the connections in order to make accurate predictions on the training data. Given a new query sample, representing a shared experience of the user with partner, the neural network is capable of predicting the user's expected affective response in a manner that is in agreement with the relationships between variables that are observed in the training data.

In one embodiment, samples provided to the user's personal affective response predictor may include one or more token instances representing an objective for the shared experience, for example, these token instances may represent the user's and/or a partner's objective for the shared experience. Objectives may have various forms, for example, advancing career or personal goals, relaxing, being entertained, being frightened (e.g., honor movie viewers). Under similar circumstances, that fact that a user might have a specific objective, may lead to very different affective responses to the shared experience.

In one example, a user's objective for a shared experience involving a game may be to gain maximal experience or advance as many levels as possible. In such a case, the user's affective response to pairing up with a pleasant but inexperience player might be negative, while the affective response to pairing up with an experienced ill-tempered player might be positive since it advances the user's goals. Note that for many other objectives or goals the user might have, such as making new social contacts or being entertained, the user's affective response to the shared activities with the different partners might be quite different (e.g., a positive affective response to the pleasant player, and a chilly response to playing with the ill-tempered player). In another example, a user's objective for interaction in a for chatting with a partner in an online chat room might be to find a romantic partner, while at other times it might be to discuss sports, for example to lament about the poor performance of the user's favorite sports team. Given these different objectives, the user (who for example is a male seeking a female romantic partner), may have very different affective responses to different shared experiences. For example, the male user might have a negative affective response if approached by a person suggesting to play a virtual game of pool and chat, if the potential partner is a male or a female whose Facebook status says she is in a relationship. However, under different circumstances, for instance if the user just wanted to relax, a virtual game of pool might have been quite desirable, and would elicit a positive affective response. Similarly, while normally the user wouldn't be caught dead listening to Justin Bieber, if approached by a female, whose Facebook page says is single and boasts a cute profile picture, the user might have a positive affective response to such a shared experience since it advances his goals.

In one embodiment, a user's objective for some of the shared experiences is provided explicitly by the user, for example, by selecting an objective from a menu, of multiple objectives, from semantic analysis of the user's conversations (e.g., a status saying "I'm bored"), and/or from analysis of the user's state. For example, a system might note the user's status on a social network has turned to single, and automatically set the objective to "making new social contacts" (after a learned "grieving period" proportional to duration of the user's "in a relationship" status).

In one embodiment, a user's machine learning-based personal affective response predictor makes in some cases, significantly different affective response predictions for a user's shared experience depending on a value of a token instance describing the user's goal. In one example, where the machine learning-based predictor is a K nearest-neighbor predictor, the system might create separate K nearest-neighbor predictor for each objective, trained on different subsets of training data corresponding to the different objectives the user had at the time. Given a new sample with an objective for the user, the classifier selects a predictor trained on data with the appropriate objective, and returns the prediction from that specific model. In another example, where the machine learning-based predictor is a decision tree, the training algorithm can take advantage of training samples with different objectives that can lead to significantly different affective responses, by creating a decision tree with nodes that branch according to the value of the tokens representing the user (or the partners) objectives. Thus, when given different objectives for a query sample, the predictor will traverse different paths on the tree and possibly return different predictions for the user's affective response to the shared experience.

In one embodiment, the affective response predictor for human interactions is used to recommend to the user which interactions will be most to his/her liking, for example, which people to approach in a virtual chat room, which characters to join in an online role playing game, and/or which friend to initiate a chat with.

Emotion-Based Social Networking

In one embodiment, an affective response based predictor for human interactions is trained on data comprising a user profile expressed as token instances, and another user profile, where the target value is the change in the affective response measured as a result of the interaction between the users. After collecting a certain amount of samples, a predictor can be trained for predicting and/or ranking the expected affective response of the user when interacting with other people. This prediction can be used to suggest potential users for interaction.

In one embodiment, a method for predicting a user's affective response to a partner for a shared experience with the user includes the following steps: receiving a sample comprising token instances describing the partner; evaluating the partner by providing the sample to a personal affective response predictor trained on training samples comprising token instances and measured affective responses of the user corresponding to the training samples; and returning the user's predicted affective response to the partner for the shared experience. Optionally, the sample also includes a token instance describing the shared experience; and at least some of the training samples further comprise token instances describing shared experiences. Optionally, selecting the shared experience by predicting the user's affective response to the partner for different candidate shared experiences, and selecting the shared experience based on the predicted affective responses. Optionally, the imminent shared experience takes place in a virtual world, the candidate shared experiences represent different variants of a shared experience, and the predictions are used to optimize the shared experience. Optionally, the sample also includes a token instance describing the user's situation, and at least some of the training samples further comprise token instances describing situations in which the user was in. Optionally, the sample also includes a value representing emotional state of the user; and at least some of the training samples also include values representing emotional states of the user at times corresponding to the training samples. Optionally, the sample also includes a baseline value for the user's affective response, and at least some of the training samples also include baseline values for the user's affective responses at times corresponding to the training samples. Optionally, the sample also includes a token instance representing an objective of the user for the shared experience, and the objective is selected explicitly by the user, wherein different objectives result in different predicted affective response. Additionally, at least some of the training samples may also include token instances representing objectives of the user for shared experiences at times corresponding to the training samples. Optionally, the shared experience takes place in a virtual world, and the partner is a virtual entity that is available for the shared experience with the user essentially without constraints related to activities of the virtual entity in the virtual world. Optionally, the shared experience takes place in a virtual world, the partner is controlled by a real person, and the availability of the partner is constrained by the availability of the real person. Optionally, the shared experience takes place in the physical world, and is constrained by the relative location of the user, the partner, and the venue of the shared experience.

In one embodiment, a method for ranking partners for an imminent shared experience with a user, includes the following steps: receiving token instances describing the partners; receiving an unsolicited measurement of the user's affective state in a temporal proximity to the imminent shared experience; and ranking the partners according to their suitability to the shared experience with the user based on the output of a ranker fed with input samples comprising the token instances describing the partners and the unsolicited measurement of the user's affective state. Optionally, further comprising selecting at least one partner for the shared experience with the user based on the ranking of the partners according to their suitability to the shared experience. Optionally, the ranker was trained on training samples comprising token instances describing partners and unsolicited measurements of the user's affective state. Optionally, the samples provided to the ranker also comprise a token instance describing the imminent shared experience, and at least some of the training samples also comprise token instances describing shared experiences. Optionally, the samples provided to the ranker also comprise a token instance describing the user's situation; and at least some of the training samples further comprise token instances describing situations in which the user was in. Optionally, the samples provided to the ranker also includes a baseline value for the user's affective response; and at least some of the training samples further comprise baseline values for the user's affective responses at times corresponding to the training samples. Optionally, the samples also include a token instance representing an objective of the user for the imminent shared experience, and the objective is selected explicitly by the user, wherein different objectives result in different rankings of the partners.

In one embodiment, the shared experience takes place in a virtual world, and the partners are virtual entities that are available for the shared experience with the user essentially without constraints related to activities of the virtual entities in the virtual world. Optionally, at least some of the partners are controlled by real people, and the availability of the controlled partners is constrained by the availability of the real people.

In another embodiment, the shared experience takes place in the physical world, and is constrained by the relative location of the user, the partners, and the venue of the shared experience. Optionally, at least some of the partners are virtual entities, and there are variations between the token instances corresponding to each virtual entities. Optionally, the variations represent different characteristics of the virtual entities and the ranking of the partners is used to optimize the characteristics of a virtual entity partner for the imminent shared experience with the user.

In one embodiment, a method for predicting the quality of an imminent shared experience between a group of users, includes the following steps: receiving token instances describing the members of the group; receiving an unsolicited measurement of at least one of the group members' affective state in a temporal proximity to the imminent shared experience; predicting the quality of the imminent shared experience using a predictor provided with input data comprising the token instances and the unsolicited measurement; wherein the predictor was trained on training samples comprising token instances describing members of groups and unsolicited measured affective responses of users corresponding to at least some of the training samples. Optionally, the method also includes a step of choosing the group of users for the imminent shared experience from among a plurality of candidate groups containing different sets of users, by predicting the quality of the imminent shared experience for the different candidate groups, and selecting the group of users based on the predicted quality results. Optionally, the token instances further comprise a token instance describing the imminent shared experience; and at least some of the training samples further comprise token instances describing shared experiences. Optionally, the method also includes a step of selecting an imminent shared experience for the group by predicting the quality of different candidate imminent shared experiences for the group of users, and selecting the imminent shared experience based on the predicted quality results. Optionally, the imminent shared experience takes place in a virtual world, the candidate imminent shared experiences represent different variants of a shared experience, and the predictions are used to optimize the imminent shared experience.

People are faced with a plethora of choices when it comes to various activities they can participate in with others. The options seem endless when the activities take place in the digital or virtual world. There is a vast amount of digital content such as videos, music, movies, and websites that can be visited, downloaded, or streamed. There is also large number of online games with different missions to accomplish and many virtual worlds with never ending regions to explore and activities in which to participate. Though having a large number of choices is often desirable, and makes it possible to have something suitable for everyone, there is often a flip side to having an excess of alternatives. When faced with a surplus of choices, people are often stricken with paralysis, and are rendered incapable of making a decision. So quite often, they end up not making a choice at all. This is a well-known and studied phenomenon in marketing, where in order to engage people, they are presented with only a small number of options, despite the availability of many more. The big problem is how to decide which limited group of options is best to present.

The problem of excess of choices is further compounded when the user wants to partake in an activity with others, making it a shared experience. Not only is the user faced with the choice of content of the experience (e.g., the media, activity or venue), there are also many other choices that arise as a result of the activity being a shared-experience. First, there is the question of which friends to invite or join in the activity. Naturally, a person might have different inclination towards certain people depending on the type of shared activity that is planned. Often, a shared activity may involve communication between the participants. There might be many modes of communication available such as instant messages, audio, video, virtual avatars, and even holograms. The choice of communication method may depend on various factors such as the content, participating parties, and environment (e.g., in a public place or home alone). The user might also be faced with other choices such as the pricing model to choose for paying for the activity.

Since every user planning to partake in the shared experience may have his or her own preferences and constraints, deciding on the right set of options can be a tedious experience, in which the users are faced with many options and choices. Arriving at an agreed upon decision in such cases might be a tedious task, which presents each user with many decisions that need to be made.

In one embodiment, a system for reducing the amount of choices and decisions a person needs to make in order to partake in a shared experience with other users comprises one or more of these elements: (1) A user response predictor that accepts inputs describing the activity (such as the content, participants, communication methods, pricing, etc.) and predicts the user's expected response; (2) A generator of potential activities; (3) A mechanism for querying and integrating the response of multiple user's regarding potential activities comprising propagation of information about the potential activities to the other users' predictors, receiving their responses and/or constraints regarding the proposed activities, and reducing the list of potential activities to a small number of most viable options.

In one embodiment, a shared activity comprises a joint experience between users interacting in the physical world (e.g., going to a party, going on a trip, going shopping, performing volunteer work, studying).

In one embodiment, a shared activity comprises a joint experience and/or consumption of digital media such as watching a movie, listening to music, browsing websites. Optionally, the users are in physical proximity when media is consumed (e.g., the same room). Optionally, the users are in virtual proximity when media is consumed (e.g., in the same virtual room). Optionally, the shared activity comprises a joint experience between users in a virtual world, such as playing a game together in a virtual world (e.g., World of Warcraft), or join exploring in a virtual world (e.g., Second life). Optionally, the users consume the media separately, at different times and/or locations.

In one embodiment, users partaking in the shared activity may communicate with each other. Optionally, the communication occurs while the activity is going on. Optionally, the communication takes before and/or after the activity. In one embodiment, one or more methods of communication may be chosen to be used between two or more users partaking in the shared activity. For example, voice conversation, video conversation, conversation with the aid of avatars, instant messages, emails, blogging, micro-blogging, status updates on a social network.

In one embodiment, the shared activity may incur a cost, for example, a monetary payment may be required (e.g., real or virtual currency), or payment in the form of credits. Optionally, different options may be available for the user's to choose, for example, which users are to pay for the activity, and under what terms (e.g., method of payment, amount).

In one embodiment, a predictor is used to predict the user's response to a shared activity. Optionally, the user's response is expressed as an affective response. Optionally, user's response is expressed in terms of user measurement channels. Optionally, the input to the predictor comprises a representation of token instances. Optionally, the input to the predictor comprises representation of temporal windows of token instances.

In one embodiment, the tokens describing an activity comprise one or more of the following types of tokens: (1) tokens describing details of the activity. For example, what type of activity is going to be (e.g., biking, running, watching a movie, playing a game), and/or specifics about the location and/or duration; (2) tokens describing the content of the activity. For example, tokens describing the content of a movie, or tokens describing the content of game play; (3) tokens describing the participants (e.g., names, occupation, age, personality, etc.); (4) tokens describing a method of communication between participants in the activity.

The following two examples disclose situations where a user has an activity, and the embodiments find interested friends.

In one embodiment, a social network able to identify friends who are likely to want to join an activity, comprising: a plurality of social network users; each social network user is associated with a personalized queryable predictor configured to receive tokens representing a potential activity, and return an estimated response to the potential activity; a processor configured to receive an interest of a social network user in partaking in an activity described by a combination of non-temporally related tokens, wherein the user has not previously been exposed to the combination of the non-temporally related tokens. The processor is also configured to query the predictors associated with at least one of the user's friends to identify which of the user's friends are likely to want to join the activity. Additionally, the processor is also configured to select a subset of friends to join the activity and to take action with the selected subset of friends. Optionally, the action taken with the subset of selected friends comprises present the subset of selected friends to the user. Optionally, the action taken with the subset of selected friends comprises invite the subset of selected friends to join the activity. Optionally, the activity is an online game. Optionally, the number of the user's friends in the selected subset falls within a specified range. Optionally, the specified range is provided by a predictor associated with the user.

Optionally, the specified range is provided by the user. Optionally, the received tokens are generic tokens applicable to different activities. Optionally, the personalized queryable predictor of a social network user is further configured to make predictions that are dependent on tokens describing the location and time of the activity and the social network user. Optionally, the estimated response represents the user's disposition towards the content. Optionally, the user's disposition towards the content comprises interested and uninterested responses. Optionally, the estimated response is an estimated affective response. Optionally, the estimated response is represented by user measurement channels. Optionally, the processor is further configured to sort the selected subset of friends according to values of a reward function. Optionally, the processor is further configured to access a goal for the user, and choose a reward function to evaluate how the friends that are likely to want to join the activity are aligned with the goal. Optionally, the processor is also configured to access a goal for the user, and choose a reward function to evaluate the replies of the queried predictors according to the goal.

In one embodiment, social network able to identify friends who are likely to be interested in content, comprising: a plurality of social network users; each social network user is associated with a personalized queryable predictor configured to receive a plurality of tokens representing content, and return an estimated response to the content; a processor configured to receive an interest of a social network user in content described by a combination of tokens; wherein a subset of the token instances originate from same source and have overlapping instantiation periods; the processor is further configured to query the predictors associated with the user's friends to identify which of the user's friends are likely to be interested in the content; and the processor is further configured to take action with the user's friends that are likely be interested in the content. Optionally, the predictors associated with the user's friends utilize estimates of the user's friends' current emotional states to predict the user's friends' interest in the content.

Optionally, the action taken with the user's friends comprises join the content for shared consumption. Optionally, action taken with the user's friends comprises consume the content independently. Optionally, the social network configured to share feedback between the user's friends. Optionally, the content is a coupon, and the action taken with the user's friends comprises suggesting the coupon to the friends. Optionally, the social network also configured to propagate automatically the content to the friends that are likely to want to be exposed to the content. Optionally, the user indicates automatic propagation and the social network configured to select automatically the interested friends.

In the disclosed embodiment, phrases like "propagating content" cover both propagating the content itself and propagating a pointer to the content. Optionally, the interested of the social network user in the content is inferred from the fact that the user began to consume the content. Optionally, the user has not previously been exposed to the combination of tokens.

Embodiments

In one embodiment, a system configured to estimate a response of a user to a token instance of interest, comprising: a processor configured to receive a background token instance to which the user was exposed, and to predict a response due to exposure to the background token instance; and a decomposer configured to receive a measured response of the user due to simultaneous exposure to both the background token instance and the token instance of interest, and to estimate response of the user to the token instance of interest based on the difference between the predicted response and the measured response. Optionally, the processor is further configured to receive a baseline value for response of the user, and to utilize the baseline value to calculate the predicted response. Optionally, the predicted response due to exposure to the background token instances is a response of the user due to exposure to the background token instances.

In one embodiment, a method for estimating a response of a user to a token instance of interest, comprising: receiving token instances comprising a background token instance to which the user is exposed; predicting response due to exposure to the background token instance; receiving a measured response of the user due to exposure to token instances comprising both the background token instance and the token instance of interest; and estimating response of the user to the token instance of interest based on difference between the predicted response and the measured response. Optionally, the token instance of interest is a token instance for which measured attention level of the user is highest. Optionally, the token instance of interest is a token instance for which predicted attention level is the highest. Optionally, there are multiple background token instances, at least some of the background token instances have overlapping instantiation periods, and the predicting the response to the background token instances utilizes a machine learning-based predictor for the response of the user. Optionally, the machine learning-based predictor is trained on data collected over a long period, in which the user was in different situations. Optionally, the machine learning-based predictor is trained on samples comprising data of previous instantiations of token instances in order to create a habituation compensating machine learning-based predictor for response of the user due to exposure of the user to the background token instances. Optionally, the method also includes a step involving receiving a baseline value for response of the user, and utilizing the baseline value for the predicting the response due to exposure to the background token instance. Optionally, the predicted response due to exposure to the background token instance is calculated by selecting a machine learning-based predictor for response of the user appropriate to a situation the user is in from among at least two machine learning-based predictors for responses of the user; wherein each machine learning-based predictor was trained on data collected over periods of time in which the user was in a situation belonging to a distinct set of situations specific to that machine learning-based predictor. Optionally, the estimated response of the user to the token instance of interest is given in terms of an emotional response of the user. Optionally, the estimated response of the user to the token instance of interest is given in terms of a value of a measurement channel of the user. Optionally, the predicted response due to exposure to the background token instances is a response of the user due to exposure to the background token instances. Optionally, the background token instances do not include the token instance of interest.

In one embodiment, a system configured to estimate a response of a user to a token instance of interest, comprising: a processor configured to receive a measured response of the user due to exposure to token instances comprising a background token instance and the token instance of interest, and to receive a predicted response due to exposure to the background token instance; and the processor is further configured to estimate the response of the user to the token instance of interest based on the difference between the predicted response and the measured response. Optionally, the predicted response is calculated using a machine learning-based predictor for the response of the user. Optionally, the background token instance and the token instance of interest have overlapping instantiation periods. Optionally, the predicted response due to exposure to the background token instance is a response of the user due to exposure to the background token instance.

In one embodiment, a method for estimating a response of a user to a token instance of interest, comprising: receiving a measured response of the user due to exposure to token instances comprising a background token instance and the token instance of interest; receiving a predicted response due to exposure to the background token instance; and estimating the response of the user to the token instance of interest based on different between the predicted response and the measured response. Optionally, the predicted response is calculated using a machine learning-based predictor for the response of the user. Optionally, the background token instance and the token instance of interest have overlapping instantiation periods. Optionally, the predicted response due to exposure to the background token instance is a response of the user due to exposure to the background token instance.

In one embodiment, a system configured to estimate a response of a user to a token instance of interest, comprising: a token instance remover configured to receive a temporal window of token instances and attention level of the user in at least one of the token instances belonging to the window; the token instance remover is further configured to utilize the attention level to select a token instance of interest from among the token instances belonging to the window, and remove the token instance of interest from the temporal window of token instances; a predictor of user response configured to receive the temporal window of token instances from which the token instance of interest was removed and predict a response to being exposed to the temporal window of token instances without the token instance of interest; and a decomposer configured to receive a measured response of the user due to exposure to the temporal window of token instances, and to estimate response of the user to the token instance of interest based on the difference between the predicted response and the measured response. Optionally, the token instance of interest is a token instance for which measured attention level of the user is highest. Optionally, the token instance of interest is a token instance for which predicted attention level is the highest. Optionally, the predicting the response to the temporal window of token instances without the token of interest utilizes a machine learning-based predictor for the response of the user. Optionally, the machine learning-based predictor is trained on data collected over a long period, in which the user was in different situations. Optionally, the machine learning-based predictor is trained on samples comprising data of previous instantiations of token instances in order to create a habituation compensating machine learning-based predictor for response of the user due to exposure of the user to the background token instances. Optionally, the estimated response of the user to the token instance of interest is given in terms of an emotional response of the user. Optionally, the estimated response of the user to the token instance of interest is given in terms of a value of a measurement channel of the user. Optionally, the predicted response due to exposure to the temporal window of token instances without the token of interest is a response of the user due to exposure to the temporal window of token instances without the token of interest. Optionally, the attention levels are derived from a measurement channel of the user. Optionally, the attention levels are predicted based on the token instances.

In one embodiment, a method for estimating a response of a user to a token instance of interest, comprising: receiving a temporal window of token instances comprising a plurality of token instances to which the user is exposed, wherein at least two of the token instances have overlapping instantiation periods; receiving a measured response of the user due to the exposure of the user to the temporal window of token instances; receiving attention level of the user in at least one of the token instances; using the attention level for selecting the token instance of interest from among the token instances, wherein less than a third of the token instances are considered to be of interest to the user; removing the token instance of interest from the temporal window of token instances; predicting response of the user to being exposed to the temporal window of token instances from which the token instance of interest was removed; and estimating response of the user to the token instance of interest from the difference between the predicted response and the measured response. Optionally, the response of the user to the token instance of interest is expressed as an affective response. Optionally, the response of the user to the token instance of interest is expressed with values of user measurement channels of the user. Optionally, the attention levels of the user in at least some of the token instances are derived from a measurement channel of the user. Optionally, the attention levels of the user in at least some of the token instances are predicted based on token instances. Optionally, the predicting the response due to exposure to the temporal window of token instances comprises predicting the response of the user due to exposure of the user to the token instances.

In one embodiment, a method for estimating a response of a user to a specific token instance in a variant of a repetitive scene, comprising: receiving measurements of responses taken at multiple exposures to variants of the repetitive scene; receiving another measurement of response of the user taken while the user is exposed to another variant of the repetitive scene that further includes the specific token instance; and estimating the response of the user to the specific token instance based on difference between the another measurement and a representation of the measurements. Optionally, variants of scenes are represented by token instances, and two variants are considered variants of a repetitive scene if at least 50% of their token instances are essentially the same. Optionally, two variants are considered variants of a repetitive scene if there is a probability of at least 20% that an ordinary user exposed to the two variants reports that the two are variants of a repetitive scene. Optionally, two variants are considered variants of a repetitive scene if there is a probability of at least 80% that an ordinary user exposed to the two variants reports that the two are variants of a repetitive scene. Optionally, two variants are considered variants of a repetitive scene if low-level features derived from the two variants are similar. Optionally, the other variant also includes a token instance having an overlapping instantiation period with the specific token instance. Optionally, the representation of the measurements is essentially an average of the measurements of the responses taken at multiple exposures to the variants of the repetitive scene. Optionally, the representation of the measurements is calculated based on the measurements of responses utilizing a predefined formula. Optionally, the method also includes a step involving storing the variants of the repetitive scene as temporal windows of token instances, and training a prediction model for response of the user to variants of the repetitive scene using training data comprising the stored temporal windows of token instances and their corresponding responses. Optionally, the representation of the measurements is obtained by providing the prediction model with temporal windows of token instances corresponding to the variants of the repetitive scene. Optionally, the specific token instance included in the variant of the repetitive scene does not significantly alter the essence of the repetitive scene compared to the other variants of the repetitive scene that do not include the specific token instance. Optionally, the other measurement is derived from multiple measurements of response of the user taken while the user was exposed to variants of the repetitive scene that include the specific token instance. Optionally, the repetitive scene is generated by a computer game, and the specific token instance included in the repetitive scene does not significantly alter the game's plot compared to the other variants of the repetitive scene that do not include the specific token instance. Optionally, the measurements of responses taken at multiple exposures to variants of the repetitive scene are measurements of responses of the user taken at multiple exposures of the user to variants of the repetitive scene. Optionally, most of the measurements of responses taken at multiple exposures to variants of the repetitive scene are measurements of responses of other users.

In one embodiment, a device for estimating a response of a user to a specific token instance in a repetitive scene includes the following: a memory configured to receive measurements of responses taken at multiple exposures to variants of the repetitive scene. The memory is also configured to receive, from a measuring device, another measurement of response of the user taken while the user is exposed to another variant of the repetitive scene that further includes the specific token instance. A processor is configured to estimate the response of the user to the specific token instance based on difference between the other measurement and a representation of the measurements. Optionally, variants of scenes are represented by token instances, and two variants are considered variants of a repetitive scene if at least 50% of their token instances are essentially the same. Optionally, two variants are considered variants of a repetitive scene if there is a probability of at least 20% that an ordinary user exposed to the two variants reports that the two are variants of a repetitive scene. Optionally, two variants are considered variants of a repetitive scene if there is a probability of at least 80% that an ordinary user exposed to the two variants reports that the two are variants of a repetitive scene. Optionally, two variants are considered variants of a repetitive scene if low-level features derived from the two variants are similar. Optionally, the other variant also includes a token instance having an overlapping instantiation period with the specific token instance. Optionally, the representation of the measurements is essentially an average of the measurements of the responses taken at multiple exposures to variants of the repetitive scene. Optionally, the representation of the measurements is calculated based on the measurements of responses utilizing a predefined formula. Optionally, the memory is also configured to store the variants of the repetitive scene as temporal windows of token instances, and a second processor is configured to train a prediction model for response of the user to variants of the repetitive scene using training data comprising the stored temporal windows of token instances and their corresponding responses. Optionally, the processor is configured to obtain the representation of the measurements by providing the prediction model with a temporal window of token instances corresponding to the other variant of the repetitive scene, which does not include the specific token instance. Optionally, having the specific token instance included in the repetitive scene does not significantly alter the essence of the repetitive scene compared to variants of the repetitive scene that do not include the specific token instance. Optionally, the measuring device is configured to derive the other measurement from multiple measurements of response of the user taken while the user was exposed to variants of the repetitive scene that include the specific token instance. Optionally, further comprising a computer game configured to generate the repetitive scene, and the specific token instance does not significantly alter the plot of the game compared to other variants of the repetitive scene that do not include the specific token instance. Optionally, the measurements of responses taken at multiple exposures to variants of the repetitive scene are measurements of responses of the user taken by the measuring device. Optionally, most of the measurements of responses taken at multiple exposures to variants of the repetitive scene are measurements of responses of other users.

In one embodiment, a method for estimating a response of a user to a first token instance in a repetitive scene, includes the following steps: receiving measurements of responses taken at multiple exposures to variants of a repetitive scene comprising the first token instance and a second token instance; receiving another measurement of response of the user taken while the user is exposed to another variant of the repetitive scene that lacks the first token instance that appeared in the repetitive scenes corresponding to the measurements; and estimating the response of the user to the first token instance based on difference between representation of the measurements and the another measurement. Optionally, variants of scenes are represented by token instances, and two variants are considered variants of a repetitive scene if at least 50% of their token instances are essentially the same. Optionally, two variants are considered variants of a repetitive scene if there is a probability of at least 20% that an ordinary user exposed to the two variants reports that the two are variants of a repetitive scene. Optionally, two variants are considered variants of a repetitive scene if there is a probability of at least 80% that an ordinary user exposed to the two variants reports that the two are variants of a repetitive scene. Optionally, two variants are considered variants of a repetitive scene if low-level features derived from the two variants are similar. Optionally, the first token instance and the second token instance have overlapping instantiations periods. Optionally, the removal of the first token instance does not significantly alter the essence of the repetitive scene compared to variants of the repetitive scene that include the first token instance. Optionally, the measurements of responses taken at multiple exposures to variants of the repetitive scene are measurements of responses of the user taken at multiple exposures of the user to variants of the repetitive scene. Optionally, most of the measurements of responses taken at multiple exposures to variants of the repetitive scene are measurements of responses of other users. Optionally, the representation of the measurements is essentially an average of the measurements of the responses taken at multiple exposures to variants of the repetitive scene. Optionally, the representation of the measurements is calculated based on the measurements of responses utilizing a predefined formula.

In one embodiment, a system configured to estimate a response of a user to a first token instance in a repetitive scene, includes the following: a memory configured to receive measurements of responses taken at multiple exposures to variants of a repetitive scene comprising the first token instance and a second token instance. The memory is also configured to receive, from a measuring device, another measurement of response of the user taken while the user is exposed to another variant of the repetitive scene that lacks the first token instance that appeared in the repetitive scenes corresponding to the measurements. The system also includes a processor configured to estimate the response of the user to the first token instance based on difference between representation of the measurements and the other measurement. Optionally, variants of scenes are represented by token instances, and two variants are considered variants of a repetitive scene if at least 50% of their token instances are essentially the same. Optionally, two variants are considered variants of a repetitive scene if there is a probability of at least 20% that an ordinary user exposed to the two variants reports that the two are variants of a repetitive scene. Optionally, two variants are considered variants of a repetitive scene if there is a probability of at least 80% that an ordinary user exposed to the two variants reports that the two are variants of a repetitive scene. Optionally, two variants are considered variants of a repetitive scene if low-level features derived from the two variants are similar. Optionally, the removal of the first token instance does not significantly alter the essence of the repetitive scene compared to variants of the repetitive scene that include the first token instance. Optionally, the measurements of responses taken at multiple exposures to variants of the repetitive scene are measurements of responses of the user taken at multiple exposures of the user to variants of the repetitive scene. Optionally, most of the measurements of responses taken at multiple exposures to variants of the repetitive scene are measurements of responses of other users. Optionally, the representation of the measurements is essentially an average of the measurements of the responses taken at multiple exposures to variants of the repetitive scene. Optionally, the representation of the measurements is calculated based on the measurements of responses utilizing a predefined formula.

While the above embodiments described in the general context of program components that execute in conjunction with an application program that runs on an operating system on a computer, which may be a personal computer, those skilled in the art will recognize that aspects may also be implemented in combination with other program components. Program components may include routines, programs, modules, data structures, and other types of structures that perform particular tasks or implement particular abstract data types. Moreover, the embodiments may be practiced with other computer system configurations, including hand-held devices, multiprocessor systems, microprocessor-based or programmable consumer electronics, minicomputers, mainframe computers, and comparable computing devices. The embodiments may also be practiced in a distributed computing environment where tasks are performed by remote processing devices that are linked through a communications network. In a distributed computing environment, program components may be located in both local and remote memory storage devices.

Embodiments may be implemented as a computer-implemented process, a computing system, or as an article of manufacture, such as a computer program product or computer readable media. The computer program product may be a computer storage medium readable by a computer system and encoding a computer program that comprises instructions for causing a computer or computing system to perform example processes. The computer-readable storage medium can for example be implemented via one or more of a volatile computer memory, a non-volatile memory, a hard drive, a flash drive, a disk, a compact disk, and/or comparable media.

Throughout this specification, references are made to services. A service as used herein describes any networked/online applications that may receive a user's personal information as part of its regular operations and process/store/forward that information. Such applications may be executed on a single computing device, on multiple computing devices in a distributed manner, and so on. Embodiments may also be implemented in a hosted service executed over a plurality of servers or comparable systems. The term "server" generally refers to a computing device executing one or more software programs typically in a networked environment. However, a server may also be implemented as a virtual server (software programs) executed on one or more computing devices viewed as a server on the network. Moreover, embodiments are not limited to personal data. Systems for handling preferences and policies may be implemented in systems for right management and/or usage control using the principles described above.

Herein, a predetermined value, such as a predetermined confidence level or a predetermined threshold, is a fixed value and/or a value determined any time before performing a calculation that compares its result with the predetermined value. A value is also considered to be a predetermined value when the logic used to determine a threshold is known before start calculating the threshold.

In this description, references to "one embodiment" mean that the feature being referred to may be included in at least one embodiment of the invention. Moreover, separate references to "one embodiment" or "some embodiments" in this description do not necessarily refer to the same embodiment.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the details of the order or sequence of steps of operation of methods, or to details of implementation of devices, set in the description, drawings, or examples. Moreover, individual blocks illustrated in the figures may be functional in nature and do not necessarily correspond to discrete hardware elements.

While the methods disclosed herein have been described and shown with reference to particular steps performed in a particular order, it is understood that these steps may be combined, sub-divided, or reordered to form an equivalent method without departing from the teachings of the embodiments. Accordingly, unless specifically indicated herein, the order and grouping of the steps is not a limitation of the embodiments. Furthermore, methods and mechanisms of the embodiments will sometimes be described in singular form for clarity. However, some embodiments may include multiple iterations of a method or multiple instantiations of a mechanism unless noted otherwise. For example, when an interface is disclosed in one embodiment, the scope of the embodiment is intended to also cover the use of multiple interfaces. Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, it is intended to embrace all such alternatives, modifications, and variations that fall within the spirit and scope of the appended claims and their equivalents.

What is claimed is:

1. A system configured to estimate affective response to a token instance of interest, comprising:
   a memory configured to store: token instances to which a user was exposed, a total affective response of the user to the token instances, and representations of first and second attention levels of the user in respective first and second token instances from among the token instances; wherein the total affective response is based, at least in part, on values of a user measurement channel that are not utilized to generate the representations of the first and second attention levels; wherein the first and second token instances have overlapping instantiation periods; and wherein the first attention level is greater than the second attention level;
   a processor configured to select, based on the representations of the first and second attention levels, the first token instance as the token instance of interest; and
   the processor is further configured to estimate the affective response to the token instance of interest from the total affective response.

2. The system of claim 1, wherein the total affective response is expressed as an emotional response.

3. The system of claim 1, wherein the total affective response is based on values of a user measurement channel of the user.

4. The system of claim 1, wherein the total affective response is proportional to the difference between affective responses of the user before and after the user was exposed to the token instances.

5. The system of claim 1, wherein the memory is further configured to store a baseline value for affective response of the user, and the processor is further configured to calculate the total affective response with respect to the baseline value; whereby the baseline value represents a usual affective response of the user, as computed from multiple values acquired over a period of at least a few hours.

6. The system of claim 1, wherein more than 50% of the total affective response is attributed to the affective response to the token instance of interest.

7. The system of claim 1, wherein the token instances originate from multiple distinct token sources.

8. A method for estimating affective response to a token instance of interest, comprising:
   receiving token instances to which a user was exposed;
   receiving a total affective response of the user to the token instances;
   receiving representations of first and second attention levels of the user in respective first and second token instances from among the token instances; wherein the first and second token instances have overlapping instantiation periods; wherein the total affective response is based, at least in part, on values of a user measurement channel that are not utilized to generate the representations of the first and second attention levels; and wherein the first attention level is greater than the second attention level;
   selecting the first token instance as the token instance based on the representations of the first and second attention levels; and
   estimating the affective response to the token instance of interest from the total affective response.

9. The method of claim 8, wherein the total affective response to the token instances is expressed as an emotional response.

10. The method of claim 8, wherein the total affective response is based on user measurement channels of the user.

11. The method of claim 8, wherein the total affective response to the token instances is proportional to the difference between affective responses of the user before and after the user was exposed to the token instances.

12. The method of claim 8, further comprising receiving a baseline value for the affective response of the user, and calculating the total affective response with respect to the baseline value; whereby the baseline value represents a usual affective response of the user, as computed from multiple values acquired over a period of at least a few hours.

13. The method of claim 8, wherein more than 50% of the total affective response is attributed to the affective response to the token instance of interest.

14. The method of claim 8, wherein the token instances originate from multiple distinct token sources.

15. A non-transitory computer-readable medium for use in a computer to estimate affective response to a token instance of interest; the computer comprises a processor, and the non-transitory computer-readable medium comprising:
   program code for receiving token instances to which a user was exposed;
   program code for receiving a total affective response of the user to the token instances;
   program code for receiving representations of first and second attention levels of the user in respective first and second token instances from among the token instances; wherein the first and second token instances have overlapping instantiation periods; wherein the total affective response is based, at least in part, on values of a user measurement channel that are not utilized to generate the representations of the first and second attention levels; and wherein the first attention level is greater than the second attention level;
   program code for selecting the first token instance as the token instance of interest based on the representations of the first and second attention levels; and
   program code for estimating the affective response to the token instance of interest from the total affective response.

16. The non-transitory computer-readable medium of claim 15, further comprising program code for receiving a baseline value for the affective response of the user, and calculating the total affective response with respect to the baseline value; whereby the baseline value represents a usual affective response of the user, as computed from multiple values acquired over a period of at least a few hours.

17. The non-transitory computer-readable medium of claim 15, wherein the total affective response is expressed as an emotional response.

18. The non-transitory computer-readable medium of claim 15, wherein the total affective response is based on values of a user measurement channel of the user.

19. The non-transitory computer-readable medium of claim 15, wherein the total affective response is proportional to a difference between affective responses of the user before and after the user was exposed to the token instances.

20. The non-transitory computer-readable medium of claim 15, wherein more than 50% of the total affective response is attributed to the affective response to the token instance of interest.

* * * * *

UNITED STATES PATENT AND TRADEMARK OFFICE
CERTIFICATE OF CORRECTION

PATENT NO. : 9,015,084 B2  
APPLICATION NO. : 13/656704  
DATED : April 21, 2015  
INVENTOR(S) : Gil Thieberger and Ari M. Frank Page 1 of 1

It is certified that error appears in the above-identified patent and that said Letters Patent is hereby corrected as shown below:

In the specification:

Column 66, Line 51, please delete "honor" and insert --horror--, therefor.

In the claims:

Column 80, Line 63, in Claim 8, please insert --of interest-- after "as the token instance".

Signed and Sealed this
Eleventh Day of August, 2015

Michelle K. Lee
*Director of the United States Patent and Trademark Office*